United States Patent
Beste et al.

(10) Patent No.: US 12,195,546 B2
(45) Date of Patent: Jan. 14, 2025

(54) CD28/OX40 BISPECIFIC ANTIBODIES

(71) Applicant: SANOFI, Paris (FR)

(72) Inventors: Gerald Beste, Ghent (BE); Yanik Bruynooghe, Ghent (BE); Klervi Desrumeaux, Paris (FR); Jennifer Kuehn, Frankfurt am Main (DE); Charlotte Lahoute, Paris (FR); Rami Lissilaa, Paris (FR); Alessandro Masiero, Paris (FR); Sevim Oezguer Bruederle, Frankfurt am Main (DE); Benjamin Suratt, Cambridge, MA (US); Emmanuelle Vigne, Paris (FR); Jessica Voss, Cambridge, MA (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 18/543,673

(22) Filed: Dec. 18, 2023

(65) Prior Publication Data

US 2024/0209107 A1    Jun. 27, 2024

Related U.S. Application Data

(60) Provisional application No. 63/543,351, filed on Oct. 10, 2023.

(30) Foreign Application Priority Data

Dec. 19, 2022 (EP) .................................. 22315332

(51) Int. Cl.
C07K 16/28 (2006.01)
(52) U.S. Cl.
CPC ...... *C07K 16/2878* (2013.01); *C07K 16/2818* (2013.01); *C07K 2317/31* (2013.01); *C07K 2317/569* (2013.01)

(58) Field of Classification Search
None
See application file for complete search history.

(56) References Cited

U.S. PATENT DOCUMENTS

| | | |
|---|---|---|
| 5,731,168 A | 3/1998 | Carter et al. |
| 8,216,805 B2 | 7/2012 | Carter et al. |

(Continued)

FOREIGN PATENT DOCUMENTS

| | | |
|---|---|---|
| EP | 4083069 A1 | 11/2022 |
| WO | WO 2010/007376 A2 | 1/2010 |

(Continued)

OTHER PUBLICATIONS

Yassky et al. GBR 830, an anti-OX40, improves skin gene signatures and clinical scores in patients with atopic dermatitis. Journal of Allergy and Clinical Immunology. vol. 144, Iss 2, Aug. 2019, pp. 482-493. (Year: 2019).*

(Continued)

*Primary Examiner* — Daniel E Kolker
*Assistant Examiner* — Hilary Ann Petrash
(74) *Attorney, Agent, or Firm* — LATHROP GPM LLP; James H. Velema, Esq.; Michael J. Spellberg, Esq.

(57) ABSTRACT

Provided herein are multispecific binding proteins comprising (a) a first antigen binding domain (ABD) comprising an immunoglobulin single variable domain (ISVD) (e.g., VHH) with binding specificity to CD28; and (b) a second ABD comprising an immunoglobulin heavy chain variable domain (VH) and an immunoglobulin light chain variable domain (VL) with binding specificity to OX40. Also provided are methods of treating autoimmune diseases with said multispecific binding proteins.

26 Claims, 51 Drawing Sheets

Specification includes a Sequence Listing.

(56) References Cited

U.S. PATENT DOCUMENTS

| | | |
|---|---|---|
| 8,586,713 B2 | 11/2013 | Davis et al. |
| 8,642,745 B2 | 2/2014 | Arathoon et al. |
| 8,907,065 B2 | 12/2014 | Hermans et al. |
| 9,758,592 B2 | 9/2017 | Deshpande et al. |
| 11,447,573 B2 | 9/2022 | Chou et al. |
| 2011/0189203 A1 | 8/2011 | Hermans et al. |
| 2013/0330344 A1 | 12/2013 | Lawson et al. |
| 2015/0239991 A1 | 8/2015 | Blein et al. |
| 2018/0118841 A1 | 5/2018 | Ellmark et al. |
| 2018/0273643 A1 | 9/2018 | Ast et al. |
| 2019/0218310 A1 | 7/2019 | Van Der Woning et al. |
| 2021/0032362 A1 | 2/2021 | Ma |
| 2021/0206864 A1 | 7/2021 | Back et al. |
| 2021/0214453 A1 | 7/2021 | Back et al. |
| 2022/0041702 A1 | 2/2022 | Liu et al. |
| 2022/0112284 A1 | 4/2022 | Ni et al. |
| 2022/0251138 A1 | 8/2022 | Giovanni et al. |
| 2023/0203199 A1 | 6/2023 | Wei et al. |
| 2023/0236188 A1 | 7/2023 | Menard et al. |
| 2023/0303698 A1 | 9/2023 | He et al. |

FOREIGN PATENT DOCUMENTS

| | | |
|---|---|---|
| WO | WO 2010/007376 A3 | 1/2010 |
| WO | WO 2022/198055 A1 | 9/2022 |
| WO | WO 2023/153388 A1 | 8/2023 |
| WO | WO 2023/193239 A1 | 10/2023 |

OTHER PUBLICATIONS

Wu et al. Trispecific antibodies enhance the therapeutic efficacy of tumor-directed T cells through T cell receptor co-stimulation. Nat Cancer 1, 86-98 (2020). https://doi.org/10.1038/s43018-019-0004-z (Year: 2020).*

Brinkmann et al., "The making of bispecific antibodies", MABS, Feb./Mar. 2017, 9(2): 182-212.

Edner et al., "Targeting co-stimulatory molecules in autoimmune diseases", Nature, Dec. 2020, 19: 860-883.

International Search Report and Written Opinion for PCT International Patent Application No. PCT/EP2023/086624, dated May 27, 2024.

* cited by examiner

| Bispecific lead ID | #L1 | #L2 | #L3 | #L4 | #L5 | #L6 | Abatacept | Belatacept | anti-CD28 benchmark |
|---|---|---|---|---|---|---|---|---|---|
| GeoMean of EC50 (nM) [95%CI] (IL2) | 0.06 [0.03 ; 0.12] | 0.06 [0.04 ; 0.08] | 0.08 [0.05 ; 0.14] | 0.22 [0.04 ; 1.35] | 0.26 [0.23 ; 0.29] | 0.53 [0.36 ; 0.8] | 7.63 [1.29 ; 45.1] | 0.5 [0.05 ; 5.29] | 1.01 [0.17 ; 6.12] |
| GeoMean of EC50 (nM) [95%CI] (IL5) | 0.33 [0.12 ; 0.91] | 0.29 [0.06 ; 1.39] | 0.54 [0.09 ; 3.11] | 0.68 [0.37 ; 1.24] | 1.26 [0.14 ; 11.43] | 4.37 [0.22 ; 87.45] | 21.18 [8.37 ; 53.57] | 1.26 [0.17 ; 9.6] | 1.82 [0.42 ; 7.85] |
| GeoMean of EC50 (nM) [95%CI] (GMCSF) | 0.92 [0.15 ; 5.5] | 1.18 [0.18 ; 7.89] | 1.64 [0.16 ; 16.93] | 3.18 [0 ; 6491.28] | 6.1 [0.27 ; 137.15] | 8.85 [0.63 ; 123.6] | 46.29 [6.94 ; 308.6] | 1.7 [0.26 ; 11.05] | 2.93 [1.45 ; 5.91] |
| GeoMean of EC50 (nM) [95%CI] (TNFa) | 0.44 [0 ; 139.31] | 1.44 [0.04 ; 48] | 0.12 [0.01 ; 1.83] | 0.41 | 0.58 [0 ; 2326.51] | 1.46 [0 ; 680.73] | 12.72 [10.42 ; 15.52] | 1.24 [0.6 ; 2.56] | 2.86 [1.39 ; 5.91] |
| GeoMean of EC50 (nM) [95%CI] (IFNg) | 0.41 [0.04 ; 3.77] | 1.8 [0.1 ; 33.57] | 1.33 [0.15 ; 12.17] | 0.31 [0.17 ; 0.59] | 10.3 [0 ; 745731.38] | 10.21 [0 ; 878841.88] | 6.08 [0.27 ; 136.06] | 0.23 [0.03 ; 1.93] | 2.29 [0.63 ; 8.36] |

FIG. 6A

|  | CL (mL/h/kg) | $V_{ss}$ (mL/kg) | $T_{1/2}$ (h) | $AUC_{inf}$ (h*ug/mL) |
|---|---|---|---|---|
| #L1 | 0.286 | 128 | 334 | 17700 |
| #L2 | 0.376 | 134 | 262 | 13300 |
| #L3 | 0.224 | 124 | 409 | 22600 |
| #L4 | 0.171 | 111 | 455 | 29300 |
| #L5 | 0.363 | 127 | 270 | 14100 |
| #L6 | 0.482 | 167 | 270 | 10400 |

FIG. 10

CD28/OX40 BISPECIFIC ANTIBODIES

RELATED APPLICATIONS

This application claims priority to European Patent Application No. 22315332.1, filed Dec. 19, 2022, and U.S. Provisional Patent Application Ser. No. 63/543,351, filed Oct. 10, 2023, the disclosure of each is hereby incorporated by reference in their entirety.

SEQUENCE LISTING

The instant application contains a Sequence Listing which has been submitted electronically in XML format and is hereby incorporated by reference in its entirety. Said XML file, created on Dec. 15, 2023, is named 747977_SA9-341_ST26.xml and is 93,757 bytes in size.

FIELD OF THE INVENTION

This disclosure relates to novel antibodies and antigen-binding fragments thereof that specifically bind to CD28 and OX40, and methods of using the same.

BACKGROUND

T cell-mediated autoimmunity has numerous deleterious effects on health, manifesting as any one of a variety of autoimmune diseases. T cell-mediated autoimmunity results, in part, through the activity of the co-stimulatory T cell receptors CD28 and OX40. Therapeutic strategies are currently tested for antagonizing the either one of CD28 or OX40 in an attempt to treat autoimmune diseases.

Successful repression of T cell-mediated autoimmunity is likely to require intervention at different levels simultaneously. Accordingly, there exists a need for therapeutics that antagonize both CD28 and OX40.

SUMMARY

The bispecific antigen binding proteins of the disclosure are capable of antagonizing both CD28 and OX40 on the surfaces of T cells. The anti-OX40 antigen binding domain of the bispecific antigen binding protein 1) inhibits the survival and activation of effector T cells generated from either naive or memory T cells; 2) reduces Tfh responses that promote autoantibody production; and 3) increases selectivity of the bispecific to activated T cells in inflammatory sites. The anti-CD28 antigen binding domain of the bispecific antigen binding protein 1) suppresses the generation of effector T cells from naive T cells; and 2) preserves the suppressive function of Tregs by selectively blocking the CD28-B7 interaction while preserving CTLA4-B7-mediated regulatory mechanisms (unlike Abatacept and Belatacept). These complementary functions of the bispecific antibody can potently and selectively control expansion of effector/memory T-cells in severe immune-related disorders.

In one aspect, the disclosure provides a multispecific binding protein comprising: (a) a first antigen binding domain (ABD) comprising an immunoglobulin single variable domain (ISVD) (e.g., VHH) with binding specificity to CD28; and (b) a second ABD comprising an immunoglobulin heavy chain variable domain (VH) and an immunoglobulin light chain variable domain (VL) with binding specificity to OX40, wherein when the multispecific binding protein binds CD28 and OX40, the multispecific binding protein inhibits activated T-cells.

In certain embodiments, the multispecific binding protein inhibits proliferation of T-cells.

In certain embodiments, the multispecific binding protein inhibits expression of one or more pro-inflammatory cytokines.

In certain embodiments, the pro-inflammatory cytokines are interferon gamma (IFNγ), tumor necrosis factor alpha (TNFα), interleukin 2 (IL-2), interleukin 5 (IL-5), interleukin 6 (IL-6), and interleukin 10 (IL-10).

In certain embodiments, the multispecific binding protein further comprises an immunoglobulin Fc domain or variant thereof.

In certain embodiments, the Fc domain or variant thereof comprises a first Fc heavy chain and a second Fc heavy chain.

In certain embodiments, the first ABD is linked to the first Fc heavy chain and the second ABD is linked to the second Fc heavy chain.

In certain embodiments, the first ABD is linked to the N-terminus of the second ABD VH.

In certain embodiments, the first ABD is linked to the C-terminus of the second Fc heavy chain and the second ABD is linked to the N-terminus of the second Fc heavy chain.

In certain embodiments, the VH is linked to a CH1 domain and the VL is linked to a constant light (CL) domain.

In certain embodiments, the first ABD is linked to the C-terminus of the CL domain.

In certain embodiments, the first ABD binds to one or more amino acids E32, E46, V47, C48, Y51, G52, N53, S55, Q57, L58, Q59, V60, Y61, S62, K63, T64, N67, C68, and D69 of SEQ ID NO: 46. In certain embodiments, the first ABD binds to amino acids E32, E46, V47, C48, Y51, G52, N53, S55, Q57, L58, Q59, V60, Y61, S62, K63, T64, N67, C68, and D69 of SEQ ID NO: 46.

In certain embodiments, the second ABD binds to one or more amino acids V22, C33, R34, P35, C36, G37, P38, G39, F40, P49, C50, C53, W55, R64, L67, C68, T69, and A70 of SEQ ID NO: 47. In certain embodiments, the second ABD binds to amino acids V22, C33, R34, P35, C36, G37, P38, G39, F40, P49, C50, C53, W55, R64, L67, C68, T69, and A70 of SEQ ID NO: 47.

In certain embodiments, the second ABD binds to one or more amino acids R16, N19, V22, V32, C33, R34, P35, C36, G37, P38, G39, F40, P49, C50, C53, T54, W55, C56, R64, L67, C68, T69, A70, and T74 of SEQ ID NO: 47. In certain embodiments, the second ABD binds to amino acids R16, N19, V22, V32, C33, R34, P35, C36, G37, P38, G39, F40, P49, C50, C53, T54, W55, C56, R64, L67, C68, T69, A70, and T74 of SEQ ID NO: 47.

In certain embodiments, the multispecific binding protein comprises:
(a) a first antigen binding domain (ABD) with binding specificity to CD28 comprising:
an immunoglobulin single variable domain (ISVD) comprising
an HCDR1 sequence comprising the amino acid sequence of GFTFSSYY (SEQ ID NO: 1),
an HCDR2 sequence comprising the amino acid sequence of INTDGDFT (SEQ ID NO: 2), and
an HCDR3 sequence comprising the amino acid sequence of ARARGPYSRGSQGHDY (SEQ ID NO: 3);
(b) a second ABD with binding affinity to OX40 comprising:
(b1) an immunoglobulin heavy chain variable domain (VH) comprising an HCDR1 sequence comprising the amino acid sequence of GFTFSSYA (SEQ ID NO: 4),
an HCDR2 sequence comprising the amino acid sequence of ISSQGGST (SEQ ID NO: 5), and
an HCDR3 sequence comprising the amino acid sequence of ARGEAYWYRWAFDY (SEQ ID NO: 6); and
(b2) an immunoglobulin light chain variable domain (VL) comprising
an LCDR1 sequence comprising the amino acid sequence QSISSW (SEQ ID NO: 7),
an LCDR2 sequence comprising the amino acid sequence of DAS (SEQ ID NO: 8), and
an LCDR3 sequence comprising the amino acid sequence of QQYSDYSYT (SEQ ID NO: 9).

In certain embodiments, the multispecific binding protein comprises:
(a) a first antigen binding domain (ABD) with binding specificity to CD28 comprising:
an immunoglobulin single variable domain (ISVD) comprising
an HCDR1 sequence comprising the amino acid sequence of GSFFSIDT (SEQ ID NO: 13),
an HCDR2 sequence comprising the amino acid sequence of VTSGGLT (SEQ ID NO: 14), and
an HCDR3 sequence comprising the amino acid sequence of SARIRTSGGGGWSTY (SEQ ID NO: 15);
(b) a second ABD with binding affinity to OX40 comprising:
(b1) an immunoglobulin heavy chain variable domain (VH) comprising
an HCDR1 sequence comprising the amino acid sequence of GFTFSSYA (SEQ ID NO: 4),
an HCDR2 sequence comprising the amino acid sequence of ISSQGGST (SEQ ID NO: 5), and
an HCDR3 sequence comprising the amino acid sequence of ARGEAYWYRWAFDY (SEQ ID NO: 6); and
(b2) an immunoglobulin light chain variable domain (VL) comprising
an LCDR1 sequence comprising the amino acid sequence QSISSW (SEQ ID NO: 7),
an LCDR2 sequence comprising the amino acid sequence of DAS (SEQ ID NO: 8), and
an LCDR3 sequence comprising the amino acid sequence of QQYSDYSYT (SEQ ID NO: 9).

In certain embodiments, the multispecific binding protein comprises:
(a) a first antigen binding domain (ABD) with binding specificity to CD28 comprising:
an immunoglobulin single variable domain (ISVD) comprising
an HCDR1 sequence comprising the amino acid sequence of GFTFSSYY (SEQ ID NO: 1),
an HCDR2 sequence comprising the amino acid sequence of INTDGDFT (SEQ ID NO: 2), and
an HCDR3 sequence comprising the amino acid sequence of ARARGPYSRGSQGHDY (SEQ ID NO: 3);
(b) a second ABD with binding affinity to OX40 comprising:
(b1) an immunoglobulin heavy chain variable domain (VH) comprising
an HCDR1 sequence comprising the amino acid sequence of GYTFTSYG (SEQ ID NO: 17),
an HCDR2 sequence comprising the amino acid sequence of ISAYTGNT (SEQ ID NO: 18), and
an HCDR3 sequence comprising the amino acid sequence of ARDGYPIDY (SEQ ID NO: 19); and
(b2) an immunoglobulin light chain variable domain (VL) comprising
an LCDR1 sequence comprising the amino acid sequence QSISSW (SEQ ID NO: 20),
an LCDR2 sequence comprising the amino acid sequence of DAS (SEQ ID NO: 21), and
an LCDR3 sequence comprising the amino acid sequence of QQYTSYSDT (SEQ ID NO: 22).

In certain embodiments, the multispecific binding protein comprises:
(a) a first antigen binding domain (ABD) with binding specificity to CD28 comprising:
an immunoglobulin single variable domain (ISVD) comprising
an HCDR1 sequence comprising the amino acid sequence of GSFFSIDT (SEQ ID NO: 13),
an HCDR2 sequence comprising the amino acid sequence of VTSGGLT (SEQ ID NO: 14), and
an HCDR3 sequence comprising the amino acid sequence of SARIRTSGGGGWSTY (SEQ ID NO: 15);
(b) a second ABD with binding affinity to OX40 comprising:
(b1) an immunoglobulin heavy chain variable domain (VH) comprising
an HCDR1 sequence comprising the amino acid sequence of GYTFTSYG (SEQ ID NO: 17),
an HCDR2 sequence comprising the amino acid sequence of ISAYTGNT (SEQ ID NO: 18), and
an HCDR3 sequence comprising the amino acid sequence of ARDGYPIDY (SEQ ID NO: 19); and
(b2) an immunoglobulin light chain variable domain (VL) comprising
an LCDR1 sequence comprising the amino acid sequence QSISSW (SEQ ID NO: 20),
an LCDR2 sequence comprising the amino acid sequence of DAS (SEQ ID NO: 21), and
an LCDR3 sequence comprising the amino acid sequence of QQYTSYSDT (SEQ ID NO: 22).

In certain embodiments, the multispecific binding protein comprises:
(a) a first antigen binding domain (ABD) with binding specificity to CD28 comprising:
an immunoglobulin single variable domain (ISVD) comprising
an HCDR1 sequence comprising the amino acid sequence of GFTFSSYY (SEQ ID NO: 1),
an HCDR2 sequence comprising the amino acid sequence of INTDGDFT (SEQ ID NO: 2), and
an HCDR3 sequence comprising the amino acid sequence of ARARGPYSRGSQGHDY (SEQ ID NO: 3);
(b) a second ABD with binding affinity to OX40 comprising:
(b1) an immunoglobulin heavy chain variable domain (VH) comprising
an HCDR1 sequence comprising the amino acid sequence of GFTFSSYA (SEQ ID NO: 25),
an HCDR2 sequence comprising the amino acid sequence of ISSQGGST (SEQ ID NO: 26), and
an HCDR3 sequence comprising the amino acid sequence of ARGGSGWYNSEFDY (SEQ ID NO: 27); and
(b2) an immunoglobulin light chain variable domain (VL) comprising
an LCDR1 sequence comprising the amino acid sequence QSISSW (SEQ ID NO: 28),
an LCDR2 sequence comprising the amino acid sequence of DAS (SEQ ID NO: 29), and an LCDR3 sequence comprising the amino acid sequence of QQYNDYSYT (SEQ ID NO: 30).

In certain embodiments, the multispecific binding protein comprises:
(a) a first antigen binding domain (ABD) with binding specificity to CD28 comprising:
an immunoglobulin single variable domain (ISVD) comprising
an HCDR1 sequence comprising the amino acid sequence of GSFFSIDT (SEQ ID NO: 13),
an HCDR2 sequence comprising the amino acid sequence of VTSGGLT (SEQ ID NO: 14), and
an HCDR3 sequence comprising the amino acid sequence of SARIRTSGGGGWSTY (SEQ ID NO: 15);
(b) a second ABD with binding affinity to OX40 comprising:
(b1) an immunoglobulin heavy chain variable domain (VH) comprising
an HCDR1 sequence comprising the amino acid sequence of GFTFSSYA (SEQ ID NO: 25),
an HCDR2 sequence comprising the amino acid sequence of ISSQGGST (SEQ ID NO: 26), and
an HCDR3 sequence comprising the amino acid sequence of ARGGSGWYNSEFDY (SEQ ID NO: 27); and
(b2) an immunoglobulin light chain variable domain (VL) comprising
an LCDR1 sequence comprising the amino acid sequence QSISSW (SEQ ID NO: 28),
an LCDR2 sequence comprising the amino acid sequence of DAS (SEQ ID NO: 29), and
an LCDR3 sequence comprising the amino acid sequence of QQYNDYSYT (SEQ ID NO: 30).

In certain embodiments:
the ISVD comprises an amino acid sequence that is at least about 90% identical to the amino acid sequence of SEQ ID NO: 10; and
the VH comprises an amino acid sequence that is at least about 90% identical to the amino acid sequence of SEQ ID NO: 11 and the VL comprises an amino acid sequence that is at least about 90% identical to the amino acid sequence of SEQ ID NO: 12.

In certain embodiments, the ISVD comprises an amino acid sequence that is at least about 80% identical to the amino acid sequence of SEQ ID NO: 10 and comprises amino acid Y33, W47, T50, N52, D56, F57, T58, S59, K65, P102, Y103, S104, and R105 relative to SEQ ID NO: 10.

In certain embodiments, the VH comprises an amino acid sequence that is at least about 80% identical to the amino acid sequence of SEQ ID NO: 11 and comprises amino acids H35, S52, Q54, G56, S57, T58, Y59, Y102, Y104, R105, and W106 relative to SEQ ID NO: 11, and the VL comprises an amino acid sequence that is at least about 80% identical to the amino acid sequence of SEQ ID NO: 12 and comprises amino acids W32, D50, and S92 relative to SEQ ID NO: 12.

In certain embodiments:
the ISVD comprises an amino acid sequence that is at least about 90% identical to the amino acid sequence of SEQ ID NO: 16; and
the VH comprises an amino acid sequence that is at least about 90% identical to the amino acid sequence of SEQ ID NO: 11 and the VL comprises an amino acid sequence that is at least about 90% identical to the amino acid sequence of SEQ ID NO: 12.

In certain embodiments:
the ISVD comprises an amino acid sequence that is at least about 90% identical to the amino acid sequence of SEQ ID NO: 10; and
the VH comprises an amino acid sequence that is at least about 90% identical to the amino acid sequence of SEQ ID NO: 23 and the VL comprises an amino acid sequence that is at least about 90% identical to the amino acid sequence of SEQ ID NO: 24.

In certain embodiments:
the ISVD comprises an amino acid sequence that is at least about 90% identical to the amino acid sequence of SEQ ID NO: 16; and
the VH comprises an amino acid sequence that is at least about 90% identical to the amino acid sequence of SEQ ID NO: 23 and the VL comprises an amino acid sequence that is at least about 90% identical to the amino acid sequence of SEQ ID NO: 24.

In certain embodiments:
the ISVD comprises an amino acid sequence that is at least about 90% identical to the amino acid sequence of SEQ ID NO: 10; and
the VH comprises an amino acid sequence that is at least about 90% identical to the amino acid sequence of SEQ ID NO: 31 and the VL comprises an amino acid sequence that is at least about 90% identical to the amino acid sequence of SEQ ID NO: 32.

In certain embodiments:
the ISVD comprises an amino acid sequence that is at least about 90% identical to the amino acid sequence of SEQ ID NO: 16; and
the VH comprises an amino acid sequence that is at least about 90% identical to the amino acid sequence of SEQ ID NO: 31 and the VL comprises an amino acid sequence that is at least about 90% identical to the amino acid sequence of SEQ ID NO: 32.

In certain embodiments, the VH comprises an amino acid sequence that is at least about 80% identical to the amino acid sequence of SEQ ID NO: 31 and comprises amino acids A33, H35, A50, I51, S52, S53, N54, G55, G56, S57, T58, Y59, Y60, N74, S101, W103, Y104, N105, S106, and E107 relative to SEQ ID NO: 31, and the VL comprises an amino acid sequence that is at least about 80% identical to the amino acid sequence of SEQ ID NO: 32 and comprises amino acids W32, Y91, N92, Y94, and Y96 relative to SEQ ID NO: 32.

In certain embodiments, the first Fc heavy chain comprises a Y349C substitution and the second Fc heavy chain comprises a S354C substitution.

In certain embodiments, the first Fc heavy chain comprises a Y349C, T366S, L368A, or Y407V substitutions and the second Fc heavy chain comprises a T366W substitution.

In certain embodiments, at least one Fc heavy chain comprises H435R and Y436F substitutions.

In certain embodiments, at least one Fc heavy chain comprises L234A and L235A substitutions.

In certain embodiments, the multispecific binding protein comprises: (i) a first polypeptide chain comprising an amino acid sequence of SEQ ID NO: 33; (ii) a second polypeptide chain comprising an amino acid sequence of SEQ ID NO: 36; and (iii) a third polypeptide chain comprising an amino acid sequence of SEQ ID NO: 41.

In certain embodiments, the multispecific binding protein comprises: (i) a first polypeptide chain comprising an amino acid sequence of SEQ ID NO: 33; (ii) a second polypeptide chain comprising an amino acid sequence of SEQ ID NO: 37; and (iii) a third polypeptide chain comprising an amino acid sequence of SEQ ID NO: 42.

In certain embodiments, the multispecific binding protein comprises: (i) a first polypeptide chain comprising an amino acid sequence of SEQ ID NO: 34; (ii) a second polypeptide chain comprising an amino acid sequence of SEQ ID NO: 38; and (iii) a third polypeptide chain comprising an amino acid sequence of SEQ ID NO: 41.

In certain embodiments, the multispecific binding protein comprises: (i) a first polypeptide chain comprising an amino acid sequence of SEQ ID NO: 34; (ii) a second polypeptide chain comprising an amino acid sequence of SEQ ID NO: 39; and (iii) a third polypeptide chain comprising an amino acid sequence of SEQ ID NO: 42.

In certain embodiments, the multispecific binding protein comprises: (i) a first polypeptide chain comprising an amino acid sequence of SEQ ID NO: 35; (ii) a second polypeptide chain comprising an amino acid sequence of SEQ ID NO: 40; and (iii) a third polypeptide chain comprising an amino acid sequence of SEQ ID NO: 41.

In certain embodiments, the multispecific binding protein comprises: (i) a first polypeptide chain comprising an amino acid sequence of SEQ ID NO: 35; (ii) a second polypeptide chain comprising an amino acid sequence of SEQ ID NO: 40; and (iii) a third polypeptide chain comprising an amino acid sequence of SEQ ID NO: 42.

In one aspect, the disclosure provides a binding protein comprising:
(a) a first antigen binding domain (ABD) with binding specificity to CD28 comprising:
an immunoglobulin single variable domain (ISVD) comprising
an HCDR1 sequence comprising the amino acid sequence of GFTFSSYY (SEQ ID NO: 1),
an HCDR2 sequence comprising the amino acid sequence of INTDGDFT (SEQ ID NO: 2), and
an HCDR3 sequence comprising the amino acid sequence of ARARGPYSRGSQGHDY (SEQ ID NO: 3); and
(b) a second ABD with binding affinity to OX40 comprising:
(b1) an immunoglobulin heavy chain variable domain (VH) comprising
an HCDR1 sequence comprising the amino acid sequence of GFTFSSYA (SEQ ID NO: 4),
an HCDR2 sequence comprising the amino acid sequence of ISSQGGST (SEQ ID NO: 5), and
an HCDR3 sequence comprising the amino acid sequence of ARGEAYWYRWAFDY (SEQ ID NO: 6); and
(b2) an immunoglobulin light chain variable domain (VL) comprising
an LCDR1 sequence comprising the amino acid sequence QSISSW (SEQ ID NO: 7),
an LCDR2 sequence comprising the amino acid sequence of DAS (SEQ ID NO: 8), and
an LCDR3 sequence comprising the amino acid sequence of QQYSDYSYT (SEQ ID NO: 9).

In certain embodiments, the ISVD comprises an amino acid sequence that is at least about 90% identical to the amino acid sequence of SEQ ID NO: 10.

In certain embodiments, the VH comprises an amino acid sequence that is at least about 90% identical to the amino acid sequence of SEQ ID NO: 11 and the VL comprises an amino acid sequence that is at least about 90% identical to the amino acid sequence of SEQ ID NO: 12.

In one aspect, the disclosure provides a binding protein comprising:
(a) a first antigen binding domain (ABD) with binding specificity to CD28 comprising:
an immunoglobulin single variable domain (ISVD) comprising
an HCDR1 sequence comprising the amino acid sequence of GSFFSIDT (SEQ ID NO: 13),
an HCDR2 sequence comprising the amino acid sequence of VTSGGLT (SEQ ID NO: 14), and
an HCDR3 sequence comprising the amino acid sequence of SARIRTSGGGGWSTY (SEQ ID NO: 15); and
(b) a second ABD with binding affinity to OX40 comprising:
(b1) an immunoglobulin heavy chain variable domain (VH) comprising
an HCDR1 sequence comprising the amino acid sequence of GFTFSSYA (SEQ ID NO: 4),
an HCDR2 sequence comprising the amino acid sequence of ISSQGGST (SEQ ID NO: 5), and
an HCDR3 sequence comprising the amino acid sequence of ARGEAYWYRWAFDY (SEQ ID NO: 6); and
(b2) an immunoglobulin light chain variable domain (VL) comprising
an LCDR1 sequence comprising the amino acid sequence QSISSW (SEQ ID NO: 7),
an LCDR2 sequence comprising the amino acid sequence of DAS (SEQ ID NO: 8), and
an LCDR3 sequence comprising the amino acid sequence of QQYSDYSYT (SEQ ID NO: 9).

In certain embodiments, the ISVD comprises an amino acid sequence that is at least about 90% identical to the amino acid sequence of SEQ ID NO: 16.

In certain embodiments, the VH comprises an amino acid sequence that is at least about 90% identical to the amino acid sequence of SEQ ID NO: 11 and the VL comprises an amino acid sequence that is at least about 90% identical to the amino acid sequence of SEQ ID NO: 12.

In one aspect, the disclosure provides a binding protein comprising:
(a) a first antigen binding domain (ABD) with binding specificity to CD28 comprising:
an immunoglobulin single variable domain (ISVD) comprising
an HCDR1 sequence comprising the amino acid sequence of GFTFSSYY (SEQ ID NO: 1),
an HCDR2 sequence comprising the amino acid sequence of INTDGDFT (SEQ ID NO: 2), and
an HCDR3 sequence comprising the amino acid sequence of ARARGPYSRGSQGHDY (SEQ ID NO: 3); and
(b) a second ABD with binding affinity to OX40 comprising:
(b1) an immunoglobulin heavy chain variable domain (VH) comprising
an HCDR1 sequence comprising the amino acid sequence of GYTFTSYG (SEQ ID NO: 17),
an HCDR2 sequence comprising the amino acid sequence of ISAYTGNT (SEQ ID NO: 18), and
an HCDR3 sequence comprising the amino acid sequence of ARDGYPIDY (SEQ ID NO: 19); and
(b2) an immunoglobulin light chain variable domain (VL) comprising
an LCDR1 sequence comprising the amino acid sequence QSISSW (SEQ ID NO: 20),
an LCDR2 sequence comprising the amino acid sequence of DAS (SEQ ID NO: 21), and
an LCDR3 sequence comprising the amino acid sequence of QQYTSYSDT (SEQ ID NO: 22).

In certain embodiments, the ISVD comprises an amino acid sequence that is at least about 90% identical to the amino acid sequence of SEQ ID NO: 10.

In certain embodiments, the VH comprises an amino acid sequence that is at least about 90% identical to the amino acid sequence of SEQ ID NO: 23 and the VL comprises an amino acid sequence that is at least about 90% identical to the amino acid sequence of SEQ ID NO: 24.

In one aspect, the disclosure provides a binding protein comprising:
(a) a first antigen binding domain (ABD) with binding specificity to CD28 comprising:
an immunoglobulin single variable domain (ISVD) comprising
an HCDR1 sequence comprising the amino acid sequence of GSFFSIDT (SEQ ID NO: 13),
an HCDR2 sequence comprising the amino acid sequence of VTSGGLT (SEQ ID NO: 14), and
an HCDR3 sequence comprising the amino acid sequence of SARIRTSGGGGWSTY (SEQ ID NO: 15); and
(b) a second ABD with binding affinity to OX40 comprising:
(b1) an immunoglobulin heavy chain variable domain (VH) comprising
an HCDR1 sequence comprising the amino acid sequence of GYTFTSYG (SEQ ID NO: 17),
an HCDR2 sequence comprising the amino acid sequence of ISAYTGNT (SEQ ID NO: 18), and
an HCDR3 sequence comprising the amino acid sequence of ARDGYPIDY (SEQ ID NO: 19); and
(b2) an immunoglobulin light chain variable domain (VL) comprising
an LCDR1 sequence comprising the amino acid sequence QSISSW (SEQ ID NO: 20),
an LCDR2 sequence comprising the amino acid sequence of DAS (SEQ ID NO: 21), and
an LCDR3 sequence comprising the amino acid sequence of QQYTSYSDT (SEQ ID NO: 22).

In certain embodiments, the ISVD comprises an amino acid sequence that is at least about 90% identical to the amino acid sequence of SEQ ID NO: 16.

In certain embodiments, the VH comprises an amino acid sequence that is at least about 90% identical to the amino acid sequence of SEQ ID NO: 23 and the VL comprises an amino acid sequence that is at least about 90% identical to the amino acid sequence of SEQ ID NO: 24.

In one aspect, the disclosure provides a binding protein comprising:
(a) a first antigen binding domain (ABD) with binding specificity to CD28 comprising:
an immunoglobulin single variable domain (ISVD) comprising
an HCDR1 sequence comprising the amino acid sequence of GFTFSSYY (SEQ ID NO: 1),
an HCDR2 sequence comprising the amino acid sequence of INTDGDFT (SEQ ID NO: 2), and
an HCDR3 sequence comprising the amino acid sequence of ARARGPYSRGSQGHDY (SEQ ID NO: 3); and
(b) a second ABD with binding affinity to OX40 comprising:
(b1) an immunoglobulin heavy chain variable domain (VH) comprising
an HCDR1 sequence comprising the amino acid sequence of GFTFSSYA (SEQ ID NO: 25),
an HCDR2 sequence comprising the amino acid sequence of ISSQGGST (SEQ ID NO: 26), and
an HCDR3 sequence comprising the amino acid sequence of ARGGSGWYNSEFDY (SEQ ID NO: 27); and
(b2) an immunoglobulin light chain variable domain (VL) comprising
an LCDR1 sequence comprising the amino acid sequence QSISSW (SEQ ID NO: 28),
an LCDR2 sequence comprising the amino acid sequence of DAS (SEQ ID NO: 29), and
an LCDR3 sequence comprising the amino acid sequence of QQYNDYSYT (SEQ ID NO: 30).

In certain embodiments, the ISVD comprises an amino acid sequence that is at least about 90% identical to the amino acid sequence of SEQ ID NO: 10.

In certain embodiments, the VH comprises an amino acid sequence that is at least about 90% identical to the amino acid sequence of SEQ ID NO: 31 and the VL comprises an amino acid sequence that is at least about 90% identical to the amino acid sequence of SEQ ID NO: 32.

In one aspect, the disclosure provides a binding protein comprising:
(a) a first antigen binding domain (ABD) with binding specificity to CD28 comprising:
an immunoglobulin single variable domain (ISVD) comprising
an HCDR1 sequence comprising the amino acid sequence of GSFFSIDT (SEQ ID NO: 13),
an HCDR2 sequence comprising the amino acid sequence of VTSGGLT (SEQ ID NO: 14), and
an HCDR3 sequence comprising the amino acid sequence of SARIRTSGGGGWSTY (SEQ ID NO: 15); and
(b) a second ABD with binding affinity to OX40 comprising:
(b1) an immunoglobulin heavy chain variable domain (VH) comprising
an HCDR1 sequence comprising the amino acid sequence of GFTFSSYA (SEQ ID NO: 25),
an HCDR2 sequence comprising the amino acid sequence of ISSQGGST (SEQ ID NO: 26), and
an HCDR3 sequence comprising the amino acid sequence of ARGGSGWYNSEFDY (SEQ ID NO: 27); and
(b2) an immunoglobulin light chain variable domain (VL) comprising
an LCDR1 sequence comprising the amino acid sequence QSISSW (SEQ ID NO: 28),
an LCDR2 sequence comprising the amino acid sequence of DAS (SEQ ID NO: 29), and
an LCDR3 sequence comprising the amino acid sequence of QQYNDYSYT (SEQ ID NO: 30).

In certain embodiments, the ISVD comprises an amino acid sequence that is at least about 90% identical to the amino acid sequence of SEQ ID NO: 16.

In certain embodiments, the VH comprises an amino acid sequence that is at least about 90% identical to the amino acid sequence of SEQ ID NO: 31 and the VL comprises an amino acid sequence that is at least about 90% identical to the amino acid sequence of SEQ ID NO: 32.

In certain embodiments, the binding protein further comprises an immunoglobulin Fc domain or variant thereof.

In certain embodiments, the Fc domain or variant thereof comprises a first Fc heavy chain and a second Fc heavy chain.

In certain embodiments, the first Fc heavy chain comprises a Y349C substitution and the second Fc heavy chain comprises a S354C substitution.

In certain embodiments, the first Fc heavy chain comprises a Y349C, T366S, L368A, or Y407V substitutions and the second Fc heavy chain comprises a T366W substitution.

In certain embodiments, at least one Fc heavy chain comprises H435R and Y436F substitutions.

In certain embodiments, at least one Fc heavy chain comprises L234A and L235A substitutions.

In certain embodiments, the ISVD is a $V_{HH}$, a humanized $V_{HH}$ or a camelized $V_H$, or a suitable fragment thereof.

In one aspect, the disclosure provides a binding protein comprising a first antigen binding domain (ABD) with binding specificity to CD28 and a second ABD with binding affinity to OX40, wherein the binding protein comprises: (i) a first polypeptide chain comprising an amino acid sequence of SEQ ID NO: 33; (ii) a second polypeptide chain comprising an amino acid sequence of SEQ ID NO: 36; and (iii) a third polypeptide chain comprising an amino acid sequence of SEQ ID NO: 41.

In one aspect, the disclosure provides a binding protein comprising a first antigen binding domain (ABD) with binding specificity to CD28 and a second ABD with binding affinity to OX40, wherein the binding protein comprises: (i) a first polypeptide chain comprising an amino acid sequence of SEQ ID NO: 33; (ii) a second polypeptide chain comprising an amino acid sequence of SEQ ID NO: 37; and (iii) a third polypeptide chain comprising an amino acid sequence of SEQ ID NO: 42.

In one aspect, the disclosure provides a binding protein comprising a first antigen binding domain (ABD) with binding specificity to CD28 and a second ABD with binding affinity to OX40, wherein the binding protein comprises: (i) a first polypeptide chain comprising an amino acid sequence of SEQ ID NO: 34; (ii) a second polypeptide chain comprising an amino acid sequence of SEQ ID NO: 38; and (iii) a third polypeptide chain comprising an amino acid sequence of SEQ ID NO: 41.

In one aspect, the disclosure provides a binding protein comprising a first antigen binding domain (ABD) with binding specificity to CD28 and a second ABD with binding affinity to OX40, wherein the binding protein comprises: (i) a first polypeptide chain comprising an amino acid sequence of SEQ ID NO: 34; (ii) a second polypeptide chain comprising an amino acid sequence of SEQ ID NO: 39; and (iii) a third polypeptide chain comprising an amino acid sequence of SEQ ID NO: 42.

In one aspect, the disclosure provides a binding protein comprising a first antigen binding domain (ABD) with binding specificity to CD28 and a second ABD with binding affinity to OX40, wherein the binding protein comprises: (i) a first polypeptide chain comprising an amino acid sequence of SEQ ID NO: 35; (ii) a second polypeptide chain comprising an amino acid sequence of SEQ ID NO: 40; and (iii) a third polypeptide chain comprising an amino acid sequence of SEQ ID NO: 41.

In one aspect, the disclosure provides a binding protein comprising a first antigen binding domain (ABD) with binding specificity to CD28 and a second ABD with binding affinity to OX40, wherein the binding protein comprises: (i) a first polypeptide chain comprising an amino acid sequence of SEQ ID NO: 35; (ii) a second polypeptide chain comprising an amino acid sequence of SEQ ID NO: 40; and (iii) a third polypeptide chain comprising an amino acid sequence of SEQ ID NO: 42.

In one aspect, the disclosure provides a pharmaceutical composition comprising the binding protein described above and a pharmaceutically acceptable carrier.

In one aspect, the disclosure provides an isolated nucleic acid molecule encoding the binding protein described above.

In one aspect, the disclosure provides an expression vector comprising the nucleic acid molecule described above.

In one aspect, the disclosure provides a host cell comprising the expression vector described above.

In one aspect, the disclosure provides a method for treating an autoimmune disease or disorder in a subject, comprising administering to a subject in need thereof the binding protein described above. In certain embodiments, the autoimmune disease or disorder comprises connective tissue disease-interstitial lung disease (CTD-ILD). In certain embodiments, the autoimmune disease or disorder comprises graft vs. host disease (GvHD).

In one aspect, the disclosure provides the binding protein described above, for use as a medicament.

In one aspect, the disclosure provides the binding protein described above, for use in a method for the treatment of an autoimmune disease or disorder. In certain embodiments, the autoimmune disease or disorder comprises connective tissue disease-interstitial lung disease (CTD-ILD). In certain embodiments, the autoimmune disease or disorder comprises graft vs. host disease (GvHD).

In one aspect, the disclosure provides an antibody or antigen-binding fragment thereof that specifically binds to CD28, an immunoglobulin single variable domain (ISVD) comprising:

a)
an HCDR1 sequence comprising the amino acid sequence of GFTFSSYY (SEQ ID NO: 1),
an HCDR2 sequence comprising the amino acid sequence of INTDGFT (SEQ ID NO: 2), and
an HCDR3 sequence comprising the amino acid sequence of ARARGPYSRGSQGHDY (SEQ ID NO: 3); or b)
an HCDR1 sequence comprising the amino acid sequence of GSFFSIDT (SEQ ID NO: 13),
an HCDR2 sequence comprising the amino acid sequence of VTSGGLT (SEQ ID NO: 14), and
an HCDR3 sequence comprising the amino acid sequence of SARIRTSGGGWSTY (SEQ ID NO: 15).

In certain embodiments, the ISVD comprises an amino acid sequence that is at least about 90% identical to the amino acid sequence of SEQ ID NO: 10 or SEQ ID NO: 16.

In certain embodiments, the antibody or antigen-binding fragment thereof is a monoclonal antibody or antigen-binding fragment thereof.

In certain embodiments, the antibody or antigen-binding fragment thereof is a bispecific antibody.

In certain embodiments, the bispecific antibody comprises an antigen binding domain comprising binding affinity to OX40.

In certain embodiments, the antibody or antigen-binding fragment thereof is operatively linked to an Fc region. In certain embodiments, the Fc region is a human IgG1 Fc region.

In certain embodiments, the antibody or antigen-binding fragment thereof comprises an antagonistic antibody or antigen-binding fragment thereof.

In one aspect, the disclosure provides a pharmaceutical composition comprising the antibody or antigen-binding fragment thereof described above and a pharmaceutically acceptable carrier.

In one aspect, the disclosure provides an isolated nucleic acid molecule encoding the antibody or antigen-binding fragment thereof described above.

In one aspect, the disclosure provides an expression vector comprising the nucleic acid molecule described above.

In one aspect, the disclosure provides a host cell comprising the expression vector described above.

In one aspect, the disclosure provides a method for treating an autoimmune disease in a subject, comprising administering to a subject in need thereof the antibody or antigen-binding fragment thereof described above.

In one aspect, the disclosure provides the antibody or antigen-binding fragment thereof described above, for use as a medicament.

In one aspect, the disclosure provides the antibody or antigen-binding fragment thereof described above, for use in a method for the treatment or prevention of autoimmune disease.

In one aspect, the disclosure provides an antibody or antigen-binding fragment thereof that specifically binds to OX40, comprising an immunoglobulin single variable domain (ISVD) comprising:
a)
  (a1) an immunoglobulin heavy chain variable domain (VH) comprising
    an HCDR1 sequence comprising the amino acid sequence of GFTFSSYA (SEQ ID NO: 4),
    an HCDR2 sequence comprising the amino acid sequence of ISSQGGST (SEQ ID NO: 5), and
    an HCDR3 sequence comprising the amino acid sequence of ARGEAYWYRWAFDY (SEQ ID NO: 6); and
  (a2) an immunoglobulin light chain variable domain (VL) comprising
    an LCDR1 sequence comprising the amino acid sequence QSISSW (SEQ ID NO: 7),
    an LCDR2 sequence comprising the amino acid sequence of DAS (SEQ ID NO: 8), and
    an LCDR3 sequence comprising the amino acid sequence of QQYSDYSYT (SEQ ID NO: 9); or
b)
  (b1) an immunoglobulin heavy chain variable domain (VH) comprising
    an HCDR1 sequence comprising the amino acid sequence of GYTFTSYG (SEQ ID NO: 17),
    an HCDR2 sequence comprising the amino acid sequence of ISAYTGNT (SEQ ID NO: 18), and
    an HCDR3 sequence comprising the amino acid sequence of ARDGYPIDY (SEQ ID NO: 19); and
  (b2) an immunoglobulin light chain variable domain (VL) comprising
    an LCDR1 sequence comprising the amino acid sequence QSISSW (SEQ ID NO: 20),
    an LCDR2 sequence comprising the amino acid sequence of DAS (SEQ ID NO: 21), and
    an LCDR3 sequence comprising the amino acid sequence of QQYTSYSDT (SEQ ID NO: 22); or
c)
  (c1) an immunoglobulin heavy chain variable domain (VH) comprising
    an HCDR1 sequence comprising the amino acid sequence of GFTFSSYA (SEQ ID NO: 25),
    an HCDR2 sequence comprising the amino acid sequence of ISSQGGST (SEQ ID NO: 26), and
    an HCDR3 sequence comprising the amino acid sequence of ARGGSGWYNSEFDY (SEQ ID NO: 27); and
  (c2) an immunoglobulin light chain variable domain (VL) comprising
    an LCDR1 sequence comprising the amino acid sequence QSISSW (SEQ ID NO: 28),
    an LCDR2 sequence comprising the amino acid sequence of DAS (SEQ ID NO: 29), and
    an LCDR3 sequence comprising the amino acid sequence of QQYNDYSYT (SEQ ID NO: 30).

In certain embodiments, a) the VH comprises an amino acid sequence that is at least about 90% identical to the amino acid sequence of SEQ ID NO: 11 and the VL comprises an amino acid sequence that is at least about 90% identical to the amino acid sequence of SEQ ID NO: 12; b) the VH comprises an amino acid sequence that is at least about 90% identical to the amino acid sequence of SEQ ID NO: 23 and the VL comprises an amino acid sequence that is at least about 90% identical to the amino acid sequence of SEQ ID NO: 24; or c) the VH comprises an amino acid sequence that is at least about 90% identical to the amino acid sequence of SEQ ID NO: 31 and the VL comprises an amino acid sequence that is at least about 90% identical to the amino acid sequence of SEQ ID NO: 32.

In certain embodiments, the antibody or antigen-binding fragment thereof is a monoclonal antibody or antigen-binding fragment thereof.

In certain embodiments, the antibody or antigen-binding fragment thereof is a bispecific antibody.

In certain embodiments, the bispecific antibody comprises an antigen binding domain comprising binding affinity to CD28.

In certain embodiments, the antibody or antigen-binding fragment thereof is operatively linked to an Fc region.

In certain embodiments, the Fc region is a human IgG1 Fc region.

In certain embodiments, the antibody or antigen-binding fragment thereof comprises an antagonistic antibody or antigen-binding fragment thereof.

In one aspect, the disclosure provides a pharmaceutical composition comprising the antibody or antigen-binding fragment thereof described above and a pharmaceutically acceptable carrier.

In one aspect, the disclosure provides an isolated nucleic acid molecule encoding the antibody or antigen-binding fragment thereof described above.

In one aspect, the disclosure provides an expression vector comprising the nucleic acid molecule described above.

In one aspect, the disclosure provides a host cell comprising the expression vector described above.

In one aspect, the disclosure provides a method for treating an autoimmune disease in a subject, comprising administering to a subject in need thereof the antibody or antigen-binding fragment thereof described above.

In one aspect, the disclosure provides the antibody or antigen-binding fragment thereof described above, for use as a medicament.

In one aspect, the disclosure provides the antibody or antigen-binding fragment thereof described above, for use in a method for the treatment or prevention of autoimmune disease.

In certain embodiments, the antibody or antigen-binding fragment thereof described herein is administered intravenously to a subject in need thereof.

In certain embodiments, the antibody or antigen-binding fragment thereof described herein is administered intravenously to the subject at a dose of about 0.3 mg to about 30 mg.

In certain embodiments, the antibody or antigen-binding fragment thereof described herein is administered intravenously to the subject at a dose of about 0.3 mg. In certain embodiments, the antibody or antigen-binding fragment thereof described herein is administered intravenously to the subject at a dose of about 1 mg. In certain embodiments, the antibody or antigen-binding fragment thereof described herein is administered intravenously to the subject at a dose of about 3 mg. In certain embodiments, the antibody or antigen-binding fragment thereof described herein is administered intravenously to the subject at a dose of about 10 mg.

In certain embodiments, the antibody or antigen-binding fragment thereof described herein is administered intravenously to the subject at a dose of about 30 mg.

In certain embodiments, the antibody or antigen-binding fragment thereof described herein is administered subcutaneously to a subject in need thereof.

In certain embodiments, the antibody or antigen-binding fragment thereof described herein is administered subcutaneously to the subject at a dose of about 30 mg to about 500 mg.

In certain embodiments, the antibody or antigen-binding fragment thereof described herein is administered subcutaneously to the subject at a dose of about 30 mg. In certain embodiments, the antibody or antigen-binding fragment thereof described herein is administered subcutaneously to the subject at a dose of about 60 mg. In certain embodiments, the antibody or antigen-binding fragment thereof described herein is administered subcutaneously to the subject at a dose of about 75 mg. In certain embodiments, the antibody or antigen-binding fragment thereof described herein is administered subcutaneously to the subject at a dose of about 120 mg. In certain embodiments, the antibody or antigen-binding fragment thereof described herein is administered subcutaneously to the subject at a dose of about 150 mg. In certain embodiments, the antibody or antigen-binding fragment thereof described herein is administered subcutaneously to the subject at a dose of about 240 mg. In certain embodiments, the antibody or antigen-binding fragment thereof described herein is administered subcutaneously to the subject at a dose of about 300 mg. In certain embodiments, the antibody or antigen-binding fragment thereof described herein is administered subcutaneously to the subject at a dose of about 500 mg.

In certain embodiments, the antibody or antigen-binding fragment thereof described herein is administered subcutaneously to the subject at a dose of about 30 mg once every two weeks (Q2W). In certain embodiments, the antibody or antigen-binding fragment thereof described herein is administered subcutaneously to the subject at a dose of about 60 mg once every two weeks (Q2W). In certain embodiments, the antibody or antigen-binding fragment thereof described herein is administered subcutaneously to the subject at a dose of about 120 mg once every two weeks (Q2W). In certain embodiments, the antibody or antigen-binding fragment thereof described herein is administered subcutaneously to the subject at a dose of about 240 mg once every two weeks (Q2W).

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 6A depicts the high potency of the bispecific compounds on multiple pro-inflammatory cytokines in MLR assays.

In FIG. 9B, "aOX40" and "aCD28" correspond to monospecific controls.

FIG. 10 depicts the PK activity of exemplary bispecific antibodies.

Figure 14A:
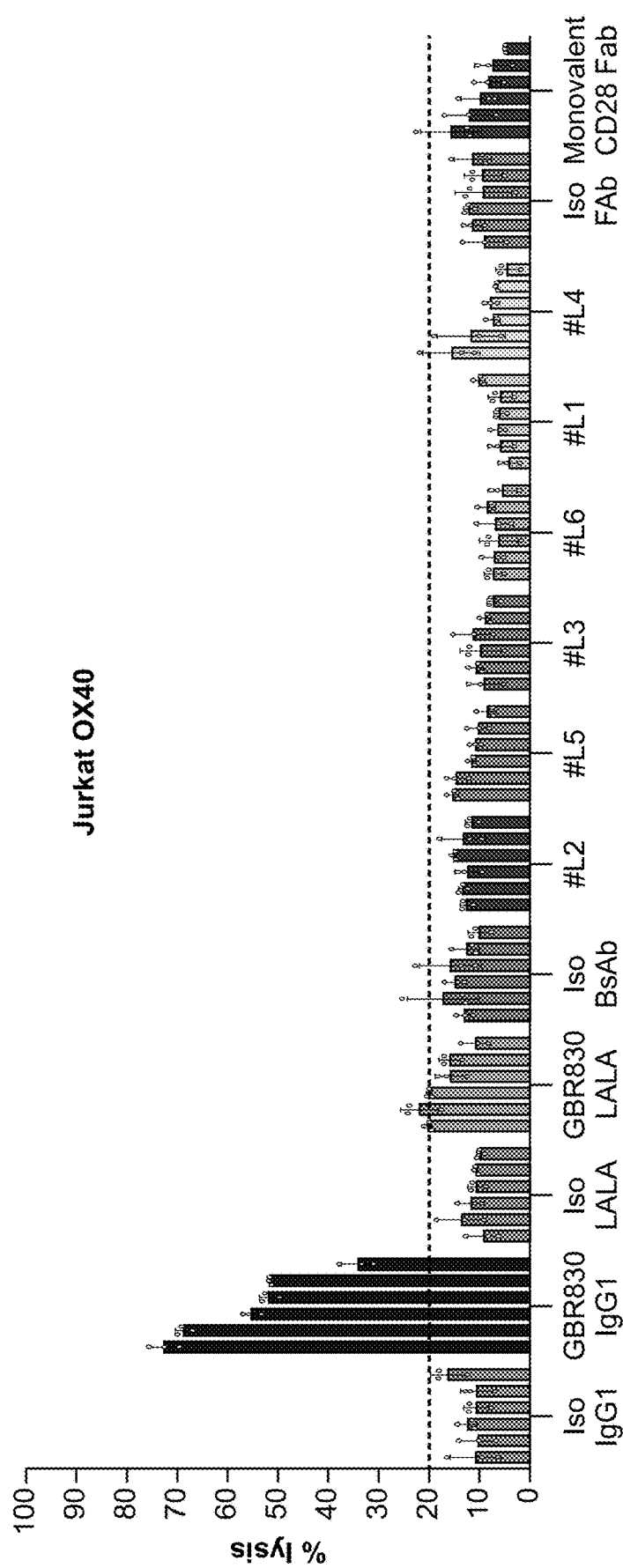
FIG. 14A and FIG. 14B depict the lack of detectable ADCC activity induced by the bispecific antibodies in Jurkat (FIG. 14A) and HEK293 (FIG. 14B) assay systems. FIG.
Figure 14B:
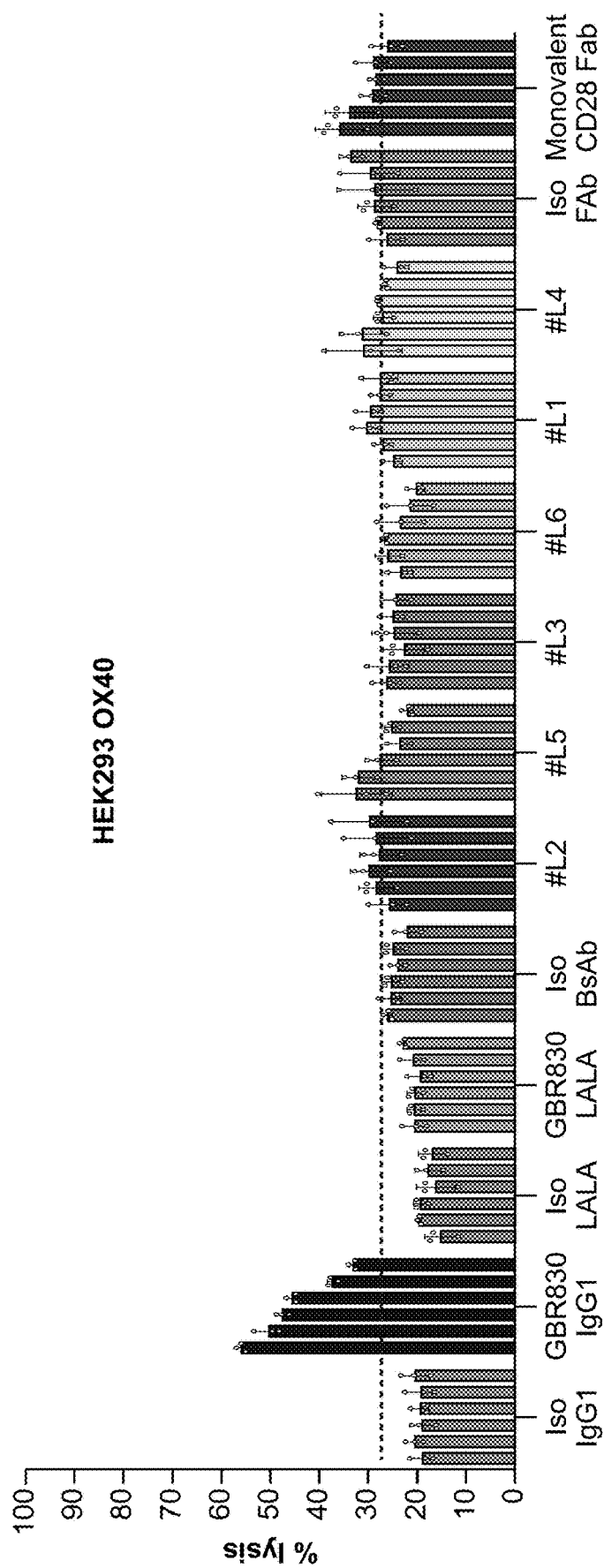
Figure 14C:
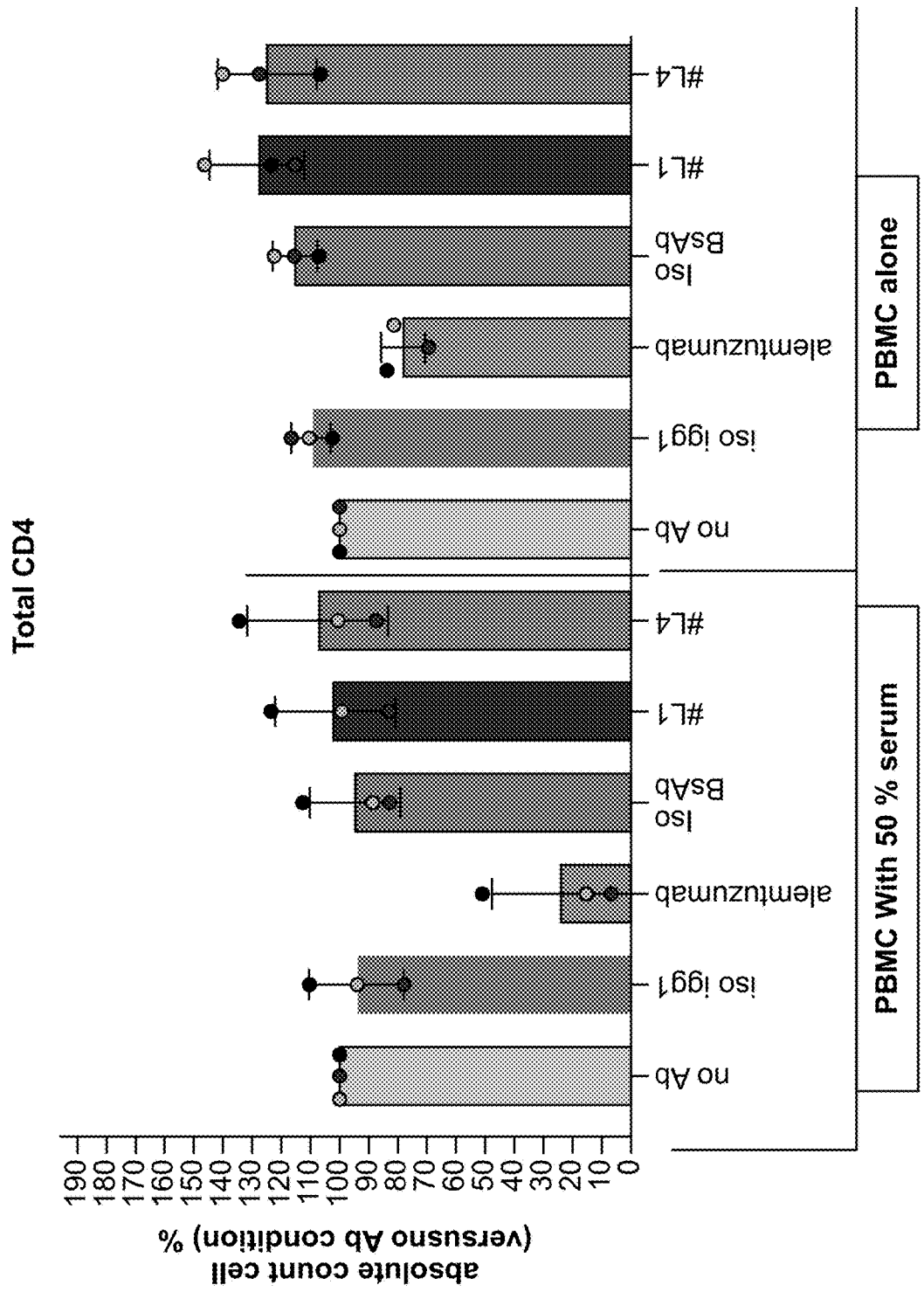
Figure 14D:
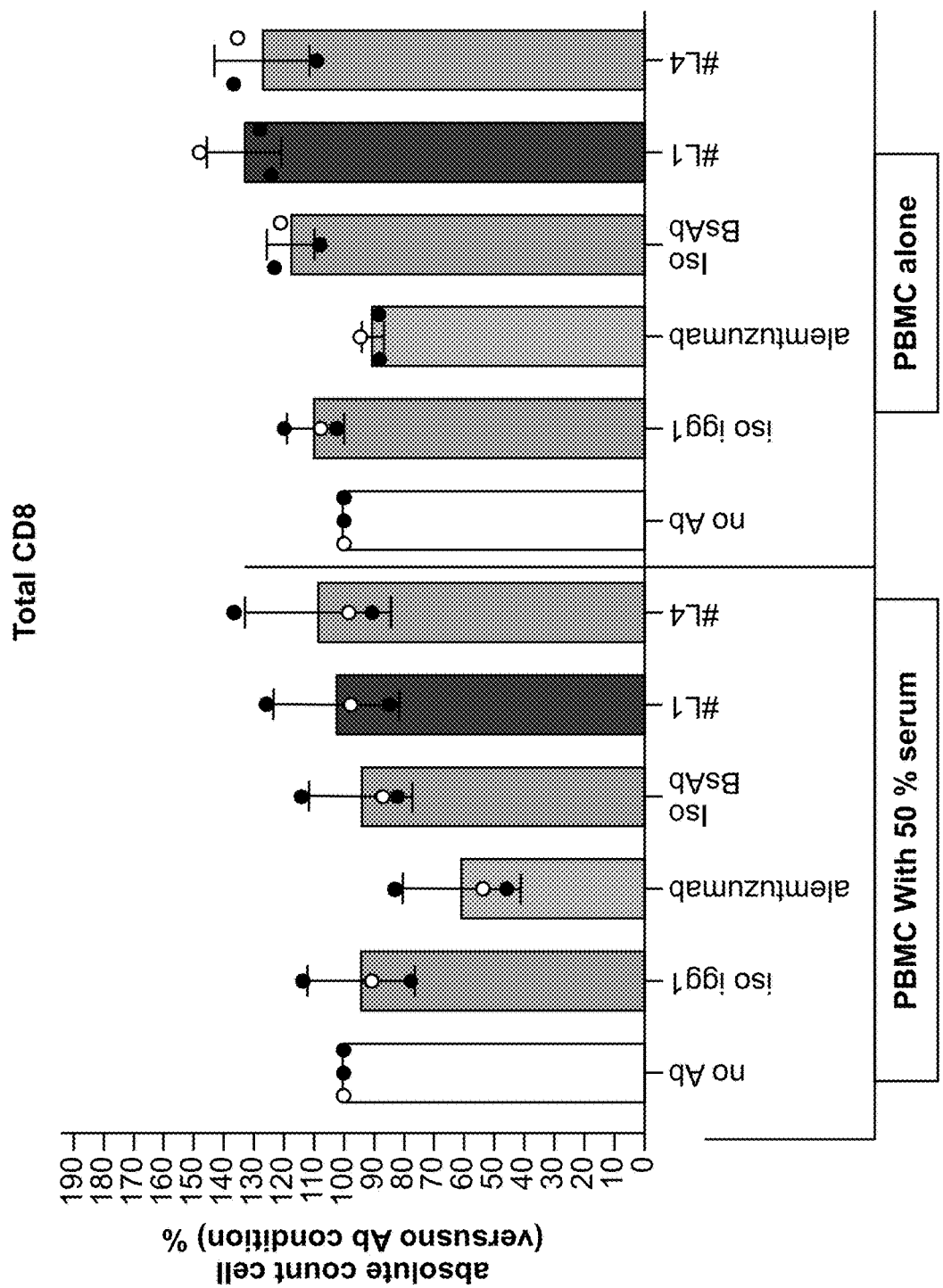

14C and FIG. 14D depict the lack of detectable CDC activity induced in CD4 and CD8 assay systems.

DETAILED DESCRIPTION

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can be used in the practice of the present disclosure, exemplary methods and materials are now described. All publications mentioned herein are incorporated herein by reference to describe in their entirety.

The term "about" or "approximately" means within about 20%, such as within about 10%, within about 5%, or within about 1% or less of a given value or range.

As used herein, the term "antibody" or "antigen-binding protein" refers to an immunoglobulin molecule that specifically binds to, or is immunologically reactive with an antigen or epitope, and includes both polyclonal and monoclonal antibodies, as well as functional antibody fragments thereof. The term "antibody" or "antigen-binding protein" includes immunoglobulin single variable domain (ISVD or ISV) antibodies (e.g., sdAb, sdFv, Nanobody®, VHH). The term "antibody" includes genetically engineered or otherwise modified forms of immunoglobulins, such as intrabodies, peptibodies, chimeric antibodies, fully human antibodies, humanized antibodies, meditope-enabled antibodies, heteroconjugate antibodies (e.g., multispecific antibodies, bispecific antibodies, diabodies, triabodies, tetrabodies, tandem di-scFv, tandem tri-scFv) and the like.

As used herein, the term "functional antibody fragment" refers to an antibody fragment having at least 80%, at least 85%, at least 90%, or at least 95% affinity as the antibody of interest from which the fragment is derived from.

The term "multispecific antibody" as used herein refers to bispecific, trispecific or multispecific antibodies, and antigen-binding fragments thereof. Multispecific antibodies may be specific for different epitopes of one target polypeptide or may contain antigen-binding domains specific for epitopes of more than one target polypeptide. A multispecific antibody can be a single multifunctional polypeptide, or it can be a multimeric complex of two or more polypeptides that are covalently or non-covalently associated with one another. The term "multispecific antibodies" includes antibodies of the present disclosure that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bispecific or a multispecific antibody with a second binding specificity.

As used herein, "monovalent" with reference to an antibody refers to antibodies that have a single antigen recognition site that is specific for a target antigen. Examples of monovalent antibodies include, a monovalent immunoglobulin single variable domain antibody (e.g., VHH) or a monovalent antibody fragment. Examples of monovalent antibody fragments include, but are not limited to, a Fab fragment, an Fv fragment, and a single-chain Fv fragment (scFv). Moreover, a multispecific antibody can have multiple antigen binding sites, each antigen binding site recognizing a different target antigen. Each antigen binding site would therefore be monovalent for the target antigen.

As used herein, "multivalent" with reference to an antibody refers to an antibody that has multiple (more than one) antigen recognition sites that are specific for a target antigen.

As used herein, the term "complementarity determining region" or "CDR" refers to sequences of amino acids within antibody variable regions, which confer antigen specificity and binding affinity. In general, there are three CDRs in each heavy chain variable region (HCDR1, HCDR2, HCDR3) and three CDRs in each light chain variable region (LCDR1, LCDR2, LCDR3). "Framework regions" or "FR" are known in the art to refer to the non-CDR portions of the variable regions of the heavy and light chains. In general, there are four FRs in each heavy chain variable region (FR-H1, FR-H2, FR-H3, and FR-H4), and four FRs in each light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745. ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, (AHo numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

A "CDR" or "complementarity determining region," or individual specified CDRs (e.g., "HCDR1," "HCDR2," "HCDR3"), of a given antibody or region thereof, such as a variable region thereof, should be understood to encompass a (or the specific) complementarity determining region as defined by any of the known schemes. Likewise, an "FR" or "framework region," or individual specified FRs (e.g., "FR-H1," "FR-H2") of a given antibody or region thereof, such as a variable region thereof, should be understood to encompass a (or the specific) framework region as defined by any of the known schemes. In some instances, the scheme for identification of a particular CDR or FR is specified, such as the CDR as defined by the IMGT, Kabat, Chothia, AbM, or Contact method. In other cases, the particular amino acid sequence of a CDR or FR is given. Unless otherwise specified, all particular CDR amino acid sequences mentioned in the disclosure are IMGT CDRs. However, alternative CDRs defined by other schemes are also encompassed by the present disclosure, such as those determined by abYsis Key Annotation (Website: abysis.org/abysis/sequence_input/key_annotation/key_annotation.cgi). Exemplary CDR sequences for anti-CD28 and anti-OX40 antibodies described herein are recited below in Table 1 and 2.

TABLE 1

Anti-CD28 VHH HCDR Amino Acid Sequences

| Sequence ID | Sequence |
|---|---|
| L4 & L6 & L5 CD28 HCDR1 SEQ ID NO: 1 | GFTFSSYY |
| L4 & L6 & L5 CD28 HCDR2 SEQ ID NO: 2 | INTDGDFT |
| L4 & L6 & L5 CD28 HCDR3 SEQ ID NO: 3 | ARARGPYSRGSQGHDY |
| L1 & L3 & L2 CD28 HCDR1 SEQ ID NO: 13 | GSFFSIDT |
| L1 & L3 & L2 CD28 HCDR2 SEQ ID NO: 14 | VTSGGLT |
| L1 & L3 & L2 CD28 HCDR3 SEQ ID NO: 15 | SARIRTSGGGWSTY |

TABLE 2

Anti-OX40 HCDR & LCDR Amino Acid Sequences

| Sequence ID | Sequence |
|---|---|
| L4 & L1 OX40 HCDR1 SEQ ID NO: 4 | GFTFSSYA |
| L4 & L1 OX40 HCDR2 SEQ ID NO: 5 | ISSQGGST |
| L4 & L1 OX40 HCDR3 SEQ ID NO: 6 | ARGEAYWYRWAFDY |
| L4 & L1 OX40 LCDR1 SEQ ID NO: 7 | QSISSW |
| L4 & L1 OX40 LCDR2 SEQ ID NO: 8 | DAS |
| L4 & L1 OX40 LCDR3 SEQ ID NO: 9 | QQYSDYSYT |
| L6 & L3 OX40 HCDR1 SEQ ID NO: 17 | GYTFTSYG |
| L6 & L3 OX40 HCDR2 SEQ ID NO: 18 | ISAYTGNT |
| L6 & L3 OX40 HCDR3 SEQ ID NO: 19 | ARDGYPIDY |
| L6 & L3 OX40 LCDR1 SEQ ID NO: 20 | QSISSW |
| L6 & L3 OX40 LCDR2 SEQ ID NO: 21 | DAS |
| L6 & L3 OX40 LCDR3 SEQ ID NO: 22 | QQYTSYSDT |
| L5 & L2 OX40 HCDR1 SEQ ID NO: 25 | GFTFSSYA |
| L5 & L2 OX40 HCDR2 SEQ ID NO: 26 | ISSQGGST |
| L5 & L2 OX40 HCDR3 SEQ ID NO: 27 | ARGGSGWYNSEFDY |
| L5 & L2 OX40 LCDR1 SEQ ID NO: 28 | QSISSW |
| L5 & L2 OX40 LCDR2 SEQ ID NO: 29 | DAS |
| L5 & L2 OX40 LCDR3 SEQ ID NO: 30 | QQYNDYSYT |
| Prototype OX40 HCDR1 SEQ ID NO: 97 | GFTFDDYT |
| Prototype OX40 HCDR2 SEQ ID NO: 98 | ISWDGGST |
| Prototype OX40 HCDR3 SEQ ID NO: 99 | ARDNLWGYLTYFDY |
| Prototype OX40 LCDR1 SEQ ID NO: 100 | SSNIGNNY |
| Prototype OX40 LCDR2 SEQ ID NO: 101 | DNN |
| Prototype OX40 LCDR3 SEQ ID NO: 102 | GTWDSSLTAYV |

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, llama, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. A humanized sequence can be identified by its primary sequence and does not necessarily denote the process by which the antibody was created.

As used herein, the term "specifically binds," "specifically binding," "binding specificity" or "specifically recognized" refers that an antigen binding protein or antigen-binding fragment thereof that exhibits appreciable affinity for an antigen (e.g., a CD28 antigen or an OX40 antigen) and does not exhibit significant cross reactivity to a target that is not a CD28 protein or OX40 protein. As used herein, the term "affinity" refers to the strength of the interaction between an antigen binding protein or antigen-binding fragment thereof antigen binding site and the epitope to which it binds. In certain exemplary embodiments, affinity is measured by surface plasmon resonance (SPR), e.g., in a Biacore instrument. As readily understood by those skilled in the art, an antigen binding protein affinity may be reported as a dissociation constant (KD) in molarity (M).

Specific binding can be determined according to any art-recognized means for determining such binding. In some embodiments, specific binding is determined by competitive binding assays (e.g., ELISA) or SPR (Biacore) assays. In certain embodiments, the assay is conducted at about 20° C., 25° C., 30° C., or 37° C.

The term "agonist" as used herein in reference to an antibody means that upon binding to the target protein expressed on the surface of a cell the antibody stimulates or activates signaling through the target protein.

The term "antagonist" as used herein in reference to an antibody means that upon binding to the target protein expressed on the surface of a cell the antibody inhibits signaling through the target protein.

As used herein, "administer" or "administration" refers to the act of injecting or otherwise physically delivering a substance as it exists outside the body (e.g., an antibody provided herein) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms. The route of administration may be intravenous administration. The route of administration may be subcutaneous administration.

"Effective amount" means the amount of active pharmaceutical agent (e.g., an isolated binding polypeptide of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sport animals, and pets. The subject may be human.

As used herein, the term "therapy" refers to any protocol, method and/or agent that can be used in the prevention, management, treatment and/or amelioration of a disease or a symptom related thereto. In some embodiments, the terms "therapies" and "therapy" refer to a biological therapy, supportive therapy, and/or other therapies useful in the prevention, management, treatment and/or amelioration of a disease or a symptom related thereto, known to one of skill in the art such as medical personnel.

As used herein, the terms "treat," "treatment" and "treating" refer to the reduction or amelioration of the progression, severity, and/or duration of a disease or a symptom related thereto, resulting from the administration of one or more therapies (including, but not limited to, the administration of one or more prophylactic or therapeutic agents, such as an isolated binding polypeptide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

As used herein, "autoimmune disease" refers to disease conditions and states wherein the immune response of an individual is directed against the individual's own constituents, resulting in an undesirable and often debilitating condition. As used herein, "autoimmune disease" is intended to further include autoimmune conditions, syndromes, and the like.

Immunoglobulin Single Variable Domain (ISVD)

The term "immunoglobulin single variable domain" (ISV or ISVD), interchangeably used with "single variable domain", defines immunoglobulin molecules wherein the antigen binding site is present on, and formed by, a single immunoglobulin domain. This sets immunoglobulin single variable domains apart from "conventional" immunoglobulins (e.g. monoclonal antibodies) or their fragments (such as Fab, Fab', F(ab')$_2$, scFv, di-scFv), wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody or of a Fab fragment, a F(ab')$_2$ fragment, an Fv fragment such as a disulfide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single $V_H$, a single $V_{HH}$ or single $V_L$ domain.

As such, the single variable domain may be a light chain variable domain sequence (e.g., a $V_L$-sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

An immunoglobulin single variable domain (ISV) can for example be a heavy chain ISV, such as a $V_H$, $V_{HH}$, including a camelized $V_H$ or humanized $V_{HH}$. In one embodiment, it is a $V_{HH}$, including a camelized $V_H$ or humanized $V_{HH}$. Heavy chain ISVs can be derived from a conventional four-chain antibody or from a heavy chain antibody.

For example, the immunoglobulin single variable domain may be a single domain antibody (or an amino acid sequence that is suitable for use as a single domain antibody), a "dAb" or dAb (or an amino acid sequence that is suitable for use as a dAb) or a Nanobody® ISV (as defined herein, and including but not limited to a $V_{HH}$); other single variable domains, or any suitable fragment of any one thereof.

In particular, the immunoglobulin single variable domain may be a Nanobody® ISV (such as a $V_{HH}$, including a humanized $V_{HH}$ or camelized $V_H$) or a suitable fragment thereof. [Note: Nanobody® and Nanobodies® are registered trademarks of Ablynx N.V.]

"$V_{HH}$ domains", also known as $V_{HH}$s, $V_{HH}$ antibody fragments, and $V_{HH}$ antibodies, have originally been described as the antigen binding immunoglobulin variable domain of "heavy chain antibodies" (i.e., of "antibodies devoid of light chains"; Hamers-Casterman et al. Nature 363: 446-448, 1993). The term "$V_{HH}$ domain" has been chosen in order to distinguish these variable domains from the heavy chain variable domains that are present in conventional 4-chain antibodies (which are referred to herein as "$V_H$ domains") and from the light chain variable domains that are present in conventional 4-chain antibodies (which are referred to herein as "VL domains"). For a further description of $V_{HH}$'S, reference is made to the review article by Muyldermans (Reviews in Molecular Biotechnology 74: 277-302, 2001).

The generation of immunoglobulin sequences, such as VHHs, has been described extensively in various publications, among which WO 94/04678, Hamers-Casterman et al. 1993 and Muyldermans et al. 2001 (Reviews in Molecular Biotechnology 74: 277-302, 2001). In these methods, camelids are immunized with the target antigen in order to induce an immune response against said target antigen. The repertoire of VHHs obtained from said immunization is further screened for VHHs that bind the target antigen.

In these instances, the generation of antibodies requires purified antigen for immunization and/or screening. Antigens can be purified from natural sources, or in the course of recombinant production. Immunization and/or screening for immunoglobulin sequences can be performed using peptide fragments of such antigens.

Immunoglobulin sequences of different origin, comprising mouse, rat, rabbit, donkey, human and camelid immunoglobulin sequences can be used herein. Also, fully human, humanized or chimeric sequences can be used in the method described herein. For example, camelid immunoglobulin sequences and humanized camelid immunoglobulin sequences, or camelized domain antibodies, e.g. camelized dAb as described by Ward et al (see for example WO 94/04678 and Riechmann, Febs Lett., 339:285-290, 1994 and Prot. Eng., 9:531-537, 1996) can be used herein. Moreover, the ISVs are fused forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221).

A "humanized $V_{HH}$" comprises an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the prior art (e.g. WO 2008/020079). Again, it should be noted that such humanized $V_{HH}$S can be obtained in any suitable manner known per se and thus are not strictly limited to polypeptides that have been obtained using a polypeptide that comprises a naturally occurring VHH domain as a starting material.

A "camelized $V_H$" comprises an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a (camelid) heavy chain antibody. This can be performed in a manner known per se, which will be clear to the skilled person, for example on the basis of the description in the prior art (e.g. Davies and Riechman (1994 and 1996), supra). Such "camelizing" substitutions are inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). In one embodiment, the $V_H$ sequence that is used as a starting material or starting point for generating or designing the camelized $V_H$ is a $V_H$ sequence from a mammal, such as the $V_H$ sequence of a human being, such as a $V_H$3 sequence. However, it should be noted that such camelized $V_H$ can be obtained in any suitable manner known per se and thus are not strictly limited to polypeptides that have been obtained using a polypeptide that comprises a naturally occurring $V_H$ domain as a starting material.

The structure of an immunoglobulin single variable domain sequence can be considered to be comprised of four framework regions ("FRs"), which are referred to in the art and herein as "Framework region 1" ("FR1"); as "Framework region 2" ("FR2"); as "Framework region 3" ("FR3"); and as "Framework region 4" ("FR4"), respectively; which framework regions are interrupted by three complementary determining regions ("CDRs"), which are referred to in the art and herein as "Complementarity Determining Region 1" ("CDR1"); as "Complementarity Determining Region 2" ("CDR2"); and as "Complementarity Determining Region 3" ("CDR3"), respectively.

In such an immunoglobulin sequence, the framework sequences may be any suitable framework sequences, and examples of suitable framework sequences will be clear to the skilled person, for example on the basis the standard handbooks and the further disclosure and prior art mentioned herein.

The framework sequences are (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence or $V_{HH}$ sequence). In one particular aspect, the framework sequences are either framework sequences that have been derived from a $V_{HH}$-sequence (in which said framework sequences may optionally have been partially or fully humanized) or are conventional $V_H$ sequences that have been camelized (as defined herein).

In particular, the framework sequences present in the ISV sequence described herein may contain one or more of hallmark residues (as defined herein), such that the ISV sequence is a Nanobody® ISV, such as e.g. a $V_{HH}$, including a humanized $V_{HH}$ or camelized $V_H$. Non-limiting examples of (suitable combinations of) such framework sequences will become clear from the further disclosure herein.

The total number of amino acid residues in a $V_H$ domain and a $V_{HH}$ domain will usually be in the range of from 110 to 120, often between 112 and 115. It should however be noted that smaller and longer sequences may also be suitable for the purposes described herein.

However, it should be noted that the ISVs described herein is not limited as to the origin of the ISV sequence (or of the nucleotide sequence used to express it), nor as to the way that the ISV sequence or nucleotide sequence is (or has been) generated or obtained. Thus, the ISV sequences may be naturally occurring sequences (from any suitable species) or synthetic or semi-synthetic sequences. In a specific but non-limiting aspect, the ISV sequence is a naturally occurring sequence (from any suitable species) or a synthetic or semi-synthetic sequence, including but not limited to "humanized" (as defined herein) immunoglobulin sequences (such as partially or fully humanized mouse or rabbit immunoglobulin sequences, and in particular partially or fully humanized $V_{HH}$ sequences), "camelized" (as defined herein) immunoglobulin sequences (and in particular camelized $V_H$ sequences), as well as ISVs that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

Similarly, nucleotide sequences may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

Generally, Nanobody® ISVs (in particular $V_{HH}$ sequences, including (partially) humanized $V_{HH}$ sequences and camelized $V_H$ sequences) can be characterized by the presence of one or more "Hallmark residues" (as described herein) in one or more of the framework sequences (again as further described herein). Thus, generally, a Nanobody® ISV can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody® ISV can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody® ISV can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

one or more of the amino acid residues at positions 11, 37, 44, 45, 47, 83, 84, 103, 104 and 108 according to the Kabat numbering are chosen from the Hallmark residues mentioned in Table A below.

TABLE A

Hallmark Residues in Nanobody ® ISVs

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| 44[8] | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$. |
| 45[8] | L | $L^{(2)}$, $R^{(3)}$, P, H, F, G, Q, S, E, T, Y, C, I, D, V; preferably $L^{(2)}$ or $R^{(3)}$ |
| 47[8] | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |
| 83 | R or K; usually R | R, $K^{(5)}$, T, E$^{(5)}$, Q, N, S, I, V, G, M, L, A, D, Y, H; preferably K or R; most preferably K |

TABLE A-continued

Hallmark Residues in Nanobody ® ISVs

| Position | Human V$_H$3 | Hallmark Residues |
|---|---|---|
| 84 | A, T, D; predominantly A | P$^{(5)}$, S, H, L, A, V, I, T, F, D, R, Y, N, Q, G, E; preferably P |
| 103 | W | W$^{(4)}$, R$^{(6)}$, G, S, K, A, M, Y, L, F, T, N, V, Q, P$^{(6)}$, E, C; preferably W |
| 104 | G | G, A, S, T, D, P, N, E, C, L; preferably G |
| 108 | L, M or T; predominantly L | Q, L$^{(7)}$, R, P, E, K, S, T, M, A, H; preferably Q or L$^{(7)}$ |

Notes:
In particular, but not exclusively, in combination with KERE (SEQ ID NO: 48) or KQRE (SEQ ID NO: 49) at positions 43-46. Usually as GLEW (SEQ ID NO: 50) at positions 44-47. Usually as KERE (SEQ ID NO: 48) or KQRE (SEQ ID NO: 49) at positions 43-46, e.g. as KEREL (SEQ ID NO: 51), KEREF (SEQ ID NO: 52), KQREL (SEQ ID NO: 53), KQREF (SEQ ID NO: 54), KEREG (SEQ ID NO: 55), KQREW (SEQ ID NO: 56) or KQREG (SEQ ID NO: 57) at positions 43-47. Alternatively, also sequences such as TERE (SEQ ID NO: 58) (for example TEREL (SEQ ID NO: 59)), TQRE (SEQ ID NO: 60) (for example TQREL (SEQ ID NO: 61)), KECE (SEQ ID NO: 62) (for example KECEL (SEQ ID NO: 63) or KECER (SEQ ID NO: 64)), KQCE (SEQ ID NO: 65) (for example KQCEL (SEQ ID NO: 66)), RERE (SEQ ID NO: 67) (for example REREG (SEQ ID NO: 68)), RQRE (SEQ ID NO: 69) (for example RQREL (SEQ ID NO: 70), RQREF (SEQ ID NO: 71) or RQREW (SEQ ID NO: 72)), QERE (SEQ ID NO: 73) (for example QEREG (SEQ ID NO: 74)), QQRE (SEQ ID NO: 75), (for example QQREW (SEQ ID NO: 76), QQREL (SEQ ID NO: 77) or QQREF (SEQ ID NO: 78)), KGRE (SEQ ID NO: 79) (for example KGREG (SEQ ID NO: 80)), KDRE (SEQ ID NO: 81) (for example KDREV (SEQ ID NO: 82)) are possible. Some other possible, but less preferred sequences include for example DECKL (SEQ ID NO: 83) and NVCEL (SEQ ID NO: 84). With both GLEW (SEQ ID NO: 50) at positions 44-47 and KERE (SEQ ID NO: 48) or KQRE (SEQ ID NO: 49) at positions 43-46. Often as KP or EP at positions 83-84 of naturally occurring V$_{HH}$ domains. In particular, but not exclusively, in combination with GLEW (SEQ ID NO: 50) at positions 44-47. With the proviso that when positions 44-47 are GLEW (SEQ ID NO: 50), position 108 is always Q in (non-humanized) V$_{HH}$ sequences that also contain a W at 103. The GLEW (SEQ ID NO: 50) group also contains GLEW (SEQ ID NO: 50)-like sequences at positions 44-47, such as for example GVEW (SEQ ID NO: 85), EPEW (SEQ ID NO: 86), GLER (SEQ ID NO: 87), DQEW (SEQ ID NO: 88), DLEW (SEQ ID NO: 89), GIEW (SEQ ID NO: 90), ELEW (SEQ ID NO: 91), GPEW (SEQ ID NO: 92), EWLP (SEQ ID NO: 93), GPER (SEQ ID NO: 94), GLER (SEQ ID NO: 95) and ELEW (SEQ ID NO: 96).

CD28

The term "CD28" as used herein refers to the transmembrane co-stimulatory signaling protein expressed on T-cells. CD28 is involved in T-cell activation, proliferation, cytokine production, and survival. An exemplary wild type human CD28 amino acid sequence can be found under NCBI Reference Sequence: NP_006130.1; and Uniprot Reference Number: P10747-1 v1.

As used herein, a "CD28-binding polypeptide" or an "anti-CD28 antibody" refers to any antigen-binding protein having at least one antigen-binding site that specifically binds to CD28. It encompasses antibodies in a divalent form (such as native immunoglobulin molecules or F(ab)'2 fragments) with two CD28-binding sites, as well as antibodies in a monovalent form which have a single CD28-binding site. Herein, a CD28-binding polypeptide typically is an immunoglobulin single variable domain (ISVD) antibody (e.g., VHH)-containing polypeptide having at least one immunoglobulin single variable domain (e.g., VHH domain) that specifically binds to CD28. In certain embodiments, the anti-CD28 antibody or antigen-binding fragment thereof comprises a VHH domain selected from any one of the VHH amino acid sequences of Table 3.

TABLE 3

Anti-CD28 VHH amino acid sequences.

| Sequence ID | Sequence |
|---|---|
| L4, L6 & L5 CD28 VHH SEQ ID NO: 10 | DVQLVESGGGVVQPGGSLRLSCAASGFTFSSY YMSWVRQAPGKGLEWVSTINTDGDFTSYADSV KGRFTISRDNAKNTLYLQMNSLRPEDTALYYC ARARGPYSRGSQGHDYRGQGTLVTVSS |
| L1 & L3 & L2 CD28 VHH SEQ ID NO: 16 | DVQLVESGGGVVQPGGSLRLSCAASGSFFSID TMDWYRQAPGKQRELVTGVTSGGLTNYADSVK GRFTISIDNAKNTVYLQMNSLRPEDTALYYCS ARIRTSGGGWSTYWGQGTLVTVSS |

The CD28-binding polypeptides provided herein include monovalent and multivalent (e.g., bivalent) constructs. In some embodiments, a CD28-binding polypeptide provided herein contains one or two immunoglobulin single variable domains (e.g., VHH domains) that each individually binds CD28.

In certain embodiments, the anti-CD28 antibody or antigen-binding fragment thereof comprises a VHH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 10 or SEQ ID NO: 16.

In certain embodiments, the anti-CD28 antibody or antigen-binding fragment thereof comprises a VHH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 10. In certain embodiments, the anti-CD28 antibody or antigen-binding fragment thereof comprises a VHH domain as depicted in SEQ ID NO: 10.

In certain embodiments, the anti-CD28 antibody or antigen-binding fragment thereof comprises a VHH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 16. In certain embodiments, the anti-CD28 antibody or antigen-binding fragment thereof comprises a VHH domain as depicted in SEQ ID NO: 16.

In certain embodiments, the anti-CD28 antibody or antigen-binding fragment thereof comprises a HCDR1 region, a HCDR2 region, and a HCDR3 region that are at least about 90%, at least 91%, at least 92%, at least 93%, at least 94%, at least 95%, at least 96%, at least 97%, at least 98%, at least 99% or more identical to any one of the HCDR1, HCDR2, or HCDR3 amino acid sequences recited in Table 1.

In certain embodiments, the anti-CD28 antibody or antigen-binding fragment thereof comprises a HCDR1 region, a HCDR2 region, and a HCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 1, SEQ ID NO: 2, and SEQ ID NO: 3. In certain embodiments, the anti-CD28 antibody or antigen-binding fragment thereof comprises a HCDR1 region, a HCDR2 region, and a HCDR3 region as depicted in SEQ ID NO: 1, SEQ ID NO: 2, and SEQ ID NO: 3.

In certain embodiments, the anti-CD28 antibody or antigen-binding fragment thereof comprises a HCDR1 region, a HCDR2 region, and a HCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 13, SEQ ID NO: 14, and SEQ ID NO: 15. In certain embodiments, the anti-CD28 antibody or antigen-binding fragment thereof comprises a HCDR1 region, a HCDR2 region, and a HCDR3 region as depicted in SEQ ID NO: 13, SEQ ID NO: 14, and SEQ ID NO: 15.

In certain embodiments, the anti-CD28 antibody or antigen-binding fragment thereof comprises a VHH domain that is at least about 90%, at least 91%, at least 92%, at least 93%, at least 94%, at least 95%, at least 96%, at least 97%, at least 98%, at least 99% or more identical to the amino acid sequence of SEQ ID NO: 10 and further comprising a HCDR1 region, a HCDR2 region, and a HCDR3 region as depicted in SEQ ID NO: 1, SEQ ID NO: 2, and SEQ ID NO: 3 (i.e., a VHH domain at least about 90%, at least 91%, at least 92%, at least 93%, at least 94%, at least 95%, at least 96%, at least 97%, at least 98%, or at least 99% identical to SEQ ID NO: 10 outside of the HCDR1, HCDR2, and HCDR3 regions of SEQ ID NO: 1-3, respectively).

In certain embodiments, the anti-CD28 antibody or antigen-binding fragment thereof comprises a VHH domain that is at least about 90%, at least 91%, at least 92%, at least 93%, at least 94%, at least 95%, at least 96%, at least 97%, at least 98%, at least 99% or more identical to the amino acid sequence of SEQ ID NO: 16 and further comprising a HCDR1 region, a HCDR2 region, and a HCDR3 region as depicted in SEQ ID NO: 13, SEQ ID NO: 14, and SEQ ID NO: 15 (i.e., a VHH domain at least about 90%, at least 91%, at least 92%, at least 93%, at least 94%, at least 95%, at least 96%, at least 97%, at least 98%, or at least 99% identical to SEQ ID NO: 16 outside of the HCDR1, HCDR2, and HCDR3 regions of SEQ ID NO: 13-15, respectively).

In certain embodiments, the anti-CD28 antibody or antigen-binding fragment thereof is a chimeric or humanized antibody or antigen-binding fragment thereof.

In certain embodiments, the anti-CD28 antibody or antigen-binding fragment thereof is a monoclonal antibody or antigen-binding fragment thereof.

In certain embodiments, the anti-CD28 antibody or antigen-binding fragment thereof is a monospecific antibody.

In certain embodiments, the anti-CD28 antibody or antigen-binding fragment thereof is a bispecific antibody.

In certain embodiments, the anti-CD28 antibody or antigen-binding fragment thereof is a multispecific antibody. In an embodiment, the multispecific antibody comprises at least one Fab domain. In certain embodiments, the VH and VL domains of the Fab are replaced with any one of the VHH amino acid sequences of SEQ ID NO: 10 or SEQ ID NO: 16. In an embodiment, the multispecific antibody comprises at least one Fab domain. In certain embodiments, the VH and VL domains of the Fab are replaced with any one of the VHH amino acid sequences of SEQ ID NO: 10. In an embodiment, the multispecific antibody comprises at least one Fab domain. In certain embodiments, the VH and VL domains of the Fab are replaced with any one of the VHH amino acid sequences of SEQ ID NO: 16. The Fab domain may serve as a specific heterodimerization scaffold to which additional binding domains may be linked. Additional binding domains may be in several different formats, including, but not limited to, another Fab domain, a scFv, or an sdAb (e.g., VHH).

In one aspect, the disclosure provides an anti-CD28 antibody or antigen-binding fragment thereof comprising a VHH domain, wherein the VHH domain binds one or more of amino acids E32, E46, V47, C48, Y51, G52, N53, S55, Q57, L58, Q59, V60, Y61, S62, K63, T64, N67, C68, and D69 of SEQ ID NO: 46. In certain embodiments, the VHH domain binds amino acids E32, E46, V47, C48, Y51, G52, N53, S55, Q57, L58, Q59, V60, Y61, S62, K63, T64, N67, C68, and D69 of SEQ ID NO: 46. In certain embodiments, the anti-CD28 antibody or antigen-binding fragment thereof comprises a HCDR1 region, a HCDR2 region, and a HCDR3 region as depicted in SEQ ID NO: 1, SEQ ID NO: 2, and SEQ ID NO: 3. In certain embodiments, the anti-CD28 antibody or antigen-binding fragment thereof comprises a VHH domain as depicted in SEQ ID NO: 10.

In certain embodiments, the anti-CD28 antibody or antigen-binding fragment thereof comprises a VHH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 10, wherein the VHH domain comprises amino acids Y33, W47, T50, N52, D56, F57, T58, S59, K65, P102, Y103, S104, and R105 (positions according to numbering of SEQ ID NO: 10).

In certain embodiments, the anti-CD28 antibody or antigen-binding fragment thereof comprises a VHH domain comprising a HCDR1 region, a HCDR2 region, and a HCDR3 region as depicted in SEQ ID NO: 1, SEQ ID NO: 2, and SEQ ID NO: 3, wherein the VHH domain comprises amino acids W47, T50, S59, and K65 (positions according to numbering of SEQ ID NO: 10).

OX40

The term "OX40" as used herein refers to a member of the tumor necrosis factor receptor superfamily that acts as secondary co-stimulatory immune checkpoint molecule on the surface of T cells. An exemplary wild type human OX40 amino acid sequence can be found under NCBI Reference Sequence: NP_001397638.1; and Uniprot Reference Number: P43489 v1.

As used herein, a "OX40-binding polypeptide" or an "anti-OX40 antibody" refers to any antigen-binding protein having at least one antigen-binding site that specifically binds to OX40. It encompasses antibodies in a divalent form (such as native immunoglobulin molecules or F(ab)'2 fragments) with two OX40-binding sites, as well as antibodies in a monovalent form which have a single OX40-binding site. Herein, a OX40-binding polypeptide typically is a VH/VL pairing that specifically binds to OX40. In certain embodiments, the anti-OX40 antibody or antigen-binding fragment thereof comprises a VH and VL domain selected from any one of the VH and VL amino acid sequences of Table 4.

TABLE 4

Anti-OX40 VH and VL amino acid sequences.

| Sequence ID | Sequence |
|---|---|
| L4 & L1 OX40 VH SEQ ID NO: 11 | EVQLVESGGGLVQPGGSLRLSCAASGFTFSSY AMHWVRQAPGKGLEYVSAISSQGGSTYYANSV KGRFTISRDNSKNTLYLQMGSLRAEDTAVYYC ARGEAYWYRWAFDYWGQGTLVTVSS |

TABLE 4-continued

Anti-OX40 VH and VL amino acid sequences.

| Sequence ID | Sequence |
|---|---|
| L4 & L1<br>OX40 VL<br>SEQ ID NO: 12 | DIQMTQSPSTLSASVGDRVTITCRASQSISSW<br>LAWYQQKPGKAPKLLIYDASSLESGVPSRFSG<br>SGSGTEFTLTISSLQPDDFATYYCQQYSDYSY<br>TFGQGTKVEIK |
| L6 & L3<br>OX40 VH<br>SEQ ID NO: 23 | QVQLVQSGAEVKKPGASVKVSCKASGYTFTSY<br>GISWVRQAPGQGLEWMGWISAYTGNTNYAQKL<br>QGRVTMTTDTSTSTAYMELRSLRSDDTAVYYC<br>ARDGYPIDYWGQGTLVTVSS |
| L6 & L3<br>OX40 VL<br>SEQ ID NO: 24 | DIQMTQSPSTLSASVGDRVTITCRASQSISSW<br>LAWYQQKPGKAPKLLIYDASSLESGVPSRFSG<br>SGSGTEFTLTISSLQPDDFATYYCQQYTSYSD<br>TFGQGTKVEIK |
| L5 & L2<br>OX40 VH<br>SEQ ID NO: 31 | EVQLVESGGGLVQPGGSLRLSCAASGFTFSSY<br>AMHWVRQAPGKGLEYVSAISSQGGSTYYANSV<br>KGRFTISRDNSKNTLYLQMGSLRAEDTAVYYC<br>ARGGSGWYNSEFDYWGQGTLVTVSS |
| L5 & L2<br>OX40 VL<br>SEQ ID NO: 32 | DIQMTQSPSTLSASVGDRVTITCRASQSISSW<br>LAWYQQKPGKAPKLLIYDASSLESGVPSRFSG<br>SGSGTEFTLTISSLQPDDFATYYCQQYNDYSY<br>TFGQGTKVEIK |
| Prototype OX40 VH<br>SEQ ID NO: 103 | EVQLVESGGVVVQPGGSLRLSCAASGFTFDDY<br>TMHWVRQAPGKGLEWVSLISWDGGSTYYADSV<br>KGRFTISRDNSKNSLYLQMNSLRTEDTAVYYC<br>ARDNLWGYLTYFDYWGQGTLVTVSS |
| Prototype OX40 VL<br>SEQ ID NO: 104 | QSVLTQPPSVSAAPGQKVTISCSGSSSNIGNN<br>YVSWYQQLPGTAPKLLIYDNNKRPSGIPDRFS<br>GSKSGTSATLGITGLQTGDEADYYCGTWDSSL<br>TAYVFGGGTKLTVL |

The OX40-binding polypeptides provided herein include monovalent and multivalent (e.g., bivalent) constructs. In some embodiments, a OX40-binding polypeptide provided herein contains a VH and VL domain that form the antigen binding domain that binds OX40.

In certain embodiments, the anti-OX40 antibody or antigen-binding fragment thereof comprises a VL domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 12, SEQ ID NO: 24, or SEQ ID NO: 32.

In certain embodiments, the anti-OX40 antibody or antigen-binding fragment thereof comprises a VL domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 12. In certain embodiments, the anti-OX40 antibody or antigen-binding fragment thereof comprises a VL domain as depicted in SEQ ID NO: 12.

In certain embodiments, the anti-OX40 antibody or antigen-binding fragment thereof comprises a VL domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 24. In certain embodiments, the anti-OX40 antibody or antigen-binding fragment thereof comprises a VL domain as depicted in SEQ ID NO: 24.

In certain embodiments, the anti-OX40 antibody or antigen-binding fragment thereof comprises a VL domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 32. In certain embodiments, the anti-OX40 antibody or antigen-binding fragment thereof comprises a VL domain as depicted in SEQ ID NO: 32.

In certain embodiments, the anti-OX40 antibody or antigen-binding fragment thereof comprises a VH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 11, SEQ ID NO: 23, or SEQ ID NO: 31.

In certain embodiments, the anti-OX40 antibody or antigen-binding fragment thereof comprises a VH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 11. In certain embodiments, the anti-OX40 antibody or antigen-binding fragment thereof comprises a VH domain as depicted in SEQ ID NO: 11.

In certain embodiments, the anti-OX40 antibody or antigen-binding fragment thereof comprises a VH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 23. In certain embodiments, the anti-OX40 antibody or antigen-binding fragment thereof comprises a VH domain as depicted in SEQ ID NO: 23.

In certain embodiments, the anti-OX40 antibody or antigen-binding fragment thereof comprises a VH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 31. In certain embodiments, the anti-OX40 antibody or antigen-binding fragment thereof comprises a VH domain as depicted in SEQ ID NO: 31.

In certain embodiments, the anti-OX40 antibody or antigen-binding fragment thereof comprises a VH domain as depicted in SEQ ID NO: 11 and a VL domain as depicted in SEQ ID NO: 12.

In certain embodiments, the anti-OX40 antibody or antigen-binding fragment thereof comprises a VH domain as depicted in SEQ ID NO: 23 and a VL domain as depicted in SEQ ID NO: 24.

In certain embodiments, the anti-OX40 antibody or antigen-binding fragment thereof comprises a VH domain as depicted in SEQ ID NO: 31 and a VL domain as depicted in SEQ ID NO: 32.

In certain embodiments, the anti-OX40 antibody or antigen-binding fragment thereof comprises a HCDR1 region, a HCDR2 region, and a HCDR3 region that are at least about 90%, at least 91%, at least 92%, at least 93%, at least 94%, at least 95%, at least 96%, at least 97%, at least 98%, at least 99% or more identical to any one of the HCDR1, HCDR2, or HCDR3 amino acid sequences recited in Table 2.

In certain embodiments, the anti-OX40 antibody or antigen-binding fragment thereof comprises a HCDR1 region, a HCDR2 region, and a HCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 4, SEQ ID NO: 5, and SEQ ID NO: 6. In certain embodiments, the anti-OX40 antibody or antigen-binding fragment thereof comprises a HCDR1 region, a HCDR2 region, and a HCDR3 region as depicted in SEQ ID NO: 4, SEQ ID NO: 5, and SEQ ID NO: 6.

In certain embodiments, the anti-OX40 antibody or antigen-binding fragment thereof comprises a HCDR1 region, a HCDR2 region, and a HCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 17, SEQ ID NO: 18, and SEQ ID NO: 19. In certain embodiments, the anti-OX40 antibody or antigen-binding fragment thereof comprises a HCDR1 region, a HCDR2 region, and a HCDR3 region as depicted in SEQ ID NO: 17, SEQ ID NO: 18, and SEQ ID NO: 19.

In certain embodiments, the anti-OX40 antibody or antigen-binding fragment thereof comprises a HCDR1 region, a HCDR2 region, and a HCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 25, SEQ ID NO: 26, and SEQ ID NO: 27. In certain embodiments, the anti-OX40 antibody or antigen-binding fragment thereof comprises a HCDR1 region, a HCDR2 region, and a HCDR3 region as depicted in SEQ ID NO: 25, SEQ ID NO: 26, and SEQ ID NO: 27.

In certain embodiments, the anti-OX40 antibody or antigen-binding fragment thereof comprises a LCDR1 region, a LCDR2 region, and a LCDR3 region that are at least about 90%, at least 91%, at least 92%, at least 93%, at least 94%, at least 95%, at least 96%, at least 97%, at least 98%, at least 99% or more identical to any one of the LCDR1, LCDR2, or LCDR3 amino acid sequences recited in Table 2.

In certain embodiments, the anti-OX40 antibody or antigen-binding fragment thereof comprises a LCDR1 region, a LCDR2 region, and a LCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 7, SEQ ID NO: 8, and SEQ ID NO: 9. In certain embodiments, the anti-OX40 antibody or antigen-binding fragment thereof comprises a LCDR1 region, a LCDR2 region, and a LCDR3 region as depicted in SEQ ID NO: 7, SEQ ID NO: 8, and SEQ ID NO: 9.

In certain embodiments, the anti-OX40 antibody or antigen-binding fragment thereof comprises a LCDR1 region, a LCDR2 region, and a LCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 20, SEQ ID NO: 21, and SEQ ID NO: 22. In certain embodiments, the anti-OX40 antibody or antigen-binding fragment thereof comprises a LCDR1 region, a LCDR2 region, and a LCDR3 region as depicted in SEQ ID NO: 20, SEQ ID NO: 21, and SEQ ID NO: 22.

In certain embodiments, the anti-OX40 antibody or antigen-binding fragment thereof comprises a LCDR1 region, a LCDR2 region, and a LCDR3 region that are at least about 90%, at least 91%, at least 92%, at least 93%, at least 94%, at least 95%, at least 96%, at least 97%, at least 98%, at least 99% or more identical to the amino acid sequences of SEQ ID NO: 28, SEQ ID NO: 29, and SEQ ID NO: 30. In certain embodiments, the anti-OX40 antibody or antigen-binding fragment thereof comprises a LCDR1 region, a LCDR2 region, and a LCDR3 region as depicted in SEQ ID NO: 28, SEQ ID NO: 29, and SEQ ID NO: 30.

In certain embodiments, the anti-OX40 antibody or antigen-binding fragment thereof comprises a VH domain that is at least about 90%, at least 91%, at least 92%, at least 93%, at least 94%, at least 95%, at least 96%, at least 97%, at least 98%, at least 99% or more identical to the amino acid sequence of SEQ ID NO: 11 and further comprising a HCDR1 region, a HCDR2 region, and a HCDR3 region as depicted in SEQ ID NO: 4, SEQ ID NO: 5, and SEQ ID NO: 6; and a VL domain that is at least about 90%, at least 91%, at least 92%, at least 93%, at least 94%, at least 95%, at least 96%, at least 97%, at least 98%, at least 99% or more identical to the amino acid sequence of SEQ ID NO: 12 and further comprising a LCDR1 region, a LCDR2 region, and a LCDR3 region as depicted in SEQ ID NO: 7, SEQ ID NO: 8, and SEQ ID NO: 9.

In certain embodiments, the anti-OX40 antibody or antigen-binding fragment thereof comprises a VH domain that is at least about 90%, at least 91%, at least 92%, at least 93%, at least 94%, at least 95%, at least 96%, at least 97%, at least 98%, at least 99% or more identical to the amino acid sequence of SEQ ID NO: 23 and further comprising a HCDR1 region, a HCDR2 region, and a HCDR3 region as depicted in SEQ ID NO: 17, SEQ ID NO: 18, and SEQ ID NO: 19; and a VL domain that is at least about 90%, at least 91%, at least 92%, at least 93%, at least 94%, at least 95%, at least 96%, at least 97%, at least 98%, at least 99% or more identical to the amino acid sequence of SEQ ID NO: 24 and further comprising a LCDR1 region, a LCDR2 region, and a LCDR3 region as depicted in SEQ ID NO: 20, SEQ ID NO: 21, and SEQ ID NO: 22.

In certain embodiments, the anti-OX40 antibody or antigen-binding fragment thereof comprises a VH domain that is at least about 90%, at least 91%, at least 92%, at least 93%, at least 94%, at least 95%, at least 96%, at least 97%, at least 98%, at least 99% or more identical to the amino acid sequence of SEQ ID NO: 31 and further comprising a HCDR1 region, a HCDR2 region, and a HCDR3 region as depicted in SEQ ID NO: 25, SEQ ID NO: 26, and SEQ ID NO: 27; and a VL domain that is at least about 90%, at least 91%, at least 92%, at least 93%, at least 94%, at least 95%, at least 96%, at least 97%, at least 98%, at least 99% or more identical to the amino acid sequence of SEQ ID NO: 32 and further comprising a LCDR1 region, a LCDR2 region, and a LCDR3 region as depicted in SEQ ID NO: 28, SEQ ID NO: 29, and SEQ ID NO: 30.

In certain embodiments, the anti-OX40 antibody or antigen-binding fragment thereof is a chimeric or humanized antibody or antigen-binding fragment thereof.

In certain embodiments, the anti-OX40 antibody or antigen-binding fragment thereof is a monoclonal antibody or antigen-binding fragment thereof.

In certain embodiments, the anti-OX40 antibody or antigen-binding fragment thereof is a monospecific antibody.

In certain embodiments, the anti-OX40 antibody or antigen-binding fragment thereof is a bispecific antibody.

In certain embodiments, the anti-OX40 antibody or antigen-binding fragment thereof is a multispecific antibody.

In an embodiment, the multispecific antibody comprises at least one Fab domain. In certain embodiments, the VH of the Fab comprises an amino acid sequence of SEQ ID NO: 11 and the VL of the Fab comprises an amino acid sequence of SEQ ID NO: 12. In certain embodiments, the VH of the Fab comprises an amino acid sequence of SEQ ID NO: 23 and the VL of the Fab comprises an amino acid sequence of SEQ ID NO: 24. In certain embodiments, the VH of the Fab comprises an amino acid sequence of SEQ ID NO: 31 and the VL of the Fab comprises an amino acid sequence of SEQ ID NO: 32. The Fab domain may serve as a specific heterodimerization scaffold to which additional binding domains may be linked. Additional binding domains may be in several different formats, including, but not limited to, another Fab domain, a scFv, or an sdAb (e.g., VHH).

In one aspect, the disclosure provides an anti-OX40 antibody or antigen-binding fragment thereof comprising a VH domain and a VL domain, wherein the anti-OX40 antibody or antigen-binding fragment thereof binds one or more of amino acids H13, E14, C15, R16, P17, G18, N19, T31, V32, C33, R34, P35, C36, G37, P38, G39, F40, Y41, V45, L67, C68, T69, A70, and T71 of SEQ ID NO: 47. In certain embodiments, the anti-OX40 antibody or antigen-binding fragment thereof binds amino acids H13, E14, C15, R16, P17, G18, N19, T31, V32, C33, R34, P35, C36, G37, P38, G39, F40, Y41, V45, L67, C68, T69, A70, and T71 of SEQ ID NO: 47. In one aspect, the disclosure provides an anti-OX40 antibody or antigen-binding fragment thereof comprising a VH domain and a VL domain, wherein the anti-OX40 antibody or antigen-binding fragment thereof binds one or more of amino acids V22, C33, R34, P35, C36, G37, P38, G39, F40, P49, C50, C53, W55, R64, L67, C68, T69, and A70 of SEQ ID NO: 47. In certain embodiments, the anti-OX40 antibody or antigen-binding fragment thereof binds amino acids V22, C33, R34, P35, C36, G37, P38, G39, F40, P49, C50, C53, W55, R64, L67, C68, T69, and A70 of SEQ ID NO: 47. In certain embodiments, the anti-OX40 antibody or antigen-binding fragment thereof comprises a HCDR1 region, a HCDR2 region, and a HCDR3 region as depicted in SEQ ID NO: 4, SEQ ID NO: 5, and SEQ ID NO: 6, and a LCDR1 region, a LCDR2 region, and a LCDR3 region as depicted in SEQ ID NO: 7, SEQ ID NO: 8, and SEQ ID NO: 9. In certain embodiments, the anti-OX40 antibody or antigen-binding fragment thereof comprises a VH domain of SEQ ID NO: 11 and a VL domain of SEQ ID NO: 12.

In certain embodiments, the anti-OX40 antibody or antigen-binding fragment thereof comprises (i) a VH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 11, wherein the VH domain comprises amino acids H35, S52, Q54, G56, S57, T58, Y59, Y102, Y104, R105, and W106 (positions according to numbering of SEQ ID NO: 11), and (ii) a VL domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 12, wherein the VL domain comprises amino acids W32, D50, and S92 (positions according to numbering of SEQ ID NO: 12).

In certain embodiments, the anti-OX40 antibody or antigen-binding fragment thereof comprises (i) a VH domain comprising a HCDR1 region, a HCDR2 region, and a HCDR3 region as depicted in SEQ ID NO: 4, SEQ ID NO: 5, and SEQ ID NO: 6, and (ii) a VL domain comprising a LCDR1 region, a LCDR2 region, and a LCDR3 region as depicted in SEQ ID NO: 7, SEQ ID NO: 8, and SEQ ID NO: 9, wherein the VH domain comprises amino acids H35 and Y59 (positions according to numbering of SEQ ID NO: 11). In certain embodiments, the VL domain comprises the amino acid sequence of SEQ ID NO: 12.

In one aspect, the disclosure provides an anti-OX40 antibody or antigen-binding fragment thereof comprising a VH domain and a VL domain, wherein the anti-OX40 antibody or antigen-binding fragment thereof binds one or more amino acids to one or more amino acids R16, N19, V22, V32, C33, R34, P35, C36, G37, P38, G39, F40, P49, C50, C53, T54, W55, C56, R64, L67, C68, T69, A70, and T74 of SEQ ID NO: 47. In certain embodiments, the anti-OX40 antibody or antigen-binding fragment thereof binds to amino acids R16, N19, V22, V32, C33, R34, P35, C36, G37, P38, G39, F40, P49, C50, C53, T54, W55, C56, R64, L67, C68, T69, A70, and T74 of SEQ ID NO: 47.

In certain embodiments, the anti-OX40 antibody or antigen-binding fragment thereof comprises a HCDR1 region, a HCDR2 region, and a HCDR3 region as depicted in SEQ ID NO: 25, SEQ ID NO: 26, and SEQ ID NO: 27, and a LCDR1 region, a LCDR2 region, and a LCDR3 region as depicted in SEQ ID NO: 28, SEQ ID NO: 29, and SEQ ID NO: 30. In certain embodiments, the anti-OX40 antibody or antigen-binding fragment thereof comprises a VH domain of SEQ ID NO: 31 and a VL domain of SEQ ID NO: 32.

In certain embodiments, the anti-OX40 antibody or antigen-binding fragment thereof comprises (i) a VH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 31, wherein the VH domain comprises amino acids A33, H35, A50, I51, S52, S53, N54, G55, G56, S57, T58, Y59, Y60, N74, S101, W103, Y104, N105, S106, and E107 (positions according to numbering of SEQ ID NO: 31), and (ii) a VL domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 32, wherein the VL domain comprises amino acids W32, Y91, N92, Y94, and Y96 (positions according to numbering of SEQ ID NO: 32).

In certain embodiments, the anti-OX40 antibody or antigen-binding fragment thereof comprises (i) a VH domain comprising a HCDR1 region, a HCDR2 region, and a HCDR3 region as depicted in SEQ ID NO: 25, SEQ ID NO: 26, and SEQ ID NO: 27, and (ii) a VL domain comprising a LCDR1 region, a LCDR2 region, and a LCDR3 region as depicted in SEQ ID NO: 28, SEQ ID NO: 29, and SEQ ID NO: 30, wherein the VH domain comprises amino acids H35, A50, Y59, Y60, and N74 (positions according to numbering of SEQ ID NO: 31). In certain embodiments, the VL domain comprises the amino acid sequence of SEQ ID NO: 32.

In one aspect, the disclosure provides an anti-OX40 antibody or antigen-binding fragment thereof comprising a VH domain and a VL domain, wherein the anti-OX40 antibody or antigen-binding fragment thereof binds one or more of amino acids to one or more amino acids G20, M21, V22, R24, P35, C26, G37, P38, G39, F40, Y41, S46, K48, P49, C50, K51, P52, C53, T54, and W55 of SEQ ID NO: 47. In certain embodiments, the anti-OX40 antibody or antigen-binding fragment thereof binds to amino acids G20, M21, V22, R24, P35, C26, G37, P38, G39, F40, Y41, S46, K48, P49, C50, K51, P52, C53, T54, and W55 of SEQ ID NO: 47.

In certain embodiments, the anti-OX40 antibody or antigen-binding fragment thereof comprises a HCDR1 region, a HCDR2 region, and a HCDR3 region as depicted in SEQ ID NO: 97, SEQ ID NO: 98, and SEQ ID NO: 99, and a LCDR1 region, a LCDR2 region, and a LCDR3 region as depicted in SEQ ID NO: 100, SEQ ID NO: 101, and SEQ ID NO: 102. In certain embodiments, the anti-OX40 antibody or antigen-binding fragment thereof comprises a VH domain of SEQ ID NO: 103 and a VL domain of SEQ ID NO: 104.

In certain embodiments, the anti-OX40 antibody or antigen-binding fragment thereof comprises (i) a VH domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 103, wherein the VH domain comprises amino acids D30, D31, T33, L50, S52, W53, D54, S57, Y59, K65, L101, W102, Y104, and L105 (positions according to numbering of SEQ ID NO: 103), and (ii) a VL domain that is at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to the amino acid sequence of SEQ ID NO: 104, wherein the VL domain comprises amino acids W92 and T97 (positions according to numbering of SEQ ID NO: 104).

In certain embodiments, the anti-OX40 antibody or antigen-binding fragment thereof comprises (i) a VH domain comprising a HCDR1 region, a HCDR2 region, and a HCDR3 region as depicted in SEQ ID NO: 97, SEQ ID NO: 98, and SEQ ID NO: 99, and (ii) a VL domain comprising a LCDR1 region, a LCDR2 region, and a LCDR3 region as depicted in SEQ ID NO: 100, SEQ ID NO: 101, and SEQ ID NO: 102, wherein the VH domain comprises amino acids L50, Y59, and K65 (positions according to numbering of SEQ ID NO: 103). In certain embodiments, the VL domain comprises the amino acid sequence of SEQ ID NO: 104.

Multispecific Antigen Binding Proteins

The multispecific binding proteins (e.g., bispecific binding proteins) described herein comprise (a) a first antigen binding domain (ABD) comprising a single immunoglobulin heavy chain variable domain (ISVD) (e.g., VHH) with binding specificity to CD28 (such as an anti-CD28 antibody described herein); and (b) a second ABD comprising an immunoglobulin heavy chain variable domain (VH) and an immunoglobulin light chain variable domain (VL) with binding specificity to OX40 (such as an anti-CD40 antibody described herein).

The multispecific binding proteins are capable of antagonizing the activity of both CD28 and OX40 on the surface of a T cell, thereby repressing CD28 and OX40 co-stimulatory signals.

In certain embodiments, when the multispecific binding protein binds CD28 and OX40, the multispecific binding protein inhibits activated T-cells. In certain embodiments, the multispecific binding protein inhibits proliferation of T-cells. In certain embodiments, the multispecific binding protein inhibits expression of one or more pro-inflammatory cytokines. In certain embodiments, the pro-inflammatory cytokines are interferon gamma (IFNγ), tumor necrosis factor alpha (TNFα), interleukin 2 (IL-2), interleukin 5 (IL-5), interleukin 6 (IL-6), and interleukin 10 (IL-10). In particular embodiments, the pro-inflammatory cytokine is interferon gamma (IFNγ). In particular embodiments, the pro-inflammatory cytokine is tumor necrosis factor alpha (TNFα). In particular embodiments, the pro-inflammatory cytokine is interleukin 2 (IL-2). In particular embodiments, the pro-inflammatory cytokine is interleukin 5 (IL-5). In particular embodiments, the pro-inflammatory cytokine is interleukin 6 (IL-6). In particular embodiments, the pro-inflammatory cytokine is interleukin 10 (IL-10).

Figure 1A:
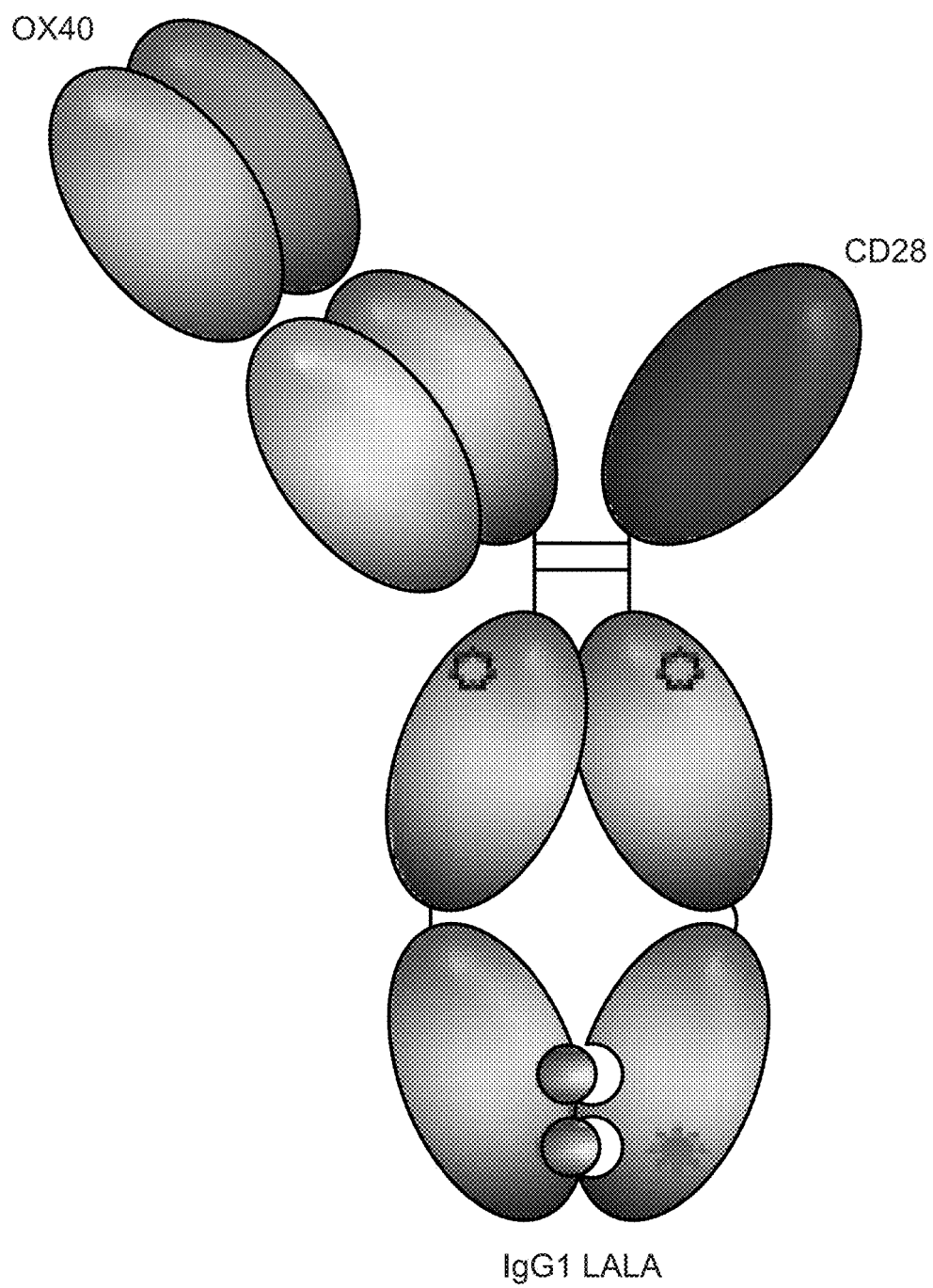
FIG. 1A and FIG. 1B are schematics of several anti-CD28/OX40 bispecific antibody formats of the present disclosure.
Figure 1B:
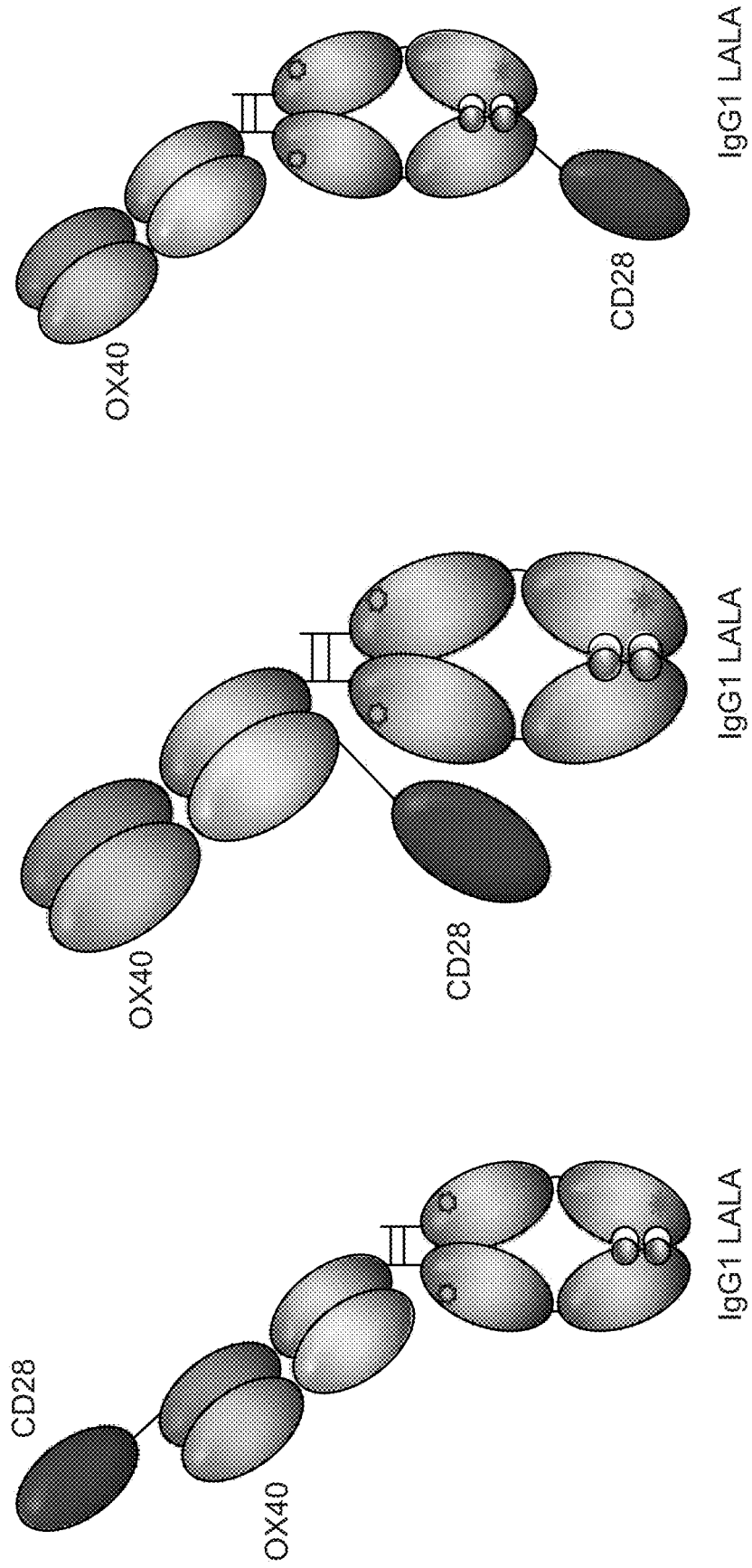

The multispecific binding proteins (e.g., bispecific binding proteins) described herein comprise a hybrid format with an anti-CD28 VHH domain and an anti-OX40 Fab domain comprising a VH and VL domain. One of several hybrid formats may be employed. In one aspect, the multispecific binding protein comprises the format depicted in FIG. 1A. In other aspects, the multispecific binding protein comprises one of the three formats depicted in FIG. 1B.

In each format, the multispecific binding protein comprises an immunoglobulin Fc domain or variant thereof. In certain embodiments, the Fc domain is a human IgG1 Fc domain. In certain embodiments, the Fc domain or variant thereof comprises a first Fc heavy chain and a second Fc heavy chain.

In certain embodiments, the first ABD (e.g., the anti-CD28 VHH) is linked to the first Fc heavy chain and the second ABD (e.g., the anti-OX40 VH/VL) is linked to the second Fc heavy chain.

In certain embodiments, the first ABD (e.g., the anti-CD28 VHH) is linked to the N-terminus of the first Fc heavy chain and the second ABD (e.g., the anti-OX40 VH/VL) is linked to the N-terminus of the second Fc heavy chain.

In certain embodiments, the first ABD is linked to the N-terminus of the second ABD VH.

In certain embodiments, the first ABD is linked to the C-terminus of the second Fc heavy chain and the second ABD is linked to the N-terminus of the second Fc heavy chain.

In certain embodiments, the VH is linked to a CH1 domain and the VL is linked to a CL domain. In certain embodiments, the first ABD is linked to the C-terminus of the CL domain.

In other aspects, the disclosure provides multispecific binding proteins (e.g., bispecific binding proteins) comprising (a) a first antigen binding domain (ABD) comprising an immunoglobulin single variable domain (ISVD) (e.g., VHH) with binding specificity to a first target antigen; (b) a second ABD comprising an immunoglobulin heavy chain variable domain (VH) and an immunoglobulin light chain variable domain (VL) with binding specificity to a second target antigen; and (c) an immunoglobulin Fc domain or variant thereof.

In certain embodiments, the Fc domain is a human IgG1 Fc domain. In certain embodiments, the Fc domain or variant thereof comprises a first Fc heavy chain and a second Fc heavy chain.

In certain embodiments, the first ABD is linked to the first Fc heavy chain and the second ABD is linked to the second Fc heavy chain.

In certain embodiments, the first ABD is linked to the N-terminus of the second ABD VH.

In certain embodiments, the first ABD is linked to the C-terminus of the second Fc heavy chain and the second ABD is linked to the N-terminus of the second Fc heavy chain.

In certain embodiments, the VH is linked to a CH1 domain and the VL is linked to a CL domain, and the first ABD is linked to the C-terminus of the CL domain.

In certain embodiments, the first target antigen comprises a tumor associated antigen (TAA). In certain embodiments, the second target antigen comprises a tumor associated antigen (TAA).

In certain embodiments, the first target antigen is a target associated with an autoimmune disease. In certain embodiments, the second target antigen is a target associated with an autoimmune disease.

Fc Domain

As used herein, the term "Fc domain" refers to an immunoglobulin hinge region (which natively bears a first binding site to FcγRs), a CH2 domain (which natively bears a second binding site to FcγRs), and a CH3 domain of an immunoglobulin (e.g. of an IgG, IgA or IgD immunoglobulin), and/or when applicable of a CH4 domain of an immunoglobulin (e.g. for IgM and IgE). The Fc domain or variant thereof comprises a first Fc heavy chain polypeptide and a second Fc heavy chain polypeptide which dimerize to form the Fc domain.

The term "Fc variant" as used herein refers to a molecule or sequence that is modified from a native Fc. Thus, the term "Fc variant" includes a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, (7) antibody-dependent cellular cytotoxicity (ADCC), and/or (8) heterodimerization. The term "Fc variant" also encompasses C-terminally clipped Fc domains, such as the clipping or removal of a C-terminal lysine from the Fc domain CH3 region. C-terminal Fc clipping is described in further detail in Faid et al. (Eur J Pharm Sci. 2021. 159: 105730), incorporated herein by reference.

In an aspect of the disclosure, the multispecific binding proteins comprising a first Fc heavy chain polypeptide and a second Fc heavy chain polypeptide are heterodimerized through knobs-into-holes pairing (KiH). This dimerization technique utilizes protuberances ("knobs") and cavities ("holes") engineered into the interface of CH3 domains. Where a suitably positioned and dimensioned knob or hole exists at the interface of either the first or second CH3 domain, it is only necessary to engineer a corresponding hole or knob, respectively, at the adjacent interface, thus promoting and strengthening Fc domain pairing in the CH3/CH3 domain interface. A "knob" refers to an at least one amino acid side chain, typically a larger side chain, that protrudes from the interface of the CH3 portion of a first Fc domain. The protrusion creates a "knob" which is complementary to and received by a "hole" in the CH3 portion of a second Fc domain. The "hole" is an at least one amino acid side chain, typically a smaller side chain, which recedes from the interface of the CH3 portion of the second Fc domain. This technology is described, for example, in U.S. Pat. No. 5,821,333; Ridgway et ak, Protein Engineering 9:617-621 (1996); and Carter P., J. Immunol. Methods 248: 7-15 (2001).

Exemplary amino acid residues that may act as a knob include arginine (R), phenylalanine (F), tyrosine (Y), and tryptophan (W). An existing amino acid residue in the CH3 domain may be replaced or substituted with a knob amino acid residue. Preferred amino acids to be substituted may include any amino acid with a small side chain, such as alanine (A), asparagine (N), aspartic acid (D), glycine (G), serine (S), threonine (T), or valine (V).

Exemplary amino acid residues that may act as a hole include alanine (A), serine (S), threonine (T), and valine (V). An existing amino acid residue in the CH3 domain may be replaced or substituted with a hole amino acid residue. Preferred amino acids to be substituted may include any amino acid with a large or bulky side chain, such as arginine (R), phenylalanine (F), tyrosine (Y), or tryptophan (W).

The CH3 domain can be derived from a human IgG1 antibody. Exemplary amino acid substitutions to the CH3 domain include T366Y, T366W, F405A, F405W, Y407T, Y407A, Y407V, T394S, and combinations thereof. A certain exemplary combination is T366Y or T366W for the knob mutation on a first CH3 domain and Y407T or Y407V for the hole mutation on a second CH3 domain.

In certain embodiments, the first Fc heavy chain comprises a Y349C substitution according to Eu numbering and the second Fc heavy chain comprises a S354C substitution according to Eu numbering.

In certain embodiments, the first Fc heavy chain comprises a Y349C, T366S, L368A, or Y407V substitutions according to Eu numbering and the second Fc heavy chain comprises a T366W substitution according to Eu numbering.

In certain embodiments, at least one Fc heavy chain comprises H435R and Y436F substitutions according to Eu numbering.

In certain embodiments of the disclosure, the multispecific binding proteins comprising a first Fc heavy chain polypeptide and a second Fc heavy chain polypeptide are heterodimerized through Fab arm exchange (FAE). A human IgGl possessing a P228S hinge mutation may contain an F405L or K409R CH3 domain mutation. Mixing of the two antibodies with a reducing agent leads to FAE. This technology is described in U.S. Pat. No. 9,212,230 and Labrijn A. F., Proc Natl Acad Sci USA 110(13): 5145-5150 (2013).

In certain embodiments of the disclosure, the multispecific binding proteins comprising a first Fc heavy chain polypeptide and a second Fc heavy chain polypeptide are heterodimerized through electrostatic steering effects. This dimerization technique utilizes electrostatic steering to promote and strengthen Fc domain pairing in the CH3/CH3 domain interface. The charge complementarity between two CH3 domains is altered to favor heterodimerization (opposite charge pairing) over homodimerization (same charge pairing). In this method, the electrostatic repulsive forces prevent homodimerization. Exemplary amino acid residue substitutions may include K409D, K392D, and/or K370D in a first CH3 domain, and D399K, E356K, and/or E357K in a second CH3 domain. This technology is described in US Patent Application Publication No. 2014/0154254 A1 and Gunasekaran K., J Biol Chem 285(25): 19637-19646 (2010).

In certain embodiments of the disclosure, the multispecific binding proteins comprising a first Fc heavy chain polypeptide and a second Fc heavy chain polypeptide are heterodimerized through hydrophobic interaction effects. This dimerization technique utilizes hydrophobic interactions instead of electrostatic ones to promote and strengthen Fc domain pairing in the CH3/CH3 domain interface. Exemplary amino acid residue substitution may include K409W, K360E, Q347E, Y349S, and/or S354C in a first CH3 domain, and D399V, F405T, Q347R, E357W, and/or Y349C in a second CH3 domain. Preferred pairs of amino acid residue substitutions between a first CH3 domain and a second CH3 domain include K409W:D399V, K409W:F405T, K360E:Q347R, Y349S:E357W, and S354C:Y349C. This technology is described in US Patent Application Publication No. 2015/0307628 A1.

In certain embodiments of the disclosure, the multispecific binding proteins comprising a first Fc heavy chain polypeptide and a second Fc heavy chain polypeptide are heterodimerized through the use of leucine zipper fusions. Leucine zipper domains fused to the C terminus of each CH3 domain of the antibody chains force heterodimerization. This technology is described in Wranik B., J Biol Chem 287(52): 43331-43339 (2012).

In certain embodiments of the disclosure, the multispecific binding proteins comprising a first Fc heavy chain polypeptide and a second Fc heavy chain polypeptide are heterodimerized through the use of a Strand Exchange Engineered Domain (SEED) body. CH3 domains derived from an IgG and IgA format force heterodimerization. This technology is described in Muda M., Protein Eng. Des. Sel. 24(5): 447-454 (2011).

Unless otherwise stated, all antibody constant region numbering employed herein corresponds to the EU numbering scheme, as described in Edelman et ah, Proc. Natl. Acad. Sci. USA 63(1): 78-85 (1969). Additional methods of heterodimerization of heavy and/or light chains and the generation and purification of asymmetric antibodies are known in the art. See, for example, Klein C., mABs 4(6): 653-663 (2012), and U.S. Pat. No. 9,499,634, each of which is incorporated herein by reference.

Additional Fc domain mutations are envisioned to alter Fc function, including, but not limited to, altered Antibody Dependent Cellular Cytotoxicity (ADCC) and Complement-Dependent Cytotoxicity (CDC).

In certain embodiments, the multispecific binding proteins comprise an IgG1 constant domain with a L234A and L235A amino acid substitution, according to Eu numbering.

Expression of Antigen-Binding Proteins

In one aspect, nucleic acid molecules encoding the antibodies and antigen-binding fragments thereof disclosed herein are provided. Methods of making binding proteins comprising expressing these nucleic acid molecules are also provided.

Nucleic acid molecules encoding the antibodies disclosed herein are typically inserted in an expression vector for introduction into host cells that may be used to produce the desired quantity of the antibodies. Accordingly, in certain aspects, the disclosure provides expression vectors comprising nucleic acid molecules disclosed herein and host cells comprising these vectors and nucleic acid molecules.

The term "vector" or "expression vector" is used herein to mean vectors used in accordance with the present disclosure as a vehicle for introducing into and expressing a desired gene in a cell. As known to those skilled in the art, such vectors may readily be selected from the group consisting of plasmids, phages, viruses and retroviruses. In general, vectors compatible with the disclosure will comprise a selection marker, appropriate restriction sites to facilitate cloning of the desired gene and the ability to enter and/or replicate in eukaryotic or prokaryotic cells.

Numerous expression vector systems may be employed for the purposes of this disclosure. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed or introduced into the same cell by co-transformation. Additional elements may also be needed for optimal synthesis of mRNA. These elements may include signal sequences, splice signals, as well as transcriptional promoters, enhancers, and termination signals. In some embodiments, the cloned variable region genes are inserted into an expression vector along with the heavy chain constant region genes (e.g., human constant region genes) synthesized as discussed above.

In other embodiments, the antibodies may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980, which is incorporated by reference herein in its entirety for all purposes. Those skilled in the art will appreciate that such expression systems may be used to effectively produce the full range of polypeptides disclosed in the instant application.

More generally, once a vector or DNA sequence encoding an antibody or fragment thereof has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Plasmid introduction into the host can be by electroporation. The transformed cells are grown under conditions appropriate to the production of the light chains and heavy chains and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, from supernatant of lysed cells culture, or from the cell culture containing both the medium and the suspended cells.

In one embodiment, a host cell line used for antibody expression is of mammalian origin. Those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CV-1 (monkey kidney line), COS (a derivative of CV-1 with SV40 T antigen), R1610 (Chinese hamster fibroblast) BALBC/3T3 (mouse fibroblast), HEK (human kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (POTELLIGENT® cells) (Biowa, Princeton, N.J.)). In one embodiment, NSO cells may be used. CHO cells are particularly useful. Host cell lines are typically available from commercial services, e.g., the American Tissue Culture Collection, or from authors of published literature.

In vitro production allows scale-up to give large amounts of the desired polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the antibodies featured in the disclosure can also be expressed in non-mammalian cells such as bacteria or yeast or plant cells. In this regard, it will be appreciated that various unicellular non-mammalian microorganisms such as bacteria can also be transformed, i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the binding proteins can become part of inclusion bodies. In some embodiments, the binding proteins are then isolated, purified and assembled into functional molecules. In some embodiments, the binding proteins of the disclosure are expressed in a bacterial host cell. In some embodiments, the bacterial host cell is transformed with an expression vector comprising a nucleic acid molecule encoding a binding protein of the disclosure.

In addition to prokaryotes, eukaryotic microbes may also be used. *Saccharomyces cerevisiae*, or common baker's yeast, is the most commonly used among eukaryotic microbes, although a number of other strains are commonly available. For expression in *Saccharomyces*, the plasmid YRp7, for example (Stinchcomb et al., Nature, 282:39 (1979); Kingsman et al., Gene, 7:141 (1979); Tschemper et al., Gene, 10:157 (1980)), is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

Methods of Administering Antigen Binding Proteins

Methods of preparing and administering antigen binding proteins to a subject are well known to or are readily determined by those skilled in the art. The route of administration of the antigen binding proteins of the current disclosure may be oral, parenteral, by inhalation or topical. The term parenteral as used herein includes intravenous, intraarterial, intraperitoneal, intramuscular, subcutaneous, rectal or vaginal administration. The route of administration may be intravenous administration. The route of administration may be subcutaneous administration. While all these forms of administration are clearly contemplated as being within the scope of the current disclosure, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the modified antibodies can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the compositions and methods of the current disclosure, pharmaceutically acceptable carriers include, but are not limited to, 0.01-0.1 M or 0.05 M phosphate buffer, or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage, and should also be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. Isotonic agents, for example, sugars, polyalcohols, such as mannitol, sorbitol, or sodium chloride may also be included in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a modified binding polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation typically include vacuum drying and freeze-drying, which yield a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in US20020102208 and U.S. Pat. No. 6,994,840, each of which is incorporated herein by reference. Such articles of manufacture can include labels or package inserts indicating that the associated compositions are useful for treating a subject suffering from, or predisposed to autoimmune or neoplastic disorders.

Effective doses of the compositions of the present disclosure, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

As previously discussed, the antigen binding proteins of the present disclosure, immunoreactive fragments or recombinants thereof may be administered in a pharmaceutically effective amount for the in vivo treatment of mammalian disorders. In this regard, it will be appreciated that the disclosed antigen binding proteins will be formulated to facilitate administration and promote stability of the active agent.

Pharmaceutical compositions in accordance with the present disclosure typically include a pharmaceutically acceptable, non-toxic, sterile carrier such as physiological saline, nontoxic buffers, preservatives and the like. For the purposes of the instant application, a pharmaceutically effective amount of the modified antigen binding proteins, immunoreactive fragment or recombinant thereof, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the modified binding polypeptide will typically be capable of interacting with selected immunoreactive antigens on neoplastic or immunoreactive cells and provide for an increase in the death of those cells. Of course, the pharmaceutical compositions of the present disclosure may be administered in single or multiple doses to provide for a pharmaceutically effective amount of the modified binding polypeptide.

In keeping with the scope of the present disclosure, the antigen binding proteins of the disclosure may be administered to a human or other animal in accordance with the aforementioned methods of treatment in an amount sufficient to produce a therapeutic or prophylactic effect. The antigen binding proteins of the disclosure can be administered to such human or other animal in a conventional dosage form prepared by combining the antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of binding polypeptides described in the current disclosure may prove to be particularly effective.

The biological activity of the pharmaceutical compositions defined herein can be determined for instance by T cell activation assays, such as through the detection of pro- or anti-inflammatory cytokine expression. "Efficacy" or "in vivo efficacy" as used herein refers to the response to therapy by the pharmaceutical composition of the disclosure, using e.g. standardized NCI response criteria. The success or in vivo efficacy of the therapy using a pharmaceutical composition of the disclosure refers to the effectiveness of the composition for its intended purpose, i.e. the ability of the composition to cause its desired effect, i.e. depletion of pathologic cells, e.g. repression of active immune cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used.

Methods of Treatment

The antigen binding proteins described herein (e.g., the multispecific binding proteins with specificity to CD28 and OX40) are useful in the treatment or prevention of diseases associated with activated T cells (e.g., autoimmune diseases). The targets CD28 and OX40 are co-stimulatory receptors on the surface of T cells, responsible, in part, for promoting T cell activity and proliferation. Accordingly, antagonistic anti-CD28 and anti-OX40 antibodies, and antagonistic multispecific antibodies with anti-CD28 and anti-OX40 antigen binding domains, can repress the co-stimulatory activities of CD28 and OX40 on T cells.

In certain embodiments, the multispecific binding proteins of the disclosure inhibit activated T-cells. In certain embodiments, the multispecific binding proteins of the disclosure inhibit proliferation of T-cells. In certain embodiments, the multispecific binding proteins of the disclosure inhibit expression of one or more pro-inflammatory cytokines. In certain embodiments, the pro-inflammatory cytokines include, but are not limited to, interferon gamma (IFNγ), tumor necrosis factor alpha (TNFα), interleukin 2 (IL-2), interleukin 5 (IL-5), interleukin 6 (IL-6), and interleukin 10 (IL-10). In particular embodiments, the pro-inflammatory cytokine is interferon gamma (IFNγ). In particular embodiments, the pro-inflammatory cytokine is tumor necrosis factor alpha (TNFα). In particular embodiments, the pro-inflammatory cytokine is interleukin 2 (IL-2).

In particular embodiments, the pro-inflammatory cytokine is interleukin 5 (IL-5). In particular embodiments, the pro-inflammatory cytokine is interleukin 6 (IL-6). In particular embodiments, the pro-inflammatory cytokine is interleukin 10 (IL-10).

In one aspect, the disclosure provides a method for treating an autoimmune disease or disorder in a subject, comprising administering to a subject in need thereof a multispecific binding protein comprising: (a) a first antigen binding domain (ABD) comprising an immunoglobulin single variable domain (ISVD) (e.g., VHH) with binding specificity to CD28; and (b) a second ABD comprising an immunoglobulin heavy chain variable domain (VH) and an immunoglobulin light chain variable domain (VL) with binding specificity to OX40.

In certain embodiments, when the multispecific binding protein binds CD28 and OX40, the multispecific binding protein inhibits activated T-cells.

In another aspect, the disclosure provides a multispecific binding protein comprising: (a) a first antigen binding domain (ABD) comprising an immunoglobulin single variable domain (ISVD) (e.g., VHH) with binding specificity to CD28; and (b) a second ABD comprising an immunoglobulin heavy chain variable domain (VH) and an immunoglobulin light chain variable domain (VL) with binding specificity to OX40, for use in a method for the treatment of an autoimmune disease or disorder.

In certain embodiments, the autoimmune disease is connective tissue disease-interstitial lung disease (CTD-ILD). CTD-ILD (also referred to as connective tissue disease-associated interstitial lung disease) is a lung disease that may occur in subjects with a connective tissue disease. CTD-ILD causes inflammation and scarring (fibrosis) of the lungs.

In certain embodiments, the autoimmune disease is graft vs. host disease (GvHD).

EXAMPLES

The following examples are put forth so as to provide those of ordinary skill in the art with a complete disclosure and description of how to make and use the methods and compositions featured in the disclosure and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Transfection, Expression, and Purification

Transfection for Expression

FREESTYLE HEK-293-FS cells were transfected with high-quality plasmid preparations according to the manufacturer's instructions. Expression was evaluated 48 or 144 hours after transfection with flow cytometry or Octet. Supernatants were harvested and purified on HiTrap MabSelect SuRe (Cytiva) affinity column according to manufacturer's instructions. Affinity purified samples were polished by the protein by size exclusion chromatography (SEC) using a Superdex200 26/60 (Cytiva) column.

Fab-Like Construction, Production, and Purification

After amplification with polymerase chain reaction, complementary DNA of the VHH were cloned into a proprietary mammalian expression vector in frame with either the human CL domain or the human IgG1 CH1 domain fused to human influenza hemagglutinin and 6-His tags. Plasmids were purified using NucleoBond Macherey-Nagel kits and Sanger sequenced. Bispecific (bsFab) or bivalent Fab-like (bvFab) antibodies were produced by cotransfecting FREESTYLE HEK293-FS cells with a mix of two plasmids encoding two distinct (bsFab) or two identical (bvFab) VHHs fused to each of the Fab constant domains. Supernatants were harvested 7 days later, purified on Nickel affinity columns, and analyzed on CALIPER GXII (Perkin Elmer).

Example 2. Anti-CD28/OX40 Bispecific mAb

Origin of Anti-CD28 Human VHHs

Anti-human CD28 VHHs were generated by performing phage display selections on human CD28 antigen with a VHH library built from a llama immunized with human CD28. There was no need of selecting specifically on cynomolgus CD28 antigen as human and cynomolgus CD28 sequences are 100% identical.

42 VHHs were characterized in bivalent and monovalent Fab-like format for: i) binding to cell lines expressing human CD28; ii) binding to human CD28 recombinant protein by ELISA; iii) epitope binning and competition with natural ligand CD80 and benchmark antibodies (TGN1412 and 9.3); iv) sequence clustering; and v) antagonist activity in MLR.

18 antagonist VHHs were then selected for in-depth functional evaluation: i) antagonist potency in reporter assay; ii) agonist activity in T cell activation assay (TCA) as counter-screening; iii) super agonist activity in cytokine release assay as counter-screening; iv) antagonist potency in MLR.

Sequence and activity correlation (antagonist activity without agonist activity) led to the selection of 5 sequence-diverse functionally potent VHHs. The 5 hit VHHs displayed an antagonist activity in MLR equal or better as compared to a clinically validated anti-CD28 benchmark molecule.

Anti-CD28 VHH Epitope & Paratope Determination

Figure 2A:
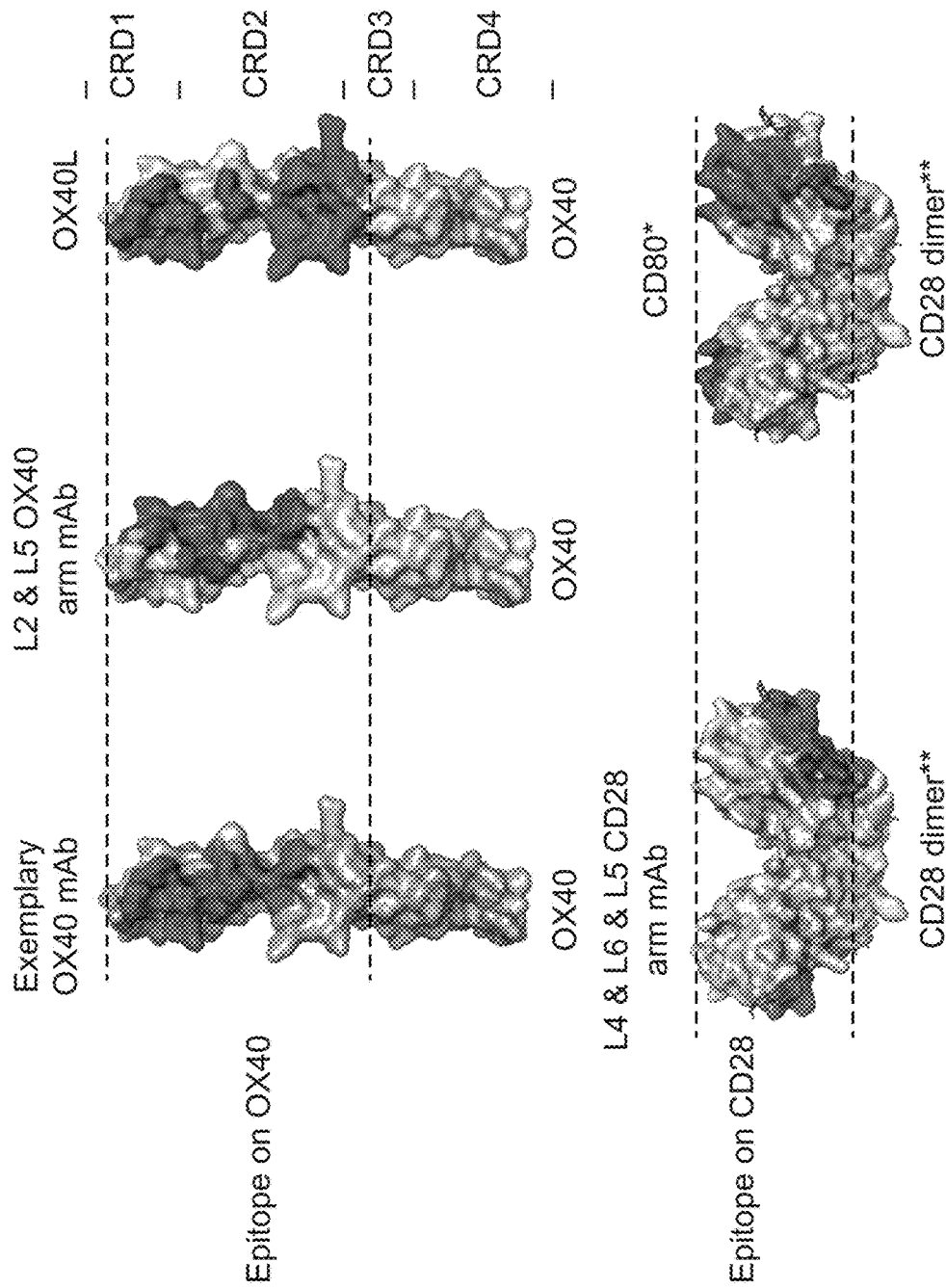
FIG. 2A depict epitopes of the OX40 and CD28 binders and comparison with their ligand binding sites. Top panel: Epitope of an exemplary OX40 mAb on OX40, determined by X-ray crystallography (left); Epitope of L2 & L5 OX40 arm mAb on OX40, determined by cryoEM (middle); and OX40L binding site on OX40, mapped using PDB 2HEV (right). Bottom panel: Epitope of L4 & L6 & L5 CD28 arm on CD28, determined by X-ray crystallography (left), and modeled CD80 binding site on CD28 (based on CD80-CTLA4 structure; protein data base (PDB 1I8L) (right). The CD28 dimer was modeled on PDB 1YJD.
Figure 2B:
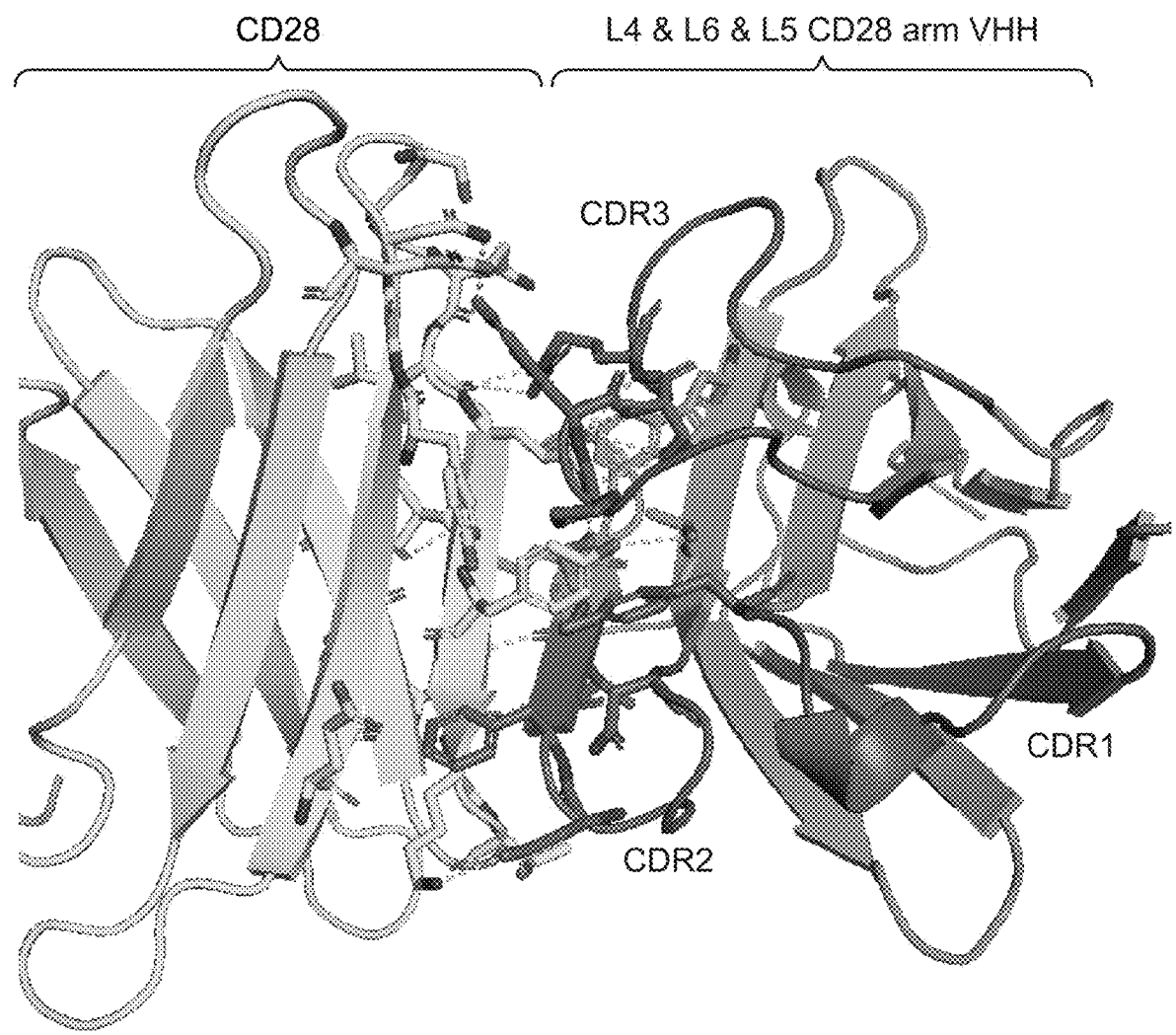
FIG. 2B depicts a crystal structure of the L4 & L6 & L5 CD28 arm VHH binding to CD28 at 2.9 Å resolution. CDR locations on the CD28 VHH are designated.

The epitope and paratope of the L4 & L6 & L5 CD28 arm VHH was determined by generating a crystal structure of the VHH in complex with human CD28. CD28-His (amino acids 19-136 of human CD28) was expressed in Expi293 cells. CD28-His was the purified by HisTrap and SEC purification. CD28-L4 & L6 & L5 CD28 arm VHH complexes were prepared by mixing purified CD28-His and VHH-His, followed by SEC purification. The crystal structure was then generated at 2.9 Å resolution (FIG. 2B). The epitope of L4 & L6 & L5 CD28 arm VHH is shown below, with epitope amino acids in bold, underlined text:

(SEQ ID NO: 46)
NKILVKQSPMLVAYDNAVNLSCKYSYNLFSREFRASLHKGLDSAVEVCV

VYGNYSQQLQVYSKTGFNCDGKLGNESVTFYLQNLYVNQTDIYFCKIEV

MYPPPYLDNEKSNGTIIHVK

The epitope of L4 & L6 & L5 CD28 arm VHH is amino acid positions E32, E46, V47, C48, Y51, G52, N53, S55, Q57, L58, Q59, V60, Y61, S62, K63, T64, N67, C68, and D69 (numbering according to SEQ ID NO: 46).

The paratope of L4 & L6 & L5 CD28 arm VHH is amino acid positions Y33, W47, T50, N52, D56, F57, T58, S59, K65, P102, Y103, S104, and R105.

Anti-OX40 Fab Epitope & Paratope Determination

The epitope and paratope of the L1 & L4 OX40 arm Fab was determined by generating a crystal structure of the Fab in complex with human OX40. Human OX40 (amino acids 32-109 of human OX40) was used. The cryoEM structure of human OX40 in complex with the L1 & L4 OX40 arm was determined to 3.25 Å resolution. The epitope of L1 & L4 OX40 arm Fab is shown below, with epitope amino acids in bold, underlined text:

(SEQ ID NO: 47)
VGDTYPSNDRCCHECRPGNGMVSRCSRSQNTVCRPCGPGFYNDVVSSKP

CKPCTWCNLRSGSERKQLCTATQDTVCRC

The epitope of L1 & L4 OX40 arm Fab is amino acid positions V22, C33, R34, P35, C36, G37, P38, G39, F40, P49, C50, C53, W55, R64, L67, C68, T69, and A70 (numbering according to SEQ ID NO: 47).

The paratope of L1 & L4 OX40 arm Fab is amino acid positions [LIGHT CHAIN] W32, D50, S92 and amino acid positions [HEAVY CHAIN] H35, S52, Q54, G56, S57, T58, Y59, Y102, Y104, R105, and W106.

The epitope and paratope of the L2 & L5 OX40 arm Fab was determined by generating a cryo-EM structure of the Fab in complex with human OX40. Human OX40 (amino acids 29-170 of human OX40) was used. The cryoEM structure of human OX40 in complex with the L2 & L5 arm was determined to 3.3 Å resolution. The epitope of L2 & L5 OX40 arm Fab is shown below, with epitope amino acid in bold, underlined text:

(SEQ ID NO: 47)
VGDTYPSNDRCCHECRPGNGMVSRCSRSQNTVCRPCGPGFYNDVVSSKP

CKPCTWCNLRSGSERKQLCTATQDTVCRC

The epitope of L2 & L5 OX40 arm Fab is amino acid positions of R16, N19, V22, V32, C33, R34, P35, C36, G37, P38, G39, F40, P49, C50, C53, T54, W55, C56, R64, L67, C68, T69, A70, and T74 (Numbering according to SEQ ID NO: 47).

The paratope of L2 & L5 OX40 arm Fab is amino acid positions [LIGHT CHAIN] W32, Y91, N92, Y94, and Y96, and amino acid positions [HEAVY CHAIN] A33, H35, A50, I51, S52, S53, N54, G55, G56, S57, T58, Y59, Y60, N74, S101, W103, Y104, N105, S106, and E107.

The epitope and paratope of the prototype OX40 arm Fab was determined by generating a cryo-EM structure of the Fab in complex with human OX40. Human OX40 (amino acids 29-170 of human OX40) was used. The crystal structure of human OX40 in complex with the prototype arm was determined to 3.35 Å resolution. The epitope of the prototype OX40 arm Fab is shown below, with epitope amino acid in bold, underlined text:

(SEQ ID NO: 47)
VGDTYPSNDRCCHECRPGNGMVSRCSRSQNTVCRPCGPGFYNDVVSSKP

CKPCTWCNLRSGSERKQLCTATQDTVCRC

The epitope of the prototype OX40 arm Fab is amino acid positions of G20, M21, V22, R24, P35, C26, G37, P38, G39, F40, Y41, S46, K48, P49, C50, K51, P52, C53, T54, and W55 (numbering according to SEQ ID NO: 47).

The paratope of the prototype OX40 arm Fab is amino acid positions [LIGHT CHAIN] W92 and T97, and amino acid positions [HEAVY CHAIN] D30, D31, T33, L50, S52, W53, D54, S57, Y59, K65, L101, W102, Y104, and L105.

Bispecific Format Screening

Prior to finalization of the monoblock screening 3 anti-OX40 mAbs, 2 anti-OX40 VHHs and 2 anti-CD28 VHHs were selected for bispecific format evaluation. Bispecific formats were designed to evaluate the following criteria: i) effect of N-/C-terminal fusion of building blocks, ii) physical distance required between the two paratopes, and iii) valency requirement for anti-OX40 building blocks.

Altogether, 6 mAb-VHH hybrid formats, 10 VHH-Fc fusion formats and 6 VHH-only formats were screened. In total, 137 bispecific molecules and 40 control molecules were produced and assessed by their biophysical and functional characteristics. The best formats were analyzed head-to-head in an MLR assay at 0.1 nM. A clear advantage of hybrid format over the VHH-Fc fusions and VHH-only constructs was observed. Accordingly, the antibody-like mAb-VHH hybrid format was selected as lead format (see FIG. 1A as the lead format and FIG. 1B for several variations of the lead format). Importantly, bispecific molecules in this hybrid format showed higher inhibition in MLR at low concentrations as compared to a clinically validated anti-CD28 or anti-OX40 benchmark molecule and Abatacept and the combination of building blocks.

Monoblock Hit Screening

Hit building blocks (9 anti-OX40 mAbs and 5 (+1 with clear agonist activity in TCA as positive control) anti-CD28 VHHs) were combined in the bispecific hybrid format. Biophysical and functional characterization of these 70 molecules (including controls) enabled selection of 6 bispecific molecules combining anti-OX40 L2 & L5 OX40 arm, L1 & L4 OX40 arm, and L3 & L6 OX40 arm mAbs with anti-CD28 L1 & L3 & L2 CD28 arm and L4 & L6 & L5 CD28 arm VHHs.

Immunogenicity Predictions and Optimization

Anti-CD28 VHH

In silico T cell epitope prediction (NetMHCII pan, Metapredictor) showed an improved antigenicity score for sequence-optimized variants as compared to the parental clones. The two VHH hits were found to be within the expected Metapredictor range for VHH.

Anti-OX40 Fabs (9 hits)

In silico analysis was performed with EpiVax and Metapredictor. Six out of Nine compounds showed a score within the expected range with both EpiVax and Metapredictor tools. Clones G3, J9 and CL-154787 showed a higher score. The 3 clones chosen for the bispecifics have no non-germinal residues and show acceptable antigenicity scores.

Example 3. Target Binding Affinity

SPR Binding to Recombinant Target Antigens

Target binding affinity measurements (KD (nM)) of the six bispecific antibodies to human and cyno OX40 and human CD28 were performed by surface plasmon resonance (SPR) analysis using a Biacore 8K instrument (Cytiva). Measurements were performed with HBS-EP+ as running buffer (Cytiva BR1006-69). An anti-human Fc antibody (Human Antibody Capture Kit, Cytiva BR-1008-39) was covalently coupled on Sensor Chip CM5 (Cytiva 29149603).

All eight flow cells were first activated for 420 seconds with 1-ethyl-3-(3-dimethylaminopropyl) carbodiimide/N-hydroxysuccinimide mixture (75-11.5 mg/mL) using a flow rate of 5 µL/minute (Amine Coupling Kit, Cytiva Life-Sciences, BR100050). The anti-human Fc antibody was diluted to 25 µg/mL in 10 mM acetate pH 5.0 and coupled for 420 seconds using a flow rate of 5 µL/minute. Uncoupled sites were deactivated with a 420 second injection of 1 M methanolamine pH 8.5 using a flow rate of 10 µL/minute. Following surface preparation, the bispecific molecules were diluted to 0.15 µg/ml in running buffer and captured as ligand for 90 seconds at 10 µl/min.

The respective target antigens (human CD28 (CD28-3910H, Creative Bio Mart), human OX40 (10481-H08H, Sino Biological) and cyno OX40 (internal production) were subsequently injected as analytes in multicycle kinetic experiments at concentrations of 100, 50, 25, 12.5, 6.3, 3.1 and 1.6 nM, respectively. Analyte association was monitored for 400 seconds at 30 µl/min, followed by an 800 second dissociation phase at 30 µl/min using running buffer as injectant. All analyte concentrations were performed as duplicates including buffer blanks for double referencing.

Surfaces were regenerated with a 60 second pulse of 3M MgCl$_2$ using a flow rate of 30 µL/minute. For analysis of the binding kinetics a 1:1 binding model with mass transfer limitation was used within the Insight Evaluation Software (Cytiva).

Figure 4A:
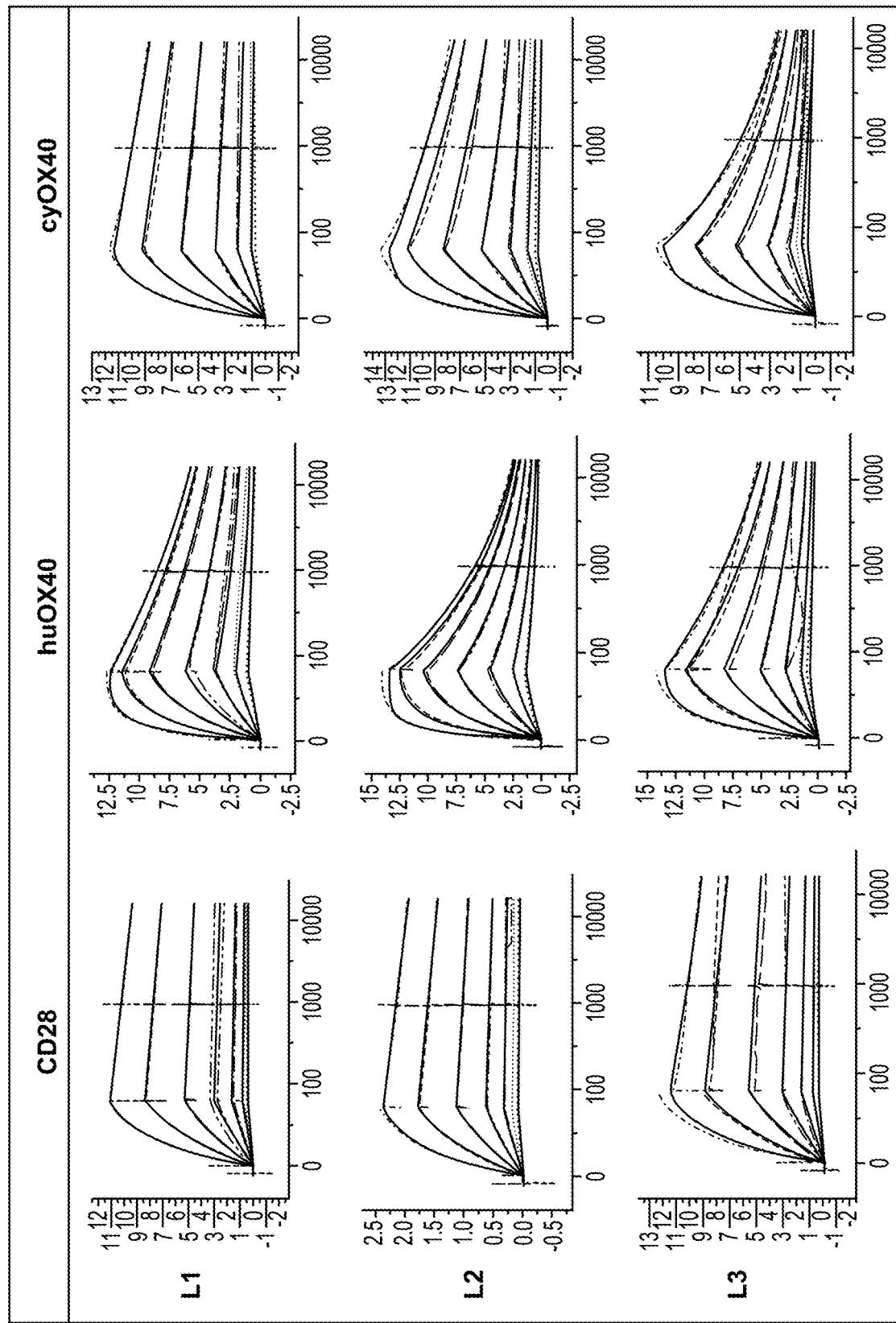
FIG. 4A and FIG. 4B depict results of the SPR binding kinetics study of exemplary bispecific antibodies designated L1-L6. "L" designates a lead candidate, with L1, L2, L3, L4 L5, and L6 representing 6 lead candidate exemplary bispecific antibodies.
Figure 4A:
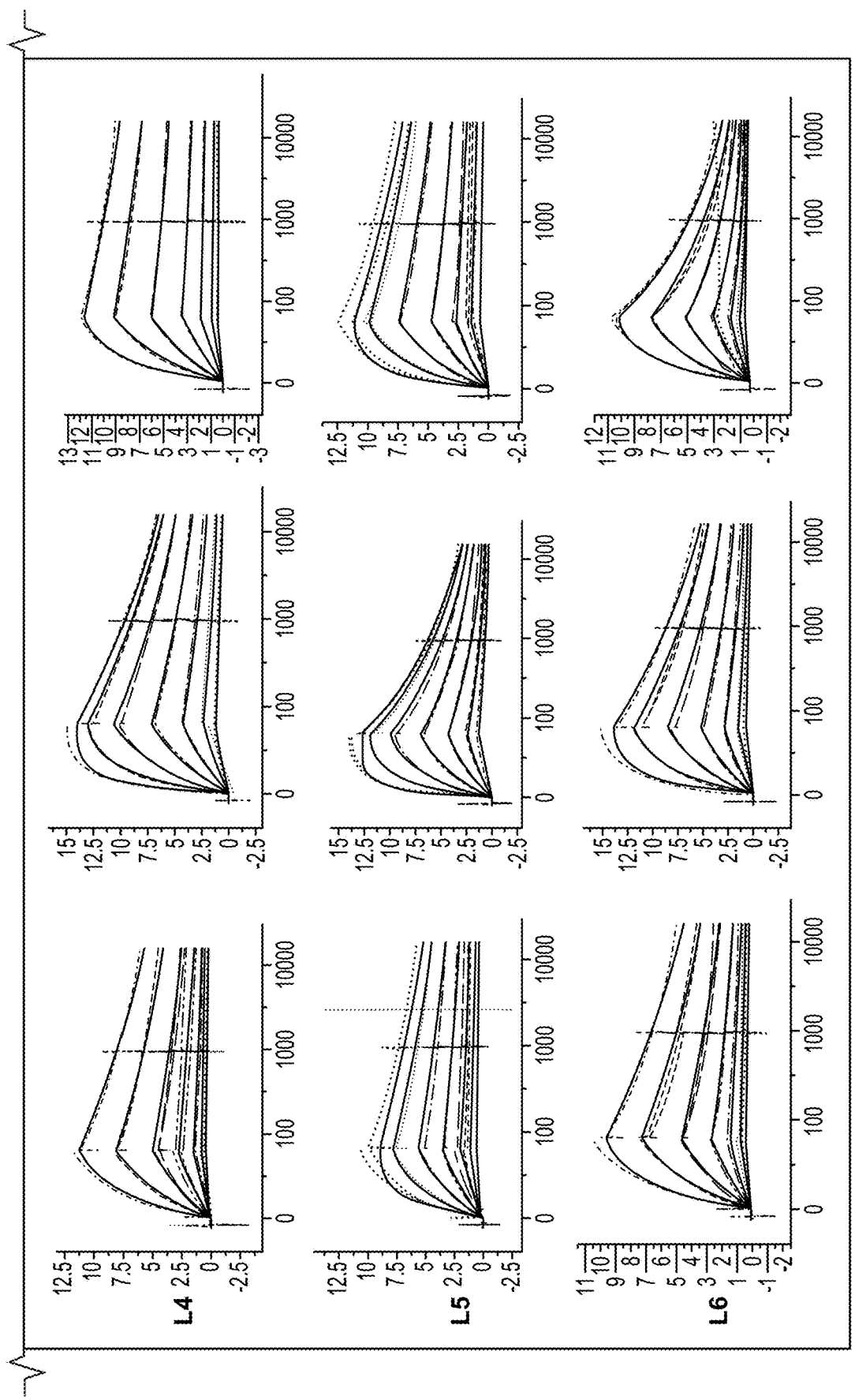
Figure 4B:
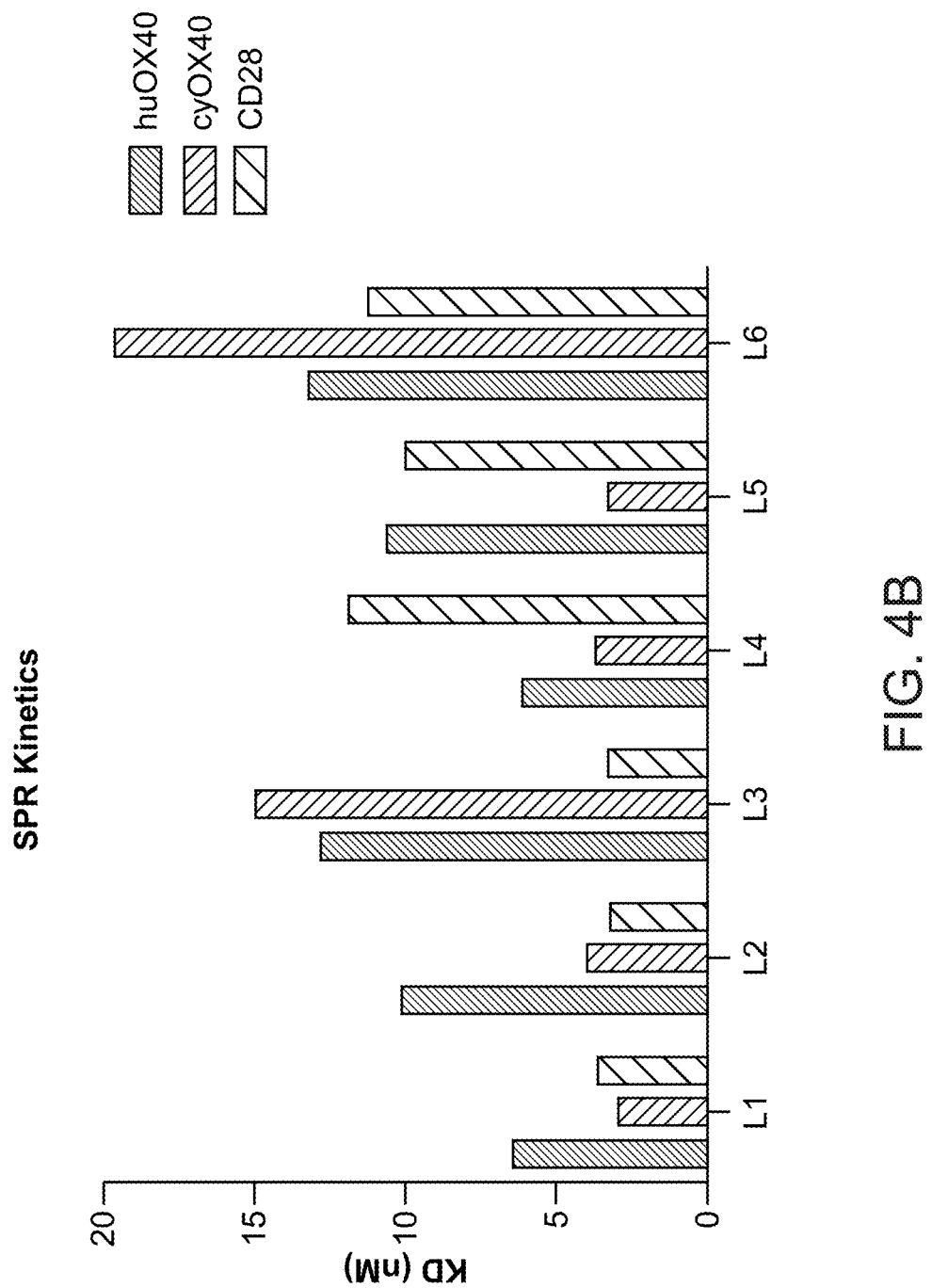

As shown in FIG. 4A and FIG. 4B, the six bispecific antibodies (L1-L6) displayed binding to CD28, human OX40, and cyno OX40.

SPR Binding to Recombinant Human FcRN

Binding affinity measurements (KD (nM)) of the 6 bispecific antibodies to human FcRn (Immunitrack, ITF01-200) were performed by surface plasmon resonance (SPR) analysis using a Biacore 8K instrument (Cytiva). The Series S Sensor Chip CAP was prepared according to the manufacturer instructions (28920234 Cytiva) Following surface preparation, human FcRn was diluted to 0.5 µg/ml in running buffer and captured as ligand for 90 seconds at 10 µl/min.

The bispecific samples were subsequently injected as analytes in multicycle kinetic experiments at concentrations of 1600, 800, 400, 200, 100, 50, 25 and 12.5 nM, respectively using a pH 6.0 running buffer.

Analyte association was monitored for 60 seconds at 30 µl/min, followed by a 120 second dissociation phase at 30 µl/min using running buffer as injectant. A single analyte injection in HBS-EP+ running buffer pH 7.4 was performed in order to show absence of binding of the bispecific to FcRn at pH7.4 All analyte concentrations were performed as duplicates including buffer blanks for double referencing.

Surfaces were regenerated with a 60 second pulse of GdnHCl/NaOH using a flow rate of 10 µL/minute. The equilibrium constant KD was calculated by the steady-state evaluation tool of the Biacore Insight Evaluation Software (Cytiva). KD values for binding CD28, human OX40, cyno OX40, and FcRN are recited below in Table 5.

TABLE 5

| | KD determination in nM | | | |
|---|---|---|---|---|
| Lead number | CD28* | Human OX40 | Cynomolgus Monkey OX40 | FcRN |
| L1 | 3.6 | 4.3 | 2.9 | 924 |
| L2 | 3.23 | 6.9 | 4 | 988 |
| L3 | 3.3 | 8.1 | 15 | 990 |
| L4 | 11.87 | 4.1 | 3.7 | 574 |
| L5 | 9.99 | 6.1 | 3.3 | 714 |
| L6 | 11.26 | 8.1 | 20 | 745 |

*Human and cynomolgus CD28 are identical.

Binding on Recombinant Cell Lines

The bispecific antibodies L1-L6 were tested for their ability to bind cells that express CD28 or OX40 on their surface. The cell lines used were HEK293 cells expressing human OX40 or cyano OX40, jurkat cells, and jurkat cells engineered to express human OX40. Flow cytometry binding assays were performed on a BD FACSCelesta™ Flow Cytometer or a BD FACSCanto™ II Flow Cytometer (Becton Dickinson) using 96-well U-bottom Cellstar plates (Greiner, 650185). Frozen target cells were thawed and seeded at 5×10$^4$ cells per well.

For live dead cell discrimination cells were stained according to manufacturer's protocol using the LIVE/DEAD™ Fixable Yellow Dead Cell Stain Kit (Molecular Probes, L34959). For dose-response-curves cells were incubated with a serial dilution of the bispecific antibodies at designated concentration in Stain Buffer FBS (Becton Dickinson, 554656) for 30 min at 4° C. After washing steps, the cells were incubated with the secondary detection antibody (Mouse Anti human IgG FC PE, Southern Biotech, 9040-09) for 15 min at 4° C. followed by washing steps. 104 viable cells per well were measured on a flow cytometer.

Analyzes were performed with FlowJo™ Software (Becton Dickinson). Cells were first gated in FSC/SSC. From the resulting cell population single cells and following viable were gated. Binding was analyzed as median fluorescence intensity (MFI) of the secondary antibody. Curves and calculations were generated using GraphPad Prism Software (Dotmatics).

Binding on Human Primary Cells

The bispecific antibodies were also tested for their binding activity on human T-cells. Briefly, Human PBMCs isolated from 2 different healthy donors were plated at 200000 cells/well in a U-bottom 96-well culture plate (NUNC #163320) which were pre-coated with OKT3 (Invitrogen 16-0037-85 used at 5 µg/ml, diluted in PBS at 4° C. overnight). As a control condition, PBMCs were cultured in additional plates without OKT3 activation. Cells were cultured in X-VIVO™ 15 with Phenol Red (Lonza, #BE02-060Q) for 48 hrs and washed with FACS buffer (PBS, 2 mM ETA, 2% FCS). Activated PBMCs were then incubated with serially diluted bispecific antibodies, ranging from 600 nM to 0.003 nM, for 30 min at 4° C. Following incubation, cells were centrifuged and labeled with 5 µg/ml of a PE-labeled mouse anti-Human IgG Fab secondary antibody (Invitrogen, #MA1-10377) diluted in FACS buffer. Stained cells were incubated for 45 min at 4° C., washed, and incubated for 30 min at 4° C. with 25 uL of FACS buffer containing a mixture of anti-CD4 BV711 (BD Biosciences #563028), anti-CD8 BV786 (BD Biosciences #563823) and CD25 BV421 (Biolegend #356114). Finally, stained cells were washed in FACS buffer and incubated with 50 µL of Viability Dye eFluor™ 780 diluted at 1/3000 in PBS, for 20 min in the dark at 4° C. After a last washing step, cells were analyzed on a Fortessa X-20 flow cytometer (BD Biosciences). For the analysis, cells were gated in FSC/SSC and on either CD4 or CD8 population. Binding was analyzed as median fluorescence intensity (MFI) of the secondary antibody. Curves and calculations of associated EC50 values were generated using GraphPad Prism Software.

Figure 5A:
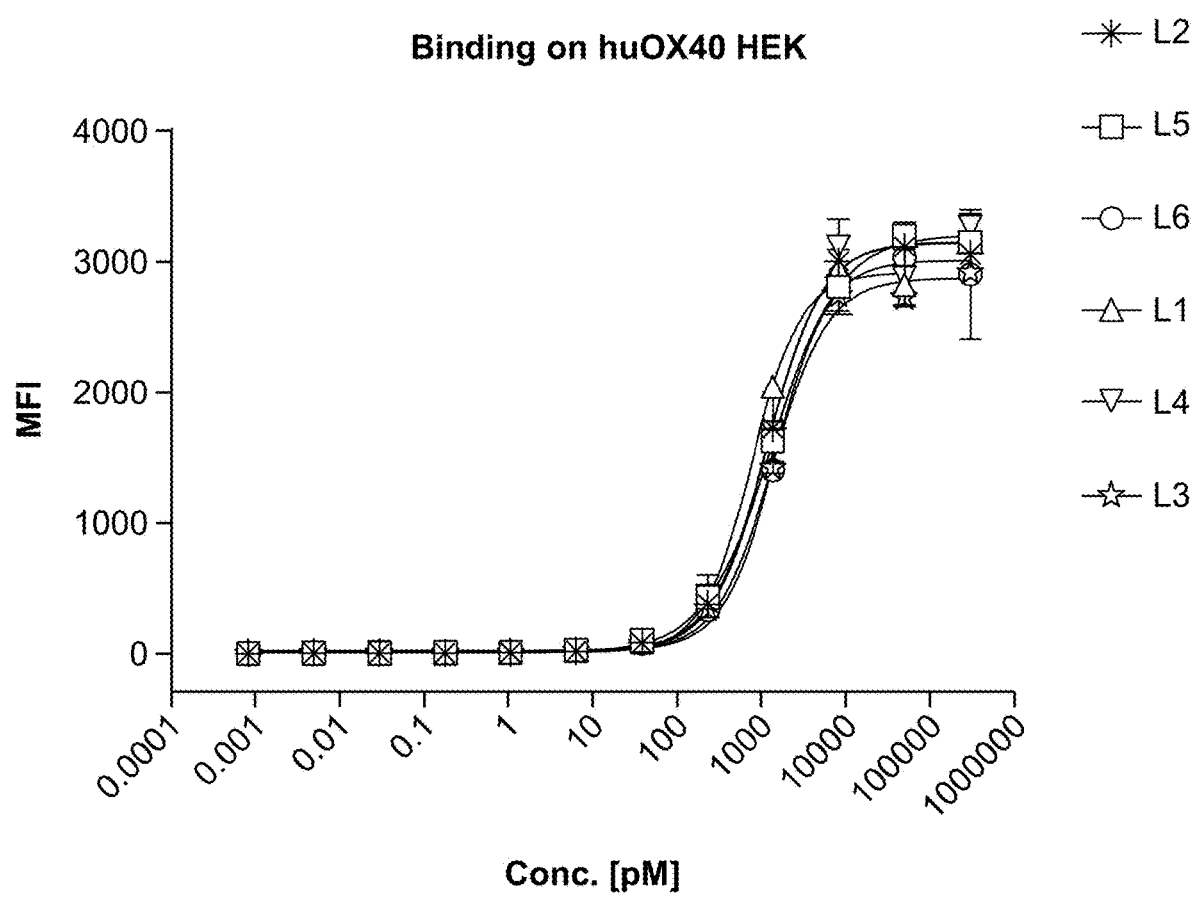
FIG. 5A depicts the binding of exemplary bispecific antibodies designated L1-L6 on the HEK293 cell line.
Figure 5B:
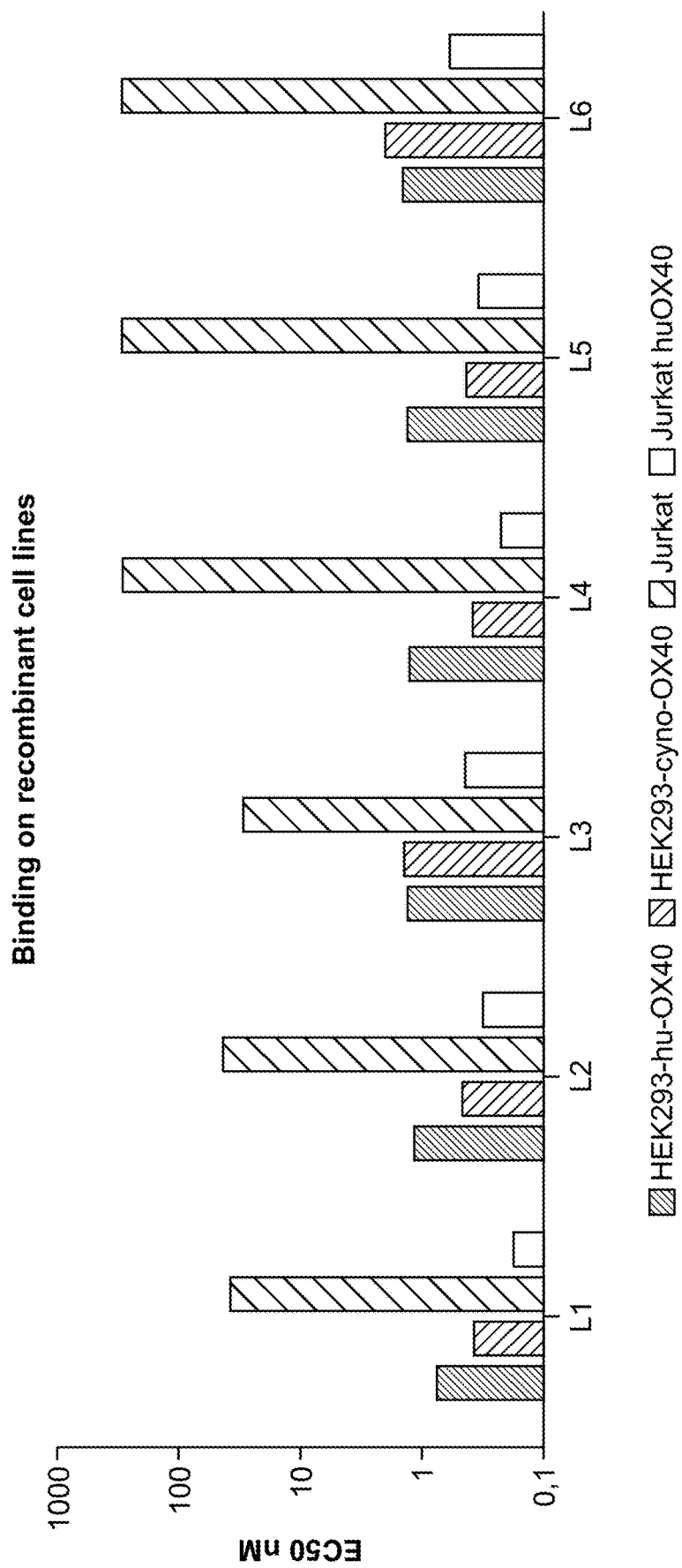
FIG. 5B depicts binding on various recombinant cell lines.
Figure 5C:
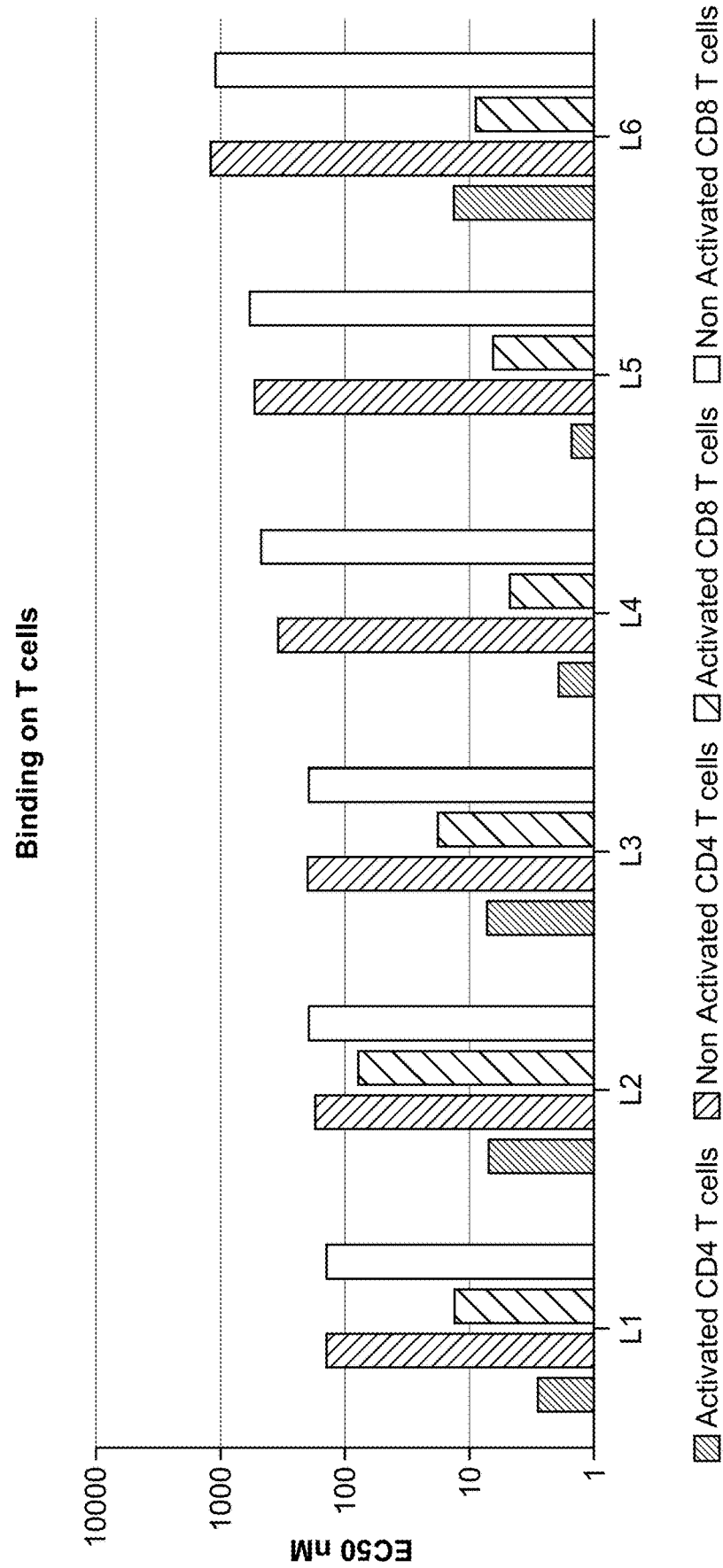
FIG. 5C depicts binding on various primary T cells.

As shown in FIG. 5A, FIG. 5B, and FIG. 5C, the bispecific antibodies L1-L6 were each capable of binding either CD28 or OX40 on the surface of the target cells.

Example 4. In Vitro Functional Data

Allogeneic Mixed Leukocyte Reaction (MLR)

Human CD14+ monocytes were isolated from PBMCs and cultured for 5 days with GM-CSF and IL-4 cytokines. The resulting immature dendritic cells were activated for 3 days with a cocktail of cytokines composed of GM-CSF, IL-4, IL-1b, IL-6, TNFa and PGE2 and co-cultured with ($1 \times 10^4$) carbocyfluorescein succinimidyl ester (CFSE)-labeled allogeneic PBMCs ($1 \times 10^4$ of matured DC+$2 \times 10^5$ of PBMCs) with or without negative and positive controls or test compounds used at 6 nM at the initiation of the assay. After 4-7 days, cytokine levels were measured in the collected supernatants and T-cell proliferation was measured using CFSE dilution. In parallel, samples were harvested at different time points from day 0 to day 7, and stained with Viability Dye eFluor 506 (eBioscience), anti-CD3 BUV805 (BD Bioscience), anti-CD4 BUV395 (BD Biosciences), anti-CD8 BUV3496 (BD Biosciences), anti-CD25 BV421 (BD Biosciences) anti-CD45RA FITC (eBioscience) and anti-CCR7 PE (eBioscience) for 30 min at 4° C. Subsequently, samples were washed and diluted in PBS containing 10% of count bright beads (invitrogen #C36950) and analyzed on a Fortessa X-20 flow cytometer (BD Biosciences). Subpopulations of naïve and central memory T-cells were defined as CD45RA+CD25$^{low}$ and CD45RA-CCR7$^{hi}$, respectively.

Figure 6B:
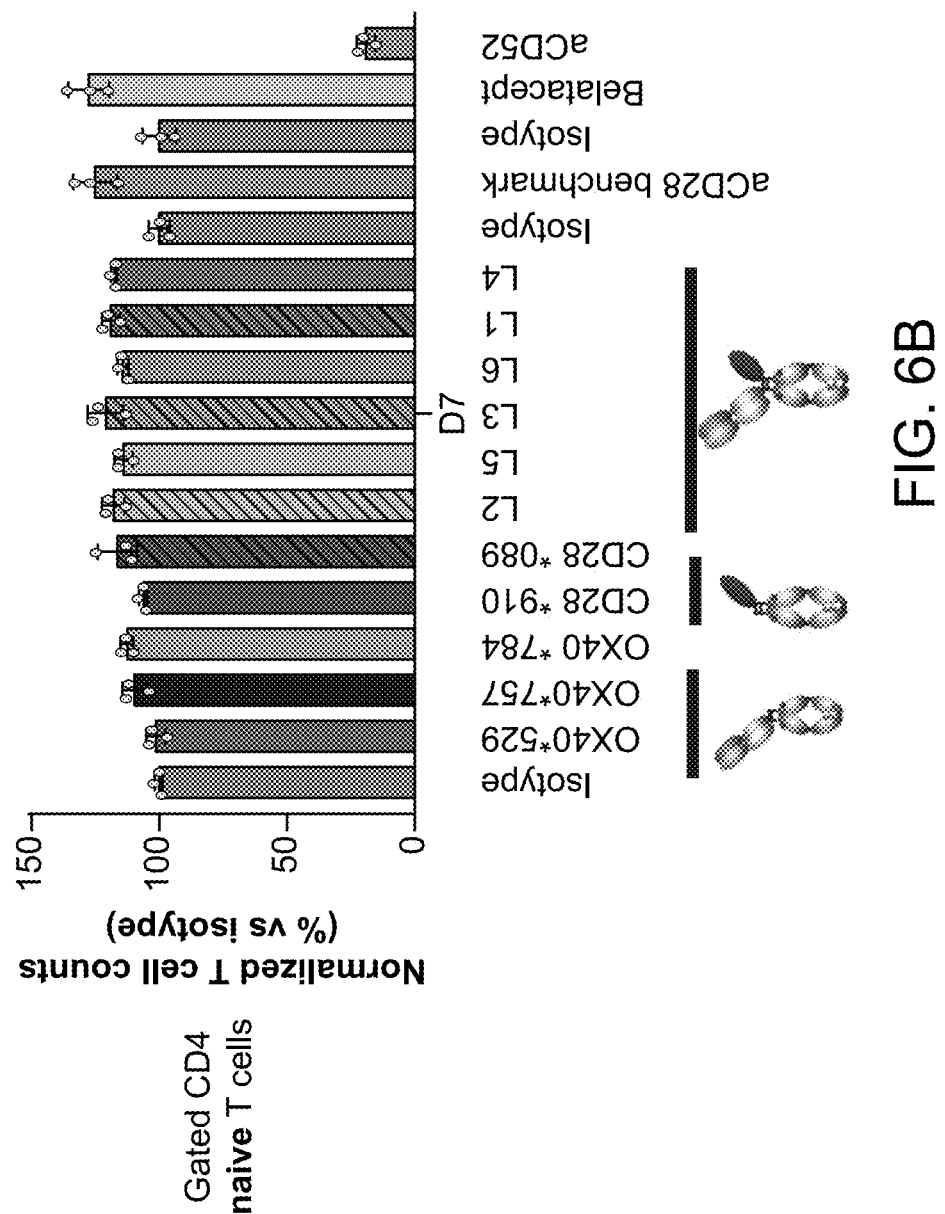
FIG. 6B depicts high selectivity towards effector T cells.
Figure 6C:
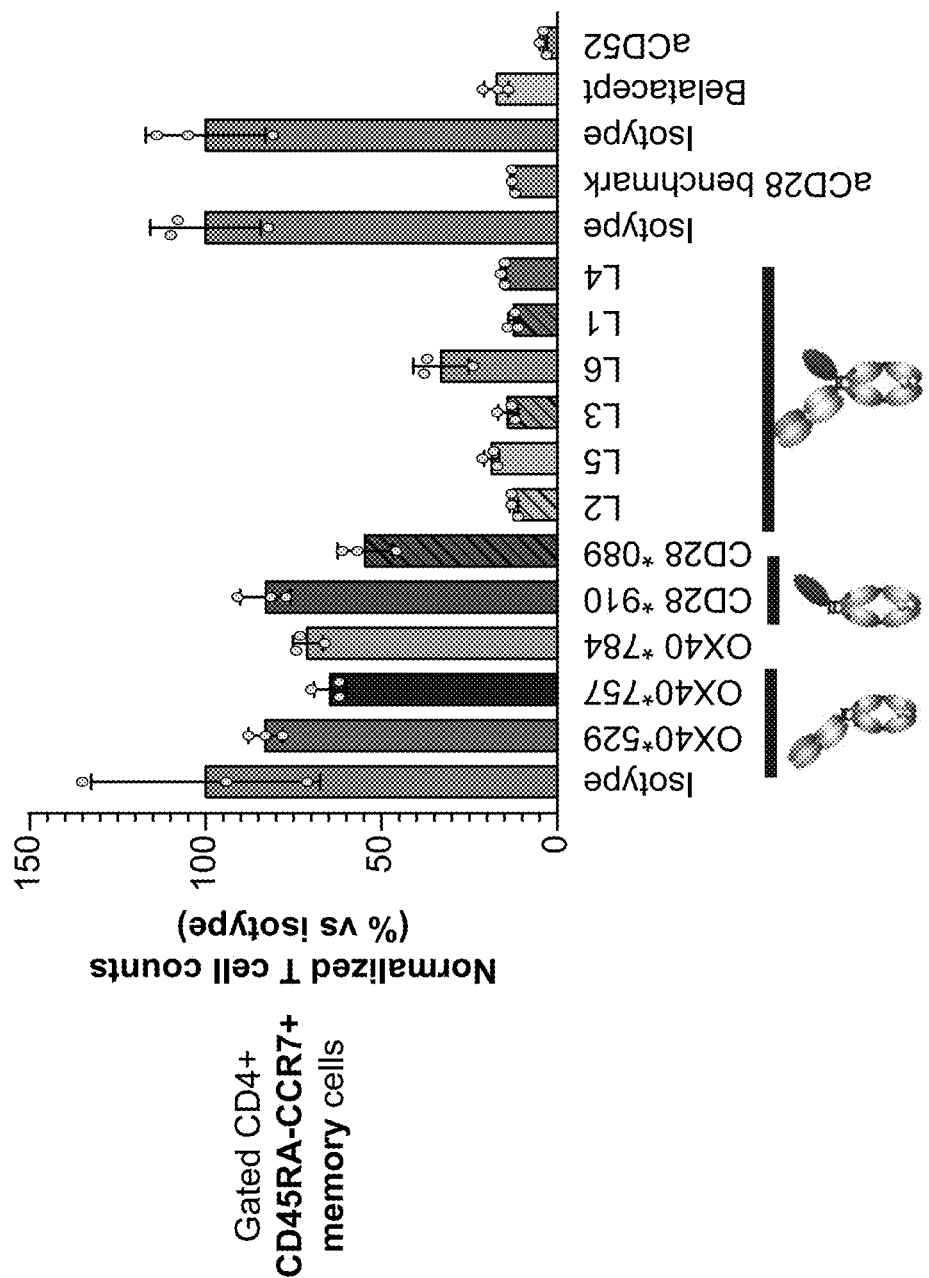
FIG. 6C depicts high selectivity towards memory T cells.

A dose dependent inhibition of cytokines production (e.g. IL-2, IL5, IL13, GMCSF) was measured with bispecific antibodies (12 concentrations of compound tested). High potency (sub-nanomolar EC50) was found for the bispecific antibodies (FIG. 6A). Effect was superior to competitors Abatacept, Belatacept, and benchmark anti-CD28 molecules (FIG. 6A). Furthermore, bispecific antibodies selectively targeted alloreactive memory T-cells expansion, compared to depleting anti-CD52 benchmark antibody (FIG. 6B)

Derp1 Allergen Assay

Figure 7A:
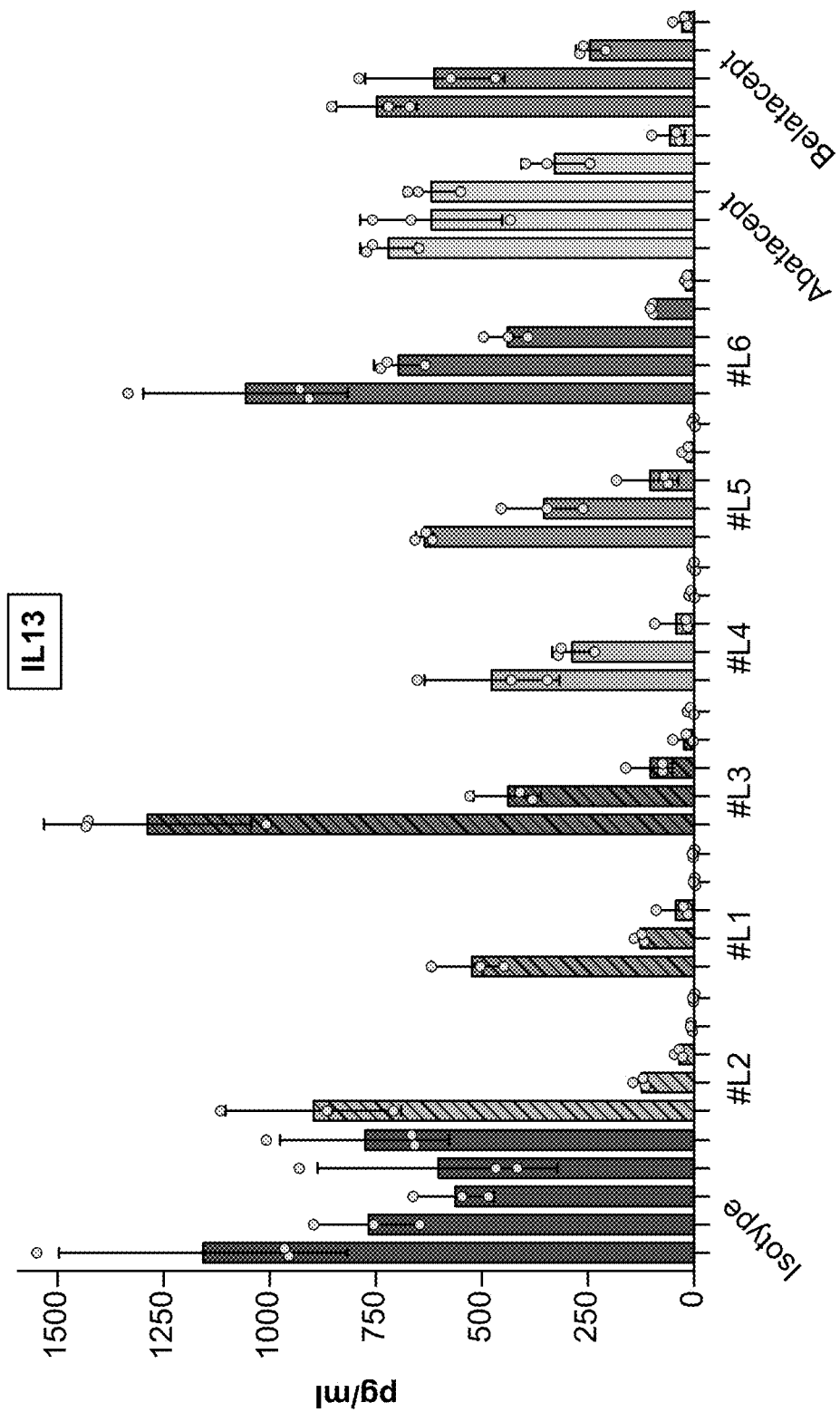
FIG. 7A and FIG. 7B depict results of the inhibitory activity of the bispecific antibodies in a Derp1 antigen recall assay where each bar within a given data set (e.g., #L2, #L1, etc.) represents a serial 1/10 dilution range from 60 nM to 0.006 nM.
Figure 7B:
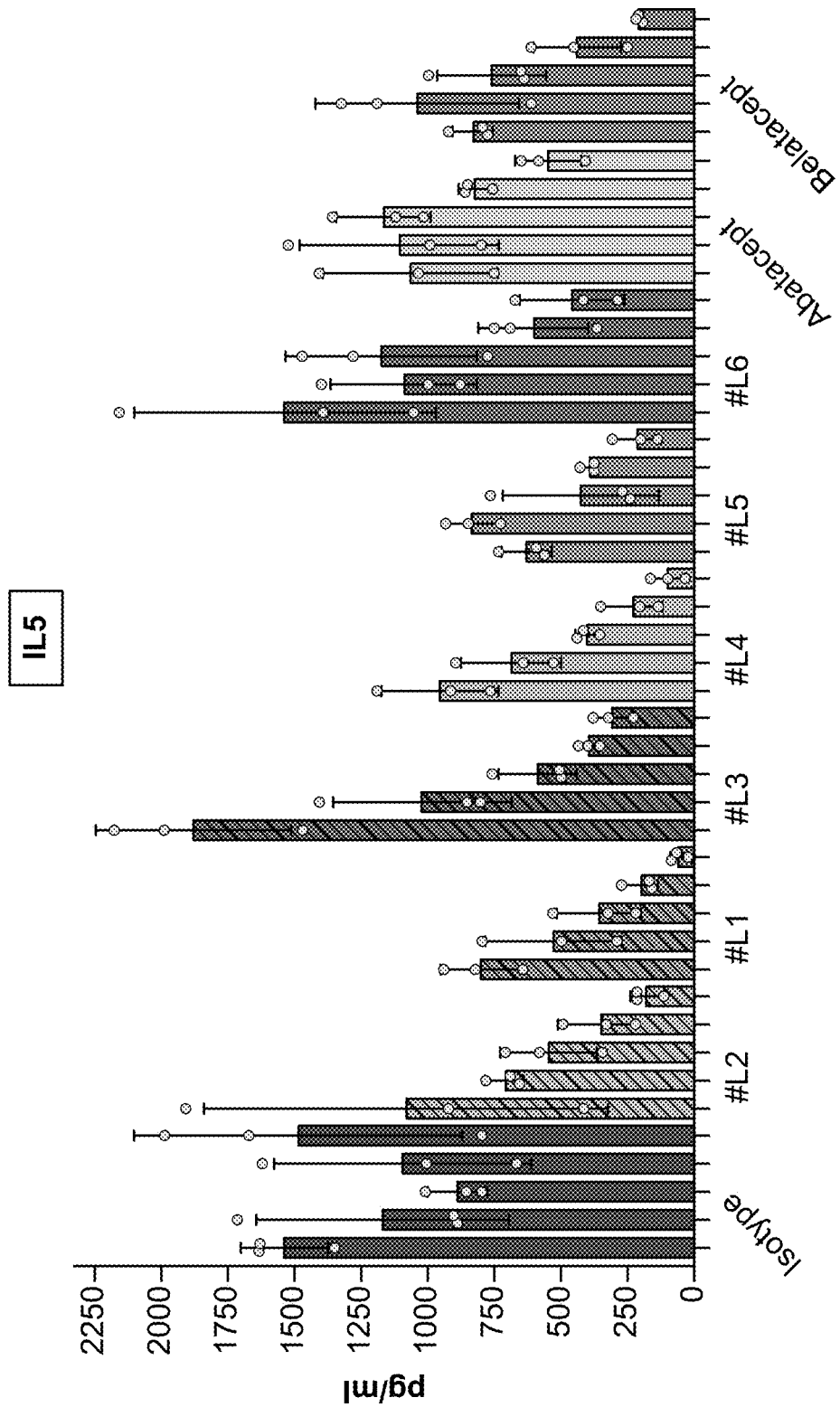

Activity of bispecific antibodies was evaluated in MRC5-PBMCs co-culture system. MRC5 cells were grown in EMEM medium (Sigma 4655) supplemented with 10% FCS, HEPES, NEAA and 1 mM pyruvate sodium. In the experiment, MRC5 cells were dissociated using accutase stempro (Thermofischer), washed and re-seeded overnight at $5.10e^{*5}$ cell/ml in AIMV medium containing 5% Serum replacement (Gibco), in 96-well flat-bottom cell culture plates. In parallel, frozen house-dust mite sensitive PBMCs from 4 different donors were thawed, stained with 5 µM of CFSE and diluted in XVIV015 medium at 4.10e+6 cell/ml. CFSE-stained PBMCs (50 µl) were added to the MRC5 cells (50 ul) in the presence of 50 µl of *Dermatophagoides pteronyssinus* (DerP, Indoor biotechnologies at 3 ug/ml of final concentration) and 50 ul of treatment antibodies (4×). Seven days later, co-culture supernatants were harvested for cytokine measurement (e.g. L-5, IL-13) and cells collected and stained with anti-CD4 and CD8 antibodies to determine the percentage of CFSE-labeled CD4+ and CD8+T cells proliferation. As shown in FIG. 7A and FIG. 7B, each of the bispecific antibodies L1-L6 was capable of repressing IL-5 and IL-13 production.

Antigen (CMV) Recall Assay

Bispecific antibodies were tested in an antigen recall assay using CMVpp65 antigen. Frozen PBMCs from a minimum of 5 donors were thawed and diluted in XVIVO15 medium containing 5 M of CTV. After 10 min of incubation (37° C., 5% CO2), cells were centrifuged (400 g, 5 min) and seeded in 96-well U-bottom culture plates (Thermofisher) at $2 \times 10^5$ cells/well (100 ul), in the presence of 50 µl of CMVpp65 (diluted at 1/250, Miltenyi) and 50 µl of treatment antibodies (at 6 nM final concentration). Five days later, culture supernatants were harvested for cytokine measurement, and at day 7 cells were collected.

Figure 7C:
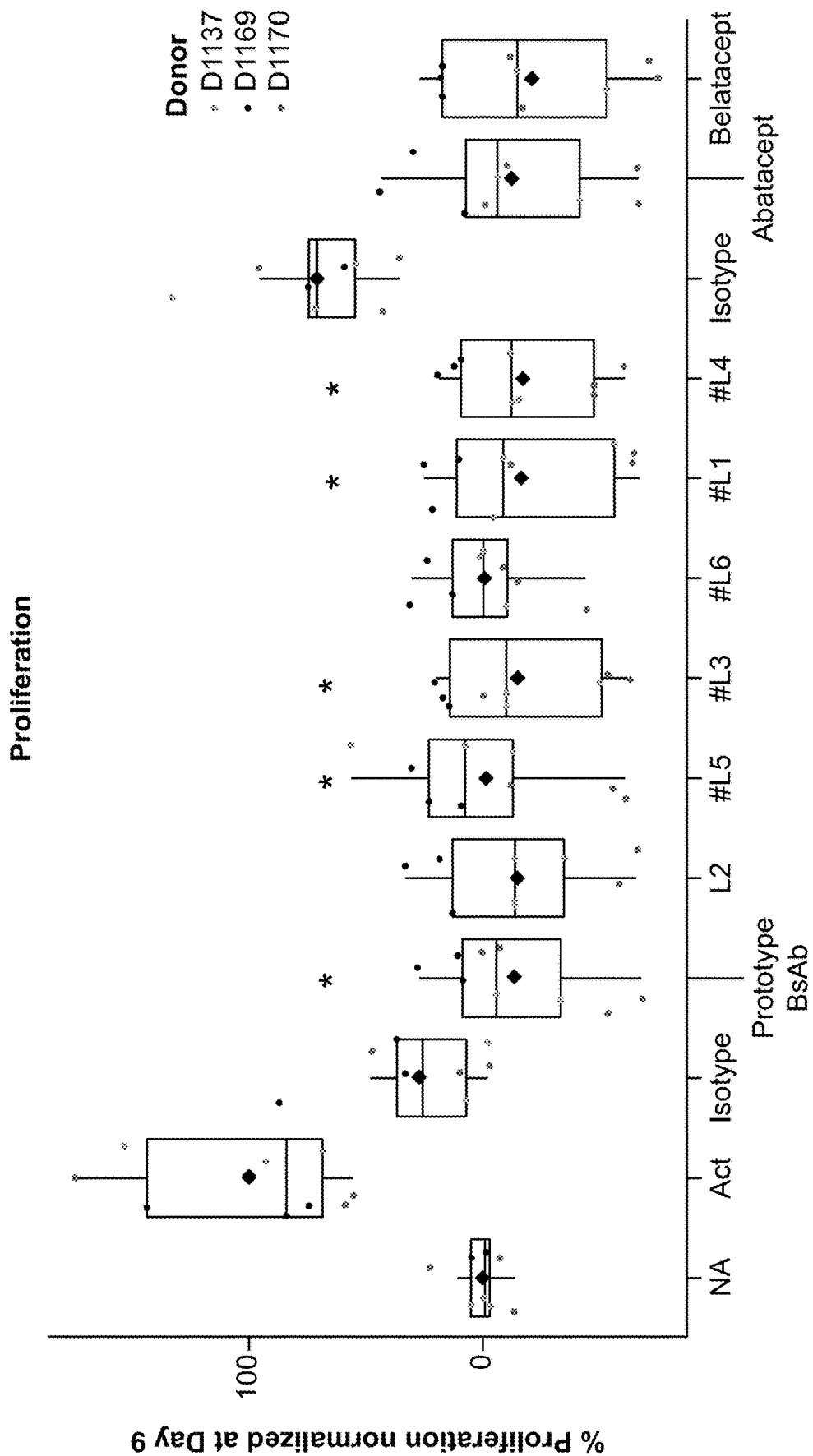
FIG. 7C and FIG. 7D depict results of a CMVpp65 antigen recall assay.
Figure 7D:
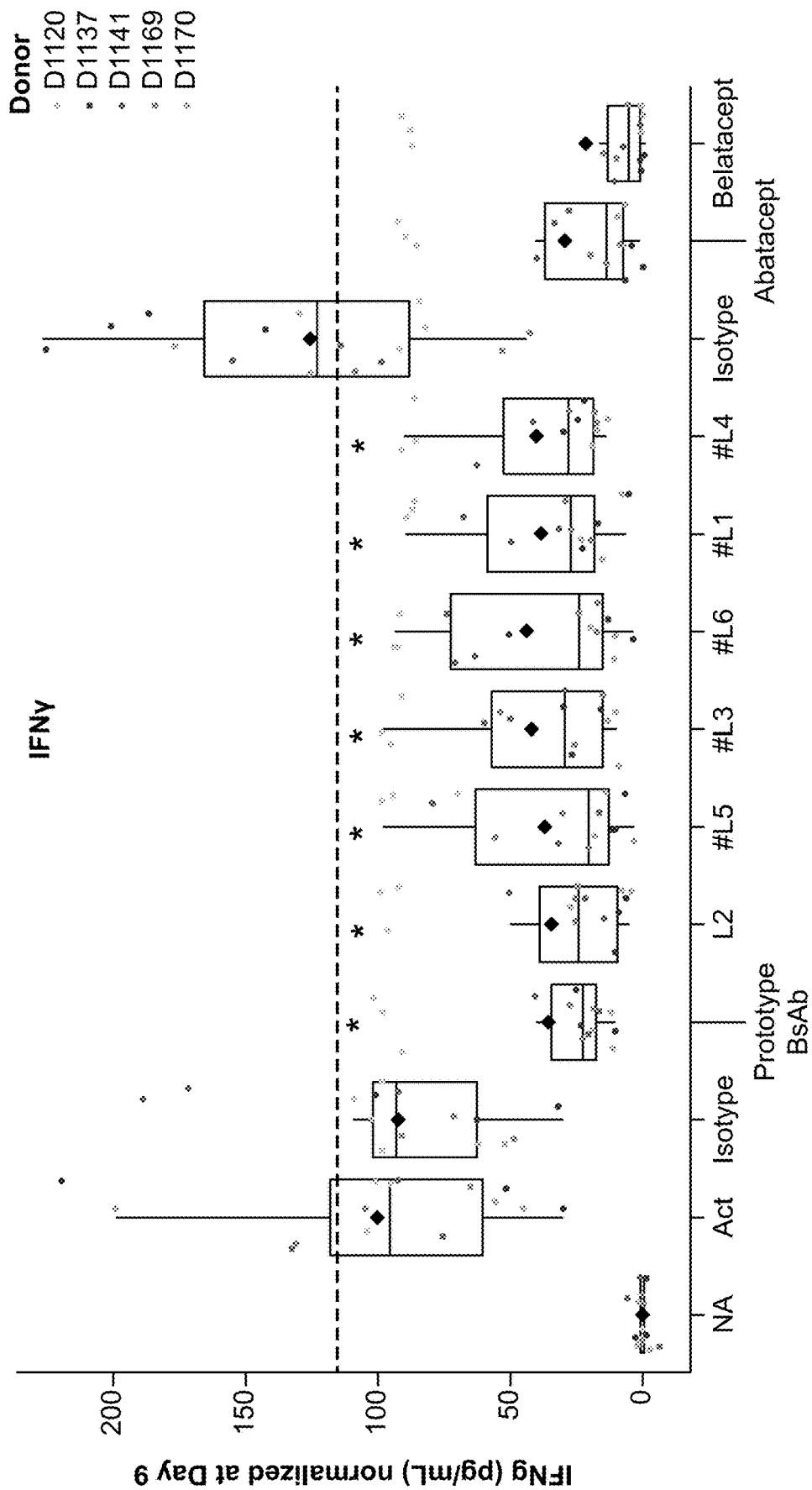

As shown in FIG. 7C and FIG. 7D, each of the bispecific antibodies L1-L6 were capable of repressing IFNγ production and T cell proliferation.

T-Cell Activation Assay

Monoblock for each arm and the bispecific antibodies were tested in T cell activated cells in presence of anti CD3 Abs. U-bottom 384-well plates were coated with 5 µg/mL anti-human CD3 antibody (eBiosciences, 15288347, OKT3 clone) overnight at 4° C. Plates were washed in PBS and 50,000 T cells were added in complete X-VIVO 15 culture media (Lonza, BE02-060F) in the presence of 10, 30, and 100 nm of negative and positive control antibodies or test compounds and incubated at 37° C. in a 5% $CO_2$ incubator. After 6 days of incubation, supernatants were collected and stored at −20° C. until cytokine measurement. Promega CELLTITER-GLO reagent was added to the cells for cell counting. Cytokine levels were measured using a Homogeneous Time Resolved Fluorescence human IFNγ/tumor necrosis factor (TNF) α cytokine kit according to the manufacturer's instructions (Cisbio). Samples were read on the PHERAstar FSX multimode reader (BMG Labtech). Data were expressed as percentage of effect compared with isotypic control. No enhancement of either T cell proliferation and cytokine secretion (IFNg, TNFa) was measured.

MIMIC-Based Cytokine Release Assay (MIMIC-CRA)

A MIMIC-based CRA assay was used for its sensitivity to detect CD28 agonistic activity and conducted as described by Dhir et al. (J Immunotoxicol. 2012. 9(1):34-42). Reconstituted leukocytes and autologous platelet poor plasma were derived from 10 independent donors. Test items at six different concentrations and controls were added for 24 hours before supernatants were harvested for multiplexed cytokine analysis by Luminex.

As shown in FIG. 13A-FIG. 13F, the bispecific antibodies L1-L6 each did not stimulate the production of pro-inflammatory cytokines TNFα, IFNγ, IL-2, IL-5, IL-6, or IL-10.

Anti-CD3 Pre-Activated PBMC-Based CRA Assay (PBMC-CRA)

An anti-CD3 pre-activated PBMC-based CRA assay was used to induce OX40 expression and thereby allow detection not only of CD28 but also OX40 agonistic activity in the same assay. Cryopreserved PBMC from 12 independent donors were plated at $2 \times 10^6$ cells per 96 well in serum free medium containing 500 ng/mL anti-CD3 antibody (clone UCHT1) for 24 hours. Test items at six different concentrations and controls were added for another 24 hours before supernatants were harvested for multiplexed cytokine analysis by Luminex.

As shown in FIG. 13G-FIG. 13N, no significant induction of proinflammatory cytokines over anti-CD3 control was observed for any of the bispecific antibodies L1-L6.

High-Density PBMC Assay

To evaluate the propensity of the bispecific antibodies to induce cytokine release via its anti-CD28 portion, a High-density PBMC assay (HDPBMC) described by Romer et al. in 2011 (Blood) was used. Briefly, frozen PBMCs from a minimum of 8 healthy donors were thawed and pre-cultured for 2 days in a 24-well culture plate at $10 \times 10^6$ cells/ml, in complete RPMI 1640 L-Glutamine medium per well (RPM11640 L-Glutamine+10% FCS, Penicillin/Streptomycin, nonessential amino acids, sodium pyruvate). Cells were then collected, centrifuged (5 min 400 g 4° C.) and cultured in a complete AIMV medium at 200000 cells/well in 96-well flat-bottom cell culture plates (TPP, 150 ul of cells per well) in the presence of 50 µl of bispecific antibodies or control antibodies at final concentration of 60 or 6 nM diluted in complete AIMV medium. OKT3 and the superagonist anti-CD28 TGN1412 were used as positive control mAbs and murine IgG2a, Human IgG1 and IgG4 mAbs were used as isotype controls. One day later, culture supernatants were collected and analyzed for the presence of cytokines (IL-2, IL-6, IL-10, IFNg and TNFa) using BD™ Cytometric Bead Array Flex following manufacturer's instructions.

Treg-Mediated Suppressive Assay

The potential of the bispecific prototype antibody to enhance the suppressive function of Treg cells was evaluated in a suppressive assay, in which isolated Treg, CD4+ Teff cells and matured monocyte-derived DCs were co-cultured for 6 days.

Human monocyte-derived DCs were generated and matured for 3 days as described in Example 4 (MLR). Frozen Treg and CD4+ Teff cells (previously isolated from human PBMCs) were thawed and labeled with 5 M of CFSE and Cell Trace Violet, respectively. After 10 min of incubation at 37° C. (5% CO2), labeled cells were washed and counted. MoDC and CD4+ Teff cells were co-cultured in 96-round bottom plates at a 1:40 ratio ($1 \times 10^3$ DC for $4 \times 10^4$ CD4+ Teff) in the presence of Treg cells seeded at various CD4+ Teff:Treg ratio, and 60 nM of bispecific prototype or isotype control.

Figure 8:
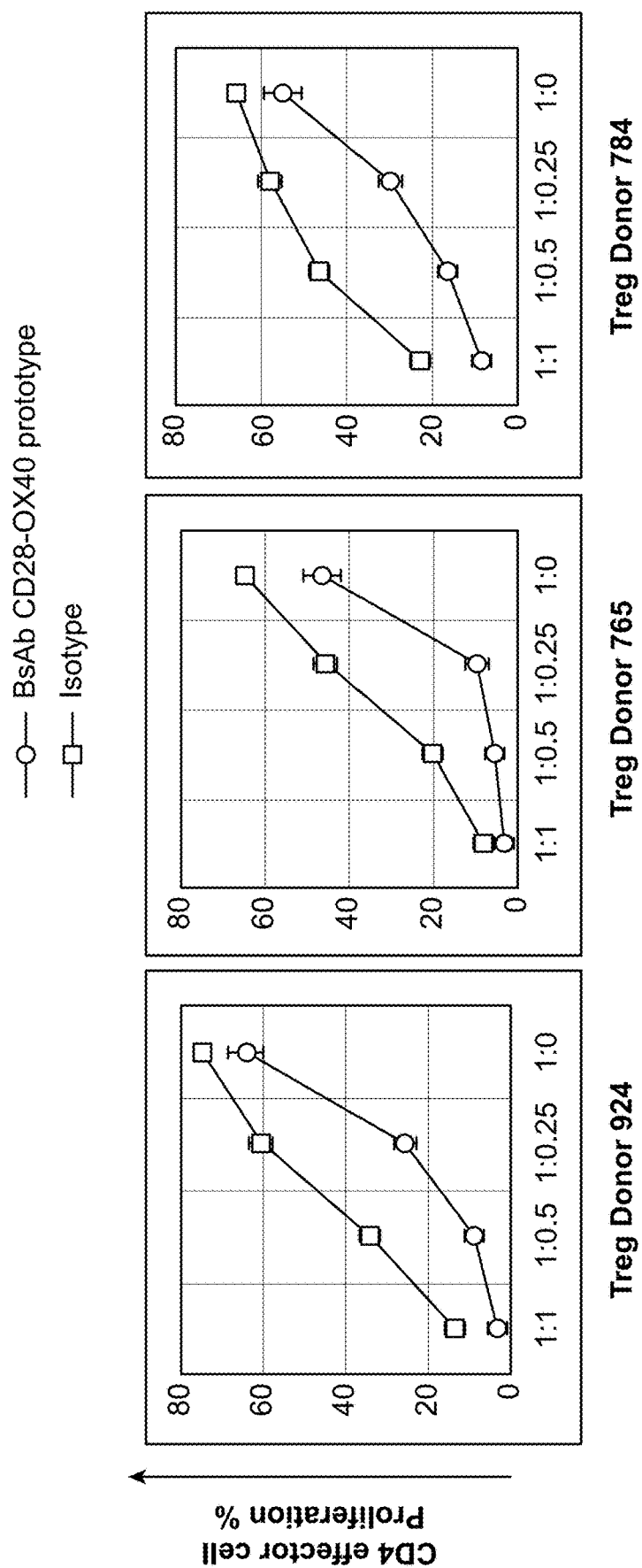
FIG. 8 depicts the ability of the bispecific prototype antibody to enhance the suppressive function of Tregs.

After 6 days of culture, cells were collected and proliferation of the CD4+ Teff cells was assessed by CFSE dilution via flow cytometry. As shown in FIG. 8, the bispecific prototype antibody enhanced the suppressive function of Treg cells.

Figure 3:
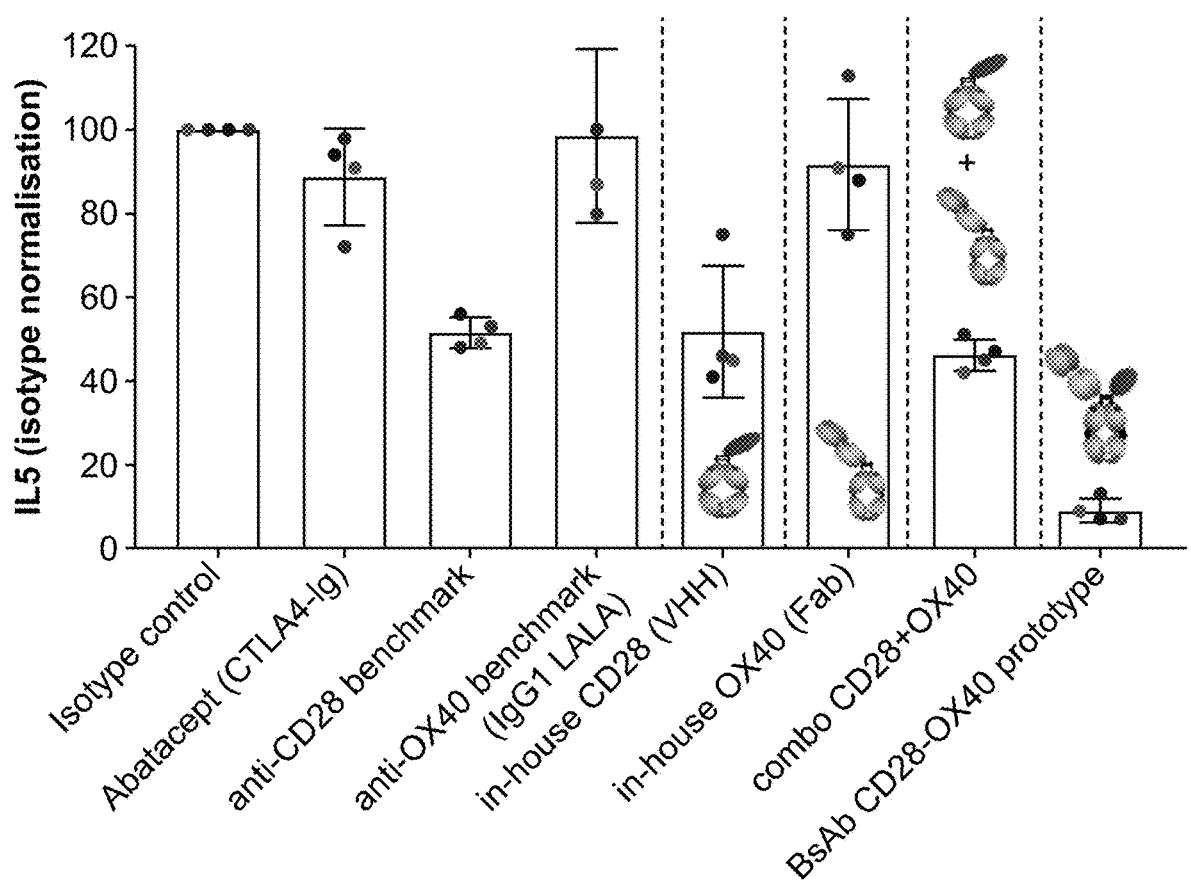
FIG. 3 depicts a comparison of the activity of the bispecific antibody prototype ("BsAb CD28-OX40 prototype") compared to the monospecific antibodies and the combination of the monospecific antibodies in a mixed lymphocyte reaction (MLR) assay.

The bispecific antibody prototype was also compared to monospecific antibodies alone and the combination of the monospecific antibodies in a mixed lymphocyte reaction (MLR) assay. As shown in FIG. 3, the bispecific antibody prototype led to lower IL-15 expression relative to monospecific antibodies alone or the combination of the monospecific antibodies.

Figure 9A:
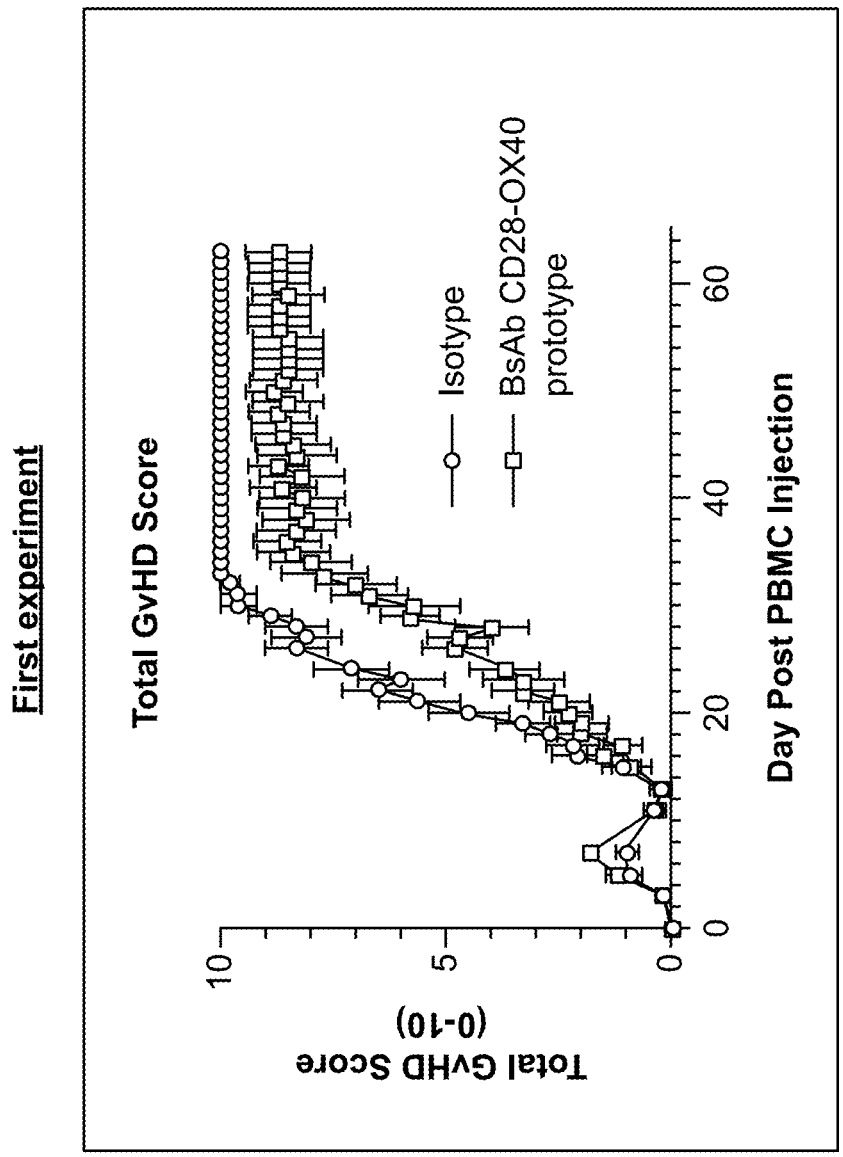
FIG. 9A and FIG. 9B depict the activity of the bispecific prototype antibody in two independent humanized GvHD models.
Figure 9A:
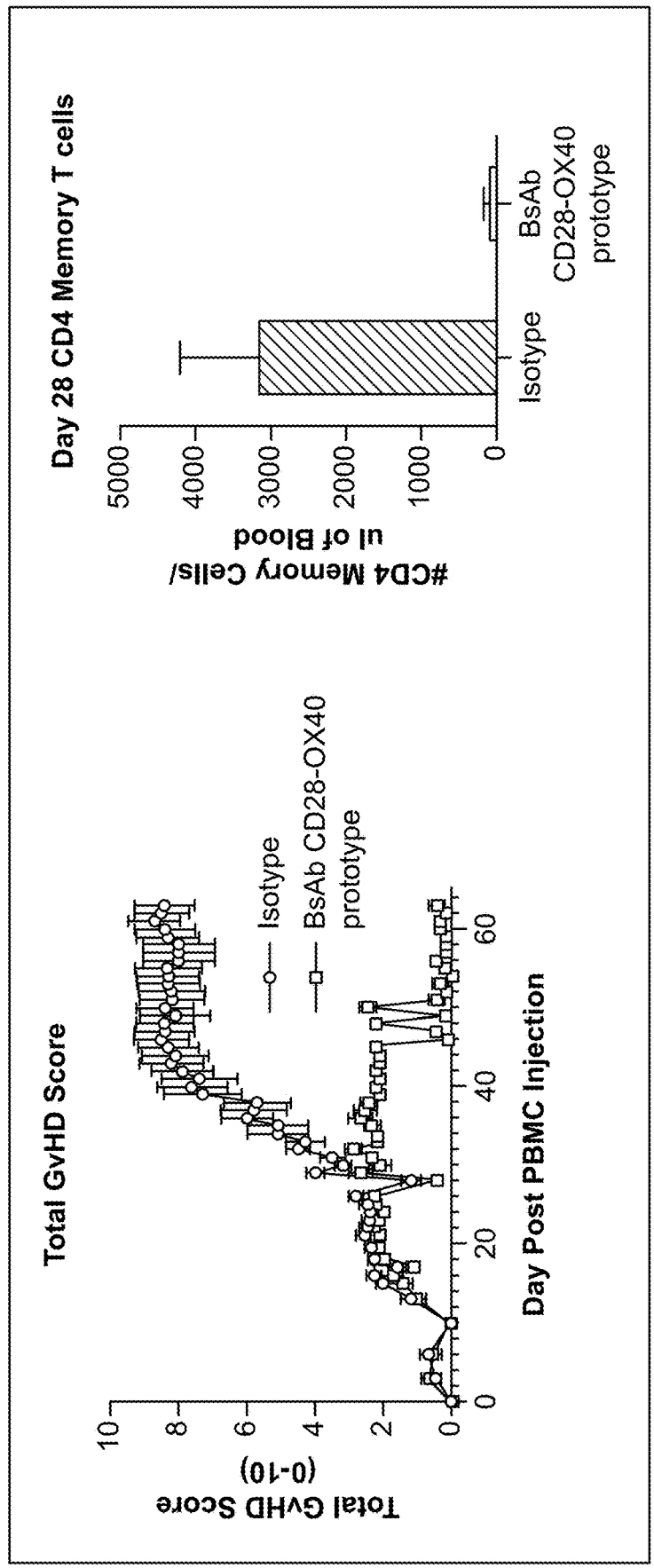
Figure 9B:
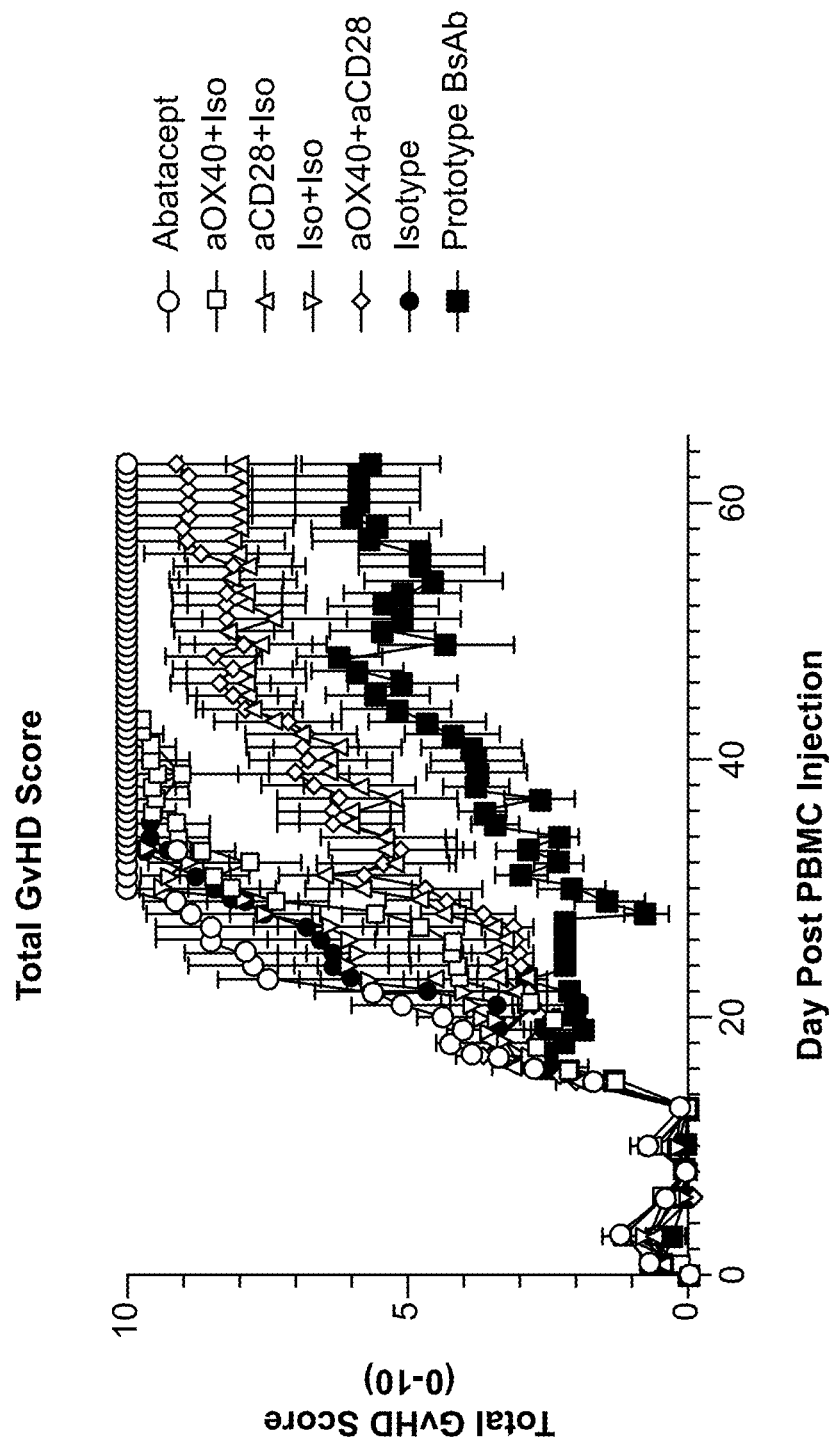
Figure 9C:
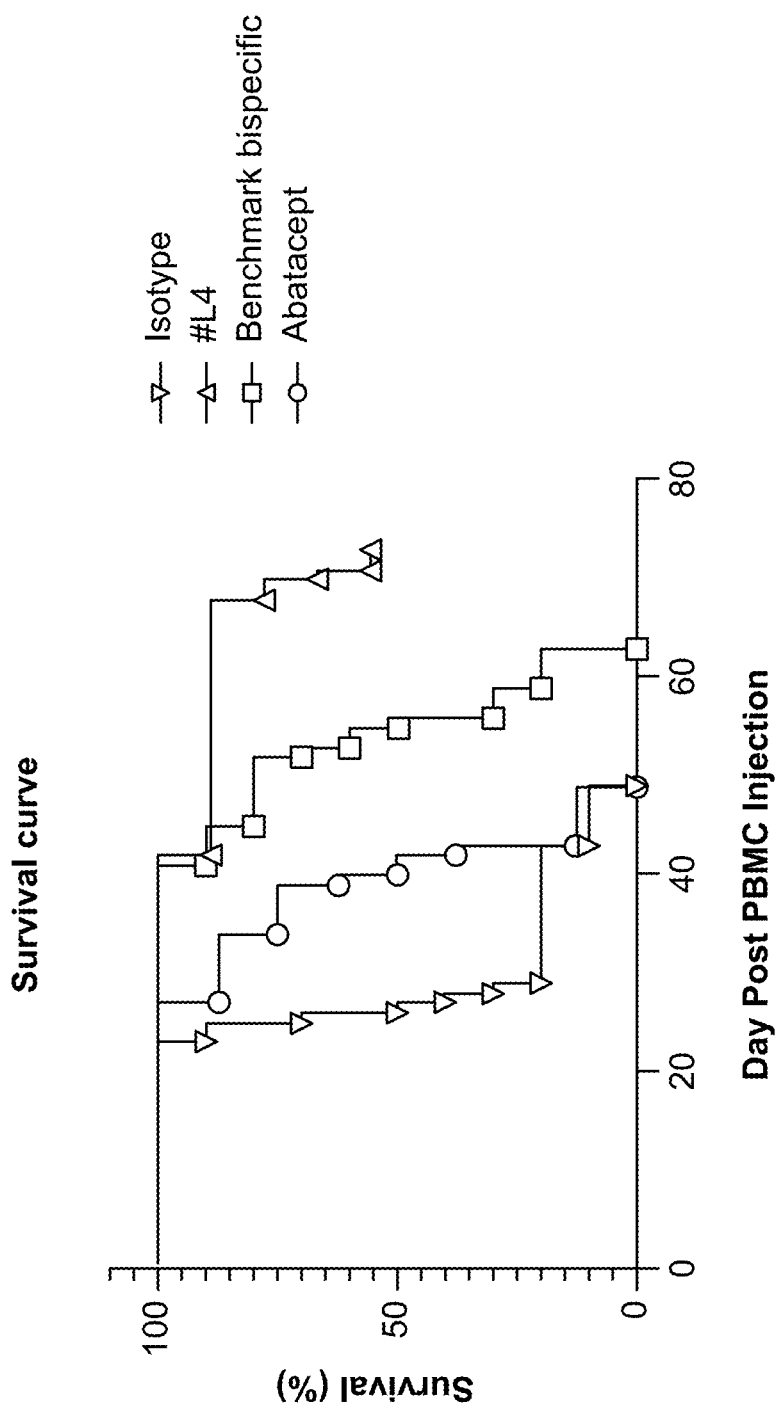
FIG. 9C, FIG. 9D and FIG. 9E depict the survival, GvHD score and body weight loss, respectively, of mice treated therapeutically with the bispecific antibody L4 for a period of 2 weeks.
Figure 9D:
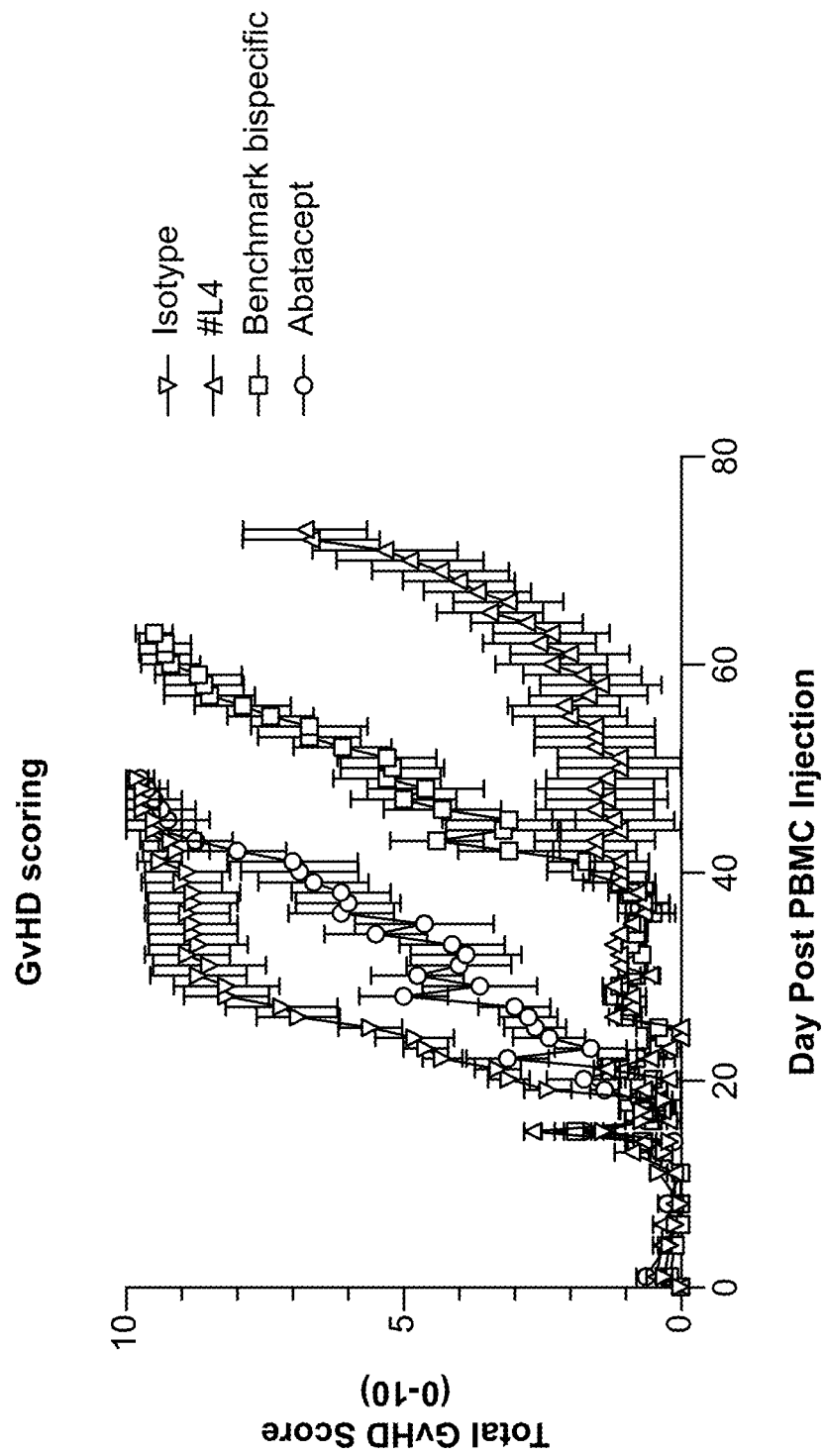
Figure 9E:
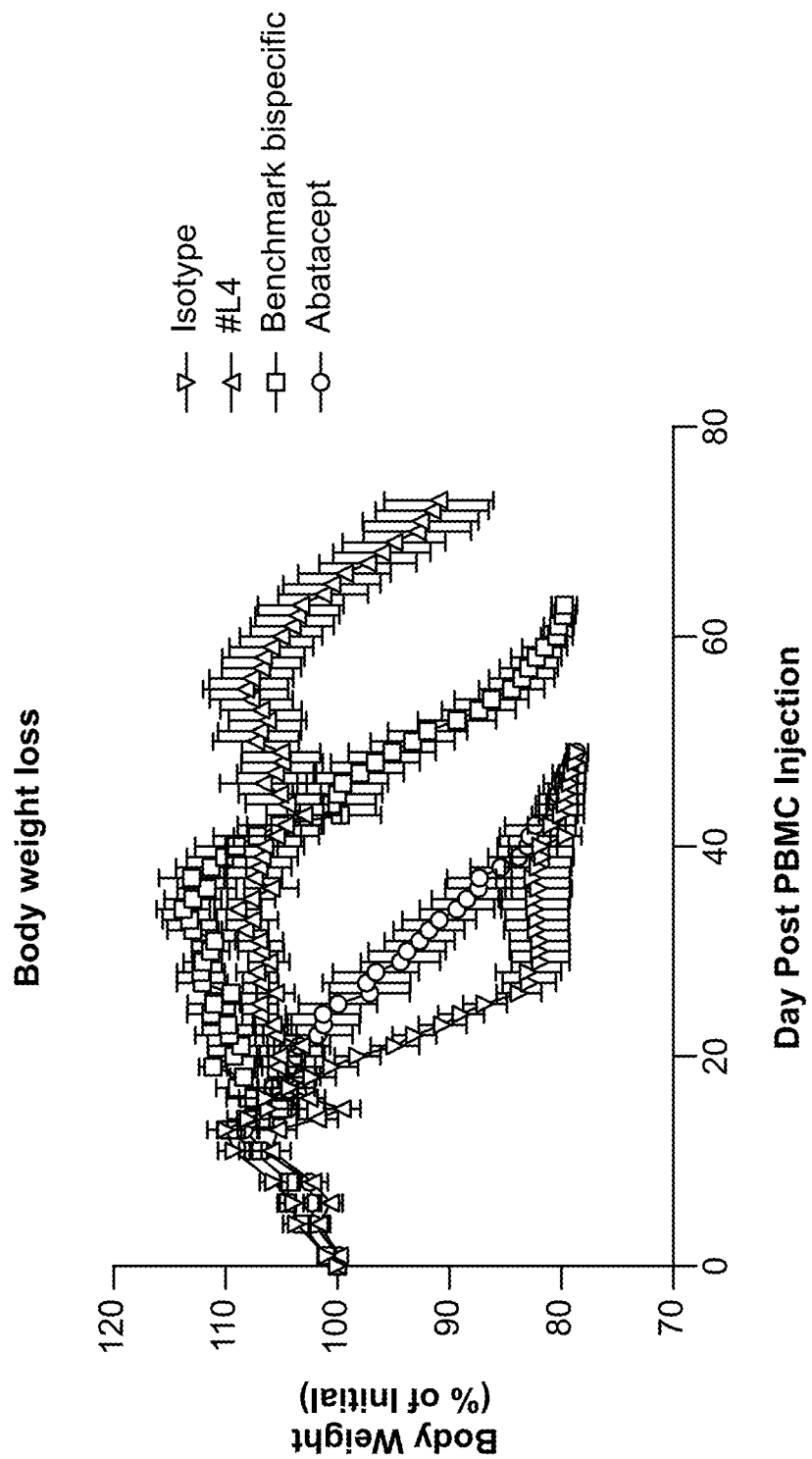
Figure 9F:
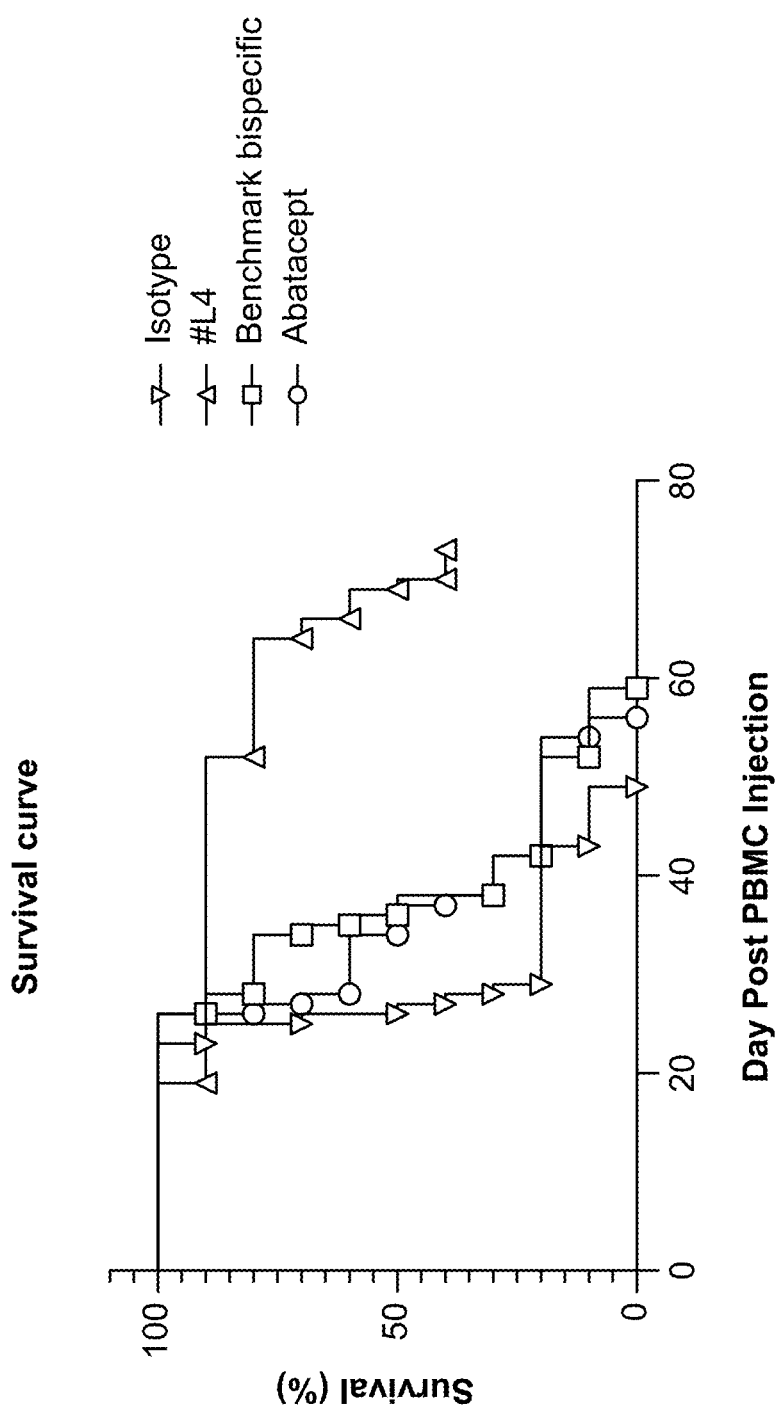
FIG. 9F, FIG. 9G and FIG. 9H depict the survival, GvHD score and body weight loss, respectively, of mice treated therapeutically with the bispecific antibody L4 for a period of 1 week.
Figure 9G:
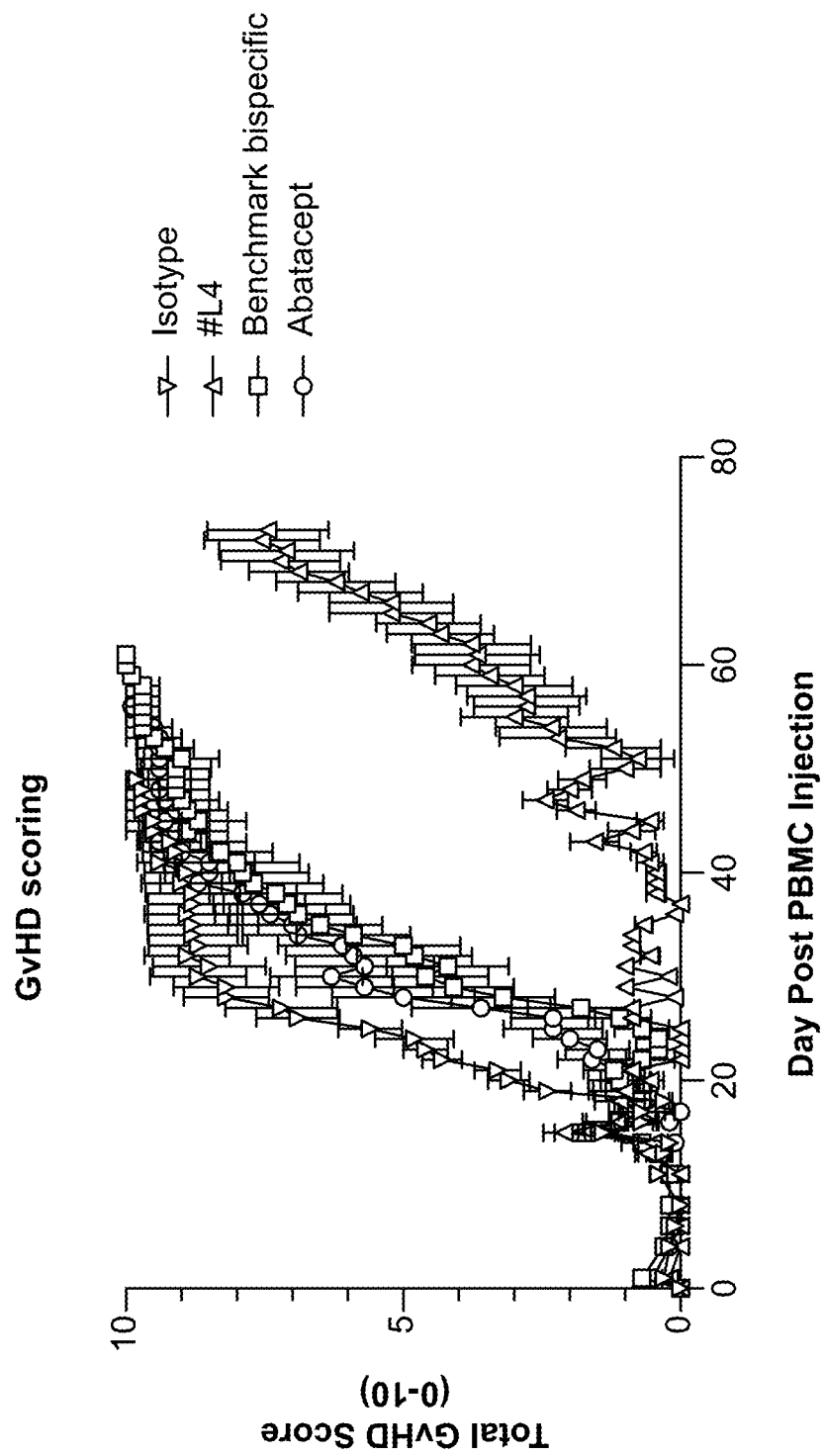
Figure 9H:
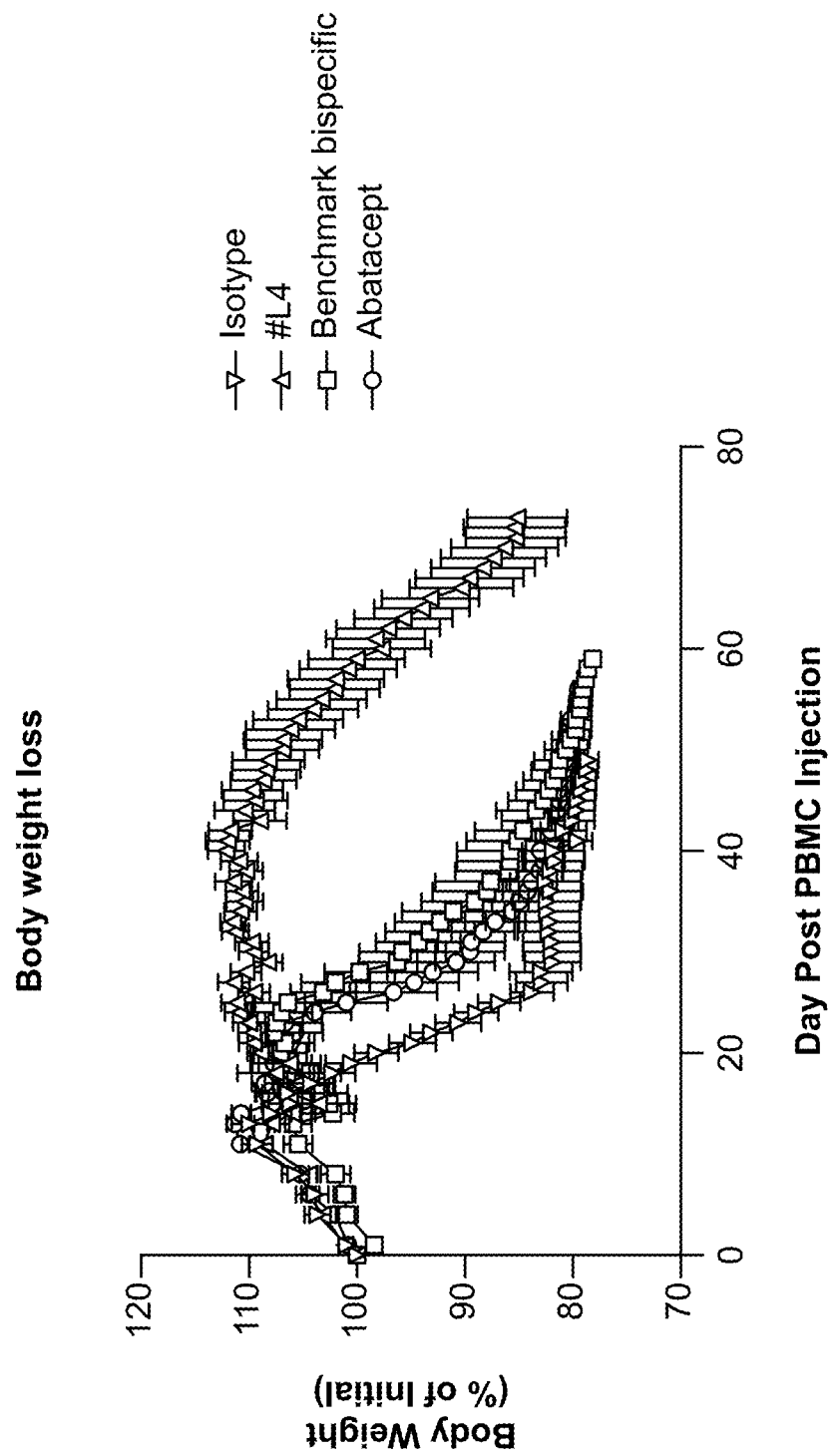

The bispecific antibody prototype was also compared to monospecific antibodies alone and the combination of the monospecific antibodies in humanized GvHD models. As shown in FIG. 9A and FIG. 9B, the bispecific antibody prototype led to a lower GvHD score relative to monospecific antibodies alone or the combination of the monospecific antibodies.

As shown in FIG. 9C to 9H, treatment with the bispecific L4 antibody for either one (FIG. 9C to FIG. 9E) or two weeks (FIG. F to FIG. 9H) was sufficient to reduce GVHD progression for each of the measured endpoints.

ADCC and CDC Activity

ADCC

ADCC assays were conducted using Jurkat and HEK293 stably expressing huOX40 as target cells and human PBMCs as effector cells. HEK-OX40 and Jurkat OX40 cells (target cells) were diluted in a solution with calcein (RPM11640 WO red phenol 1% FCS and 10 ug/ml of calcein (Invitrogen, C3100MP)) and incubated for 10 min at 37° C. Cells were then washed and incubated with serially diluted bispecific antibodies or control antibodies in an ADCC medium (RPM11640 WO phenol red, 1% FCS and probenecid 1x) for 30 min at 4° C. Calcein-labeled cells were then seeded in a 96 round-bottom culture plate containing PBMCs previously activated overnight with 20 ng/ml of recombinant huIL-15 ($1 \times 10^4$ target cells+$2.5 \times 10^5$ PBMC/well). After incubation for 4 hr at 37° C. in 5% CO2, culture supernatants were harvested and calcein fluorescence was measured using the ENVISION reader (PerkinElmer).

CDC

Human whole blood was collected from different donors in heparin tubes and PBMCs isolated via density gradient centrifugation. These PBMCs were then washed (in RPM11640 10% FCS, centrifugation 30 min RT at 350 g without break) and incubated for 3h30 a 37° C. CO2 5% in the presence of various treatments, with or without 50% serum prepared from allogeneic whole blood (50 µl of PBMCs+50 µl of serum or medium+5 ul of 10x treatment). Cells were subsequently washed twice in PBS (centrifugation for 5 min at 450 g), stained with Fixable Viability Dye eFluor (ebioscience) and with anti-CD3, anti-CD4, and anti-CD8 antibodies (from BD Biosciences) and fixed in a 4% PFA solution for 30 min at 4° C. Fixed cells were then diluted in PBS containing 10% of count bright beads (invitrogen #C36950), washed and acquired using BD fortessa LSR X20 flow cytometer. Absolute numbers of viable CD4+ and CD8+ T cells were calculated.

As shown in FIG. 14A and FIG. 14B, the bispecific antibodies lacked detectable ADCC activity in Jurkat (FIG. 14A) and HEK293 (FIG. 14B) assay systems. As shown in FIG. 14C and FIG. 14D, the bispecific antibodies lacked detectable CDC activity induced in CD4 and CD8 assay systems.

Example 5. In Vivo Activity of the Bispecific Antibodies

Figure 11A:
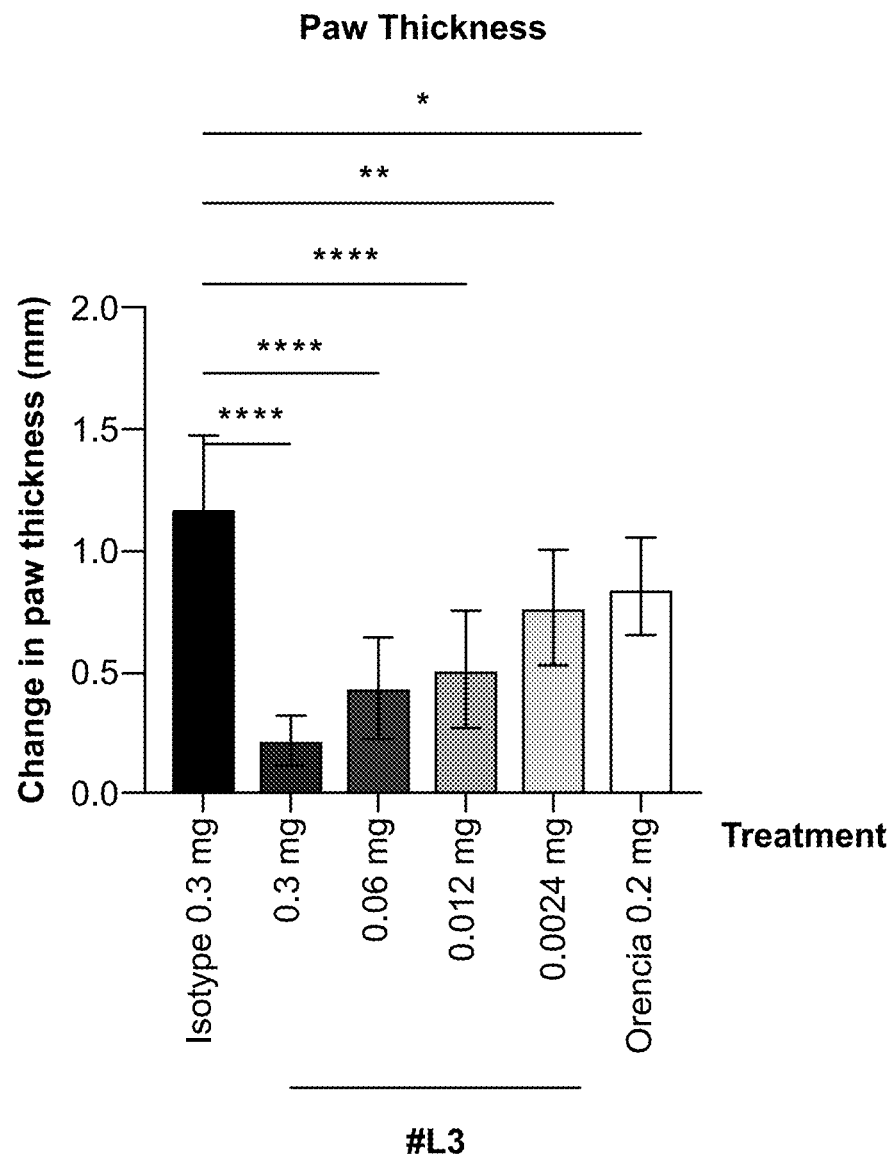
FIG. 11A and FIG. 11B depict the effects of treatment with the bispecific antibodies on paw swelling in two independent DTH models.
Figure 11B:
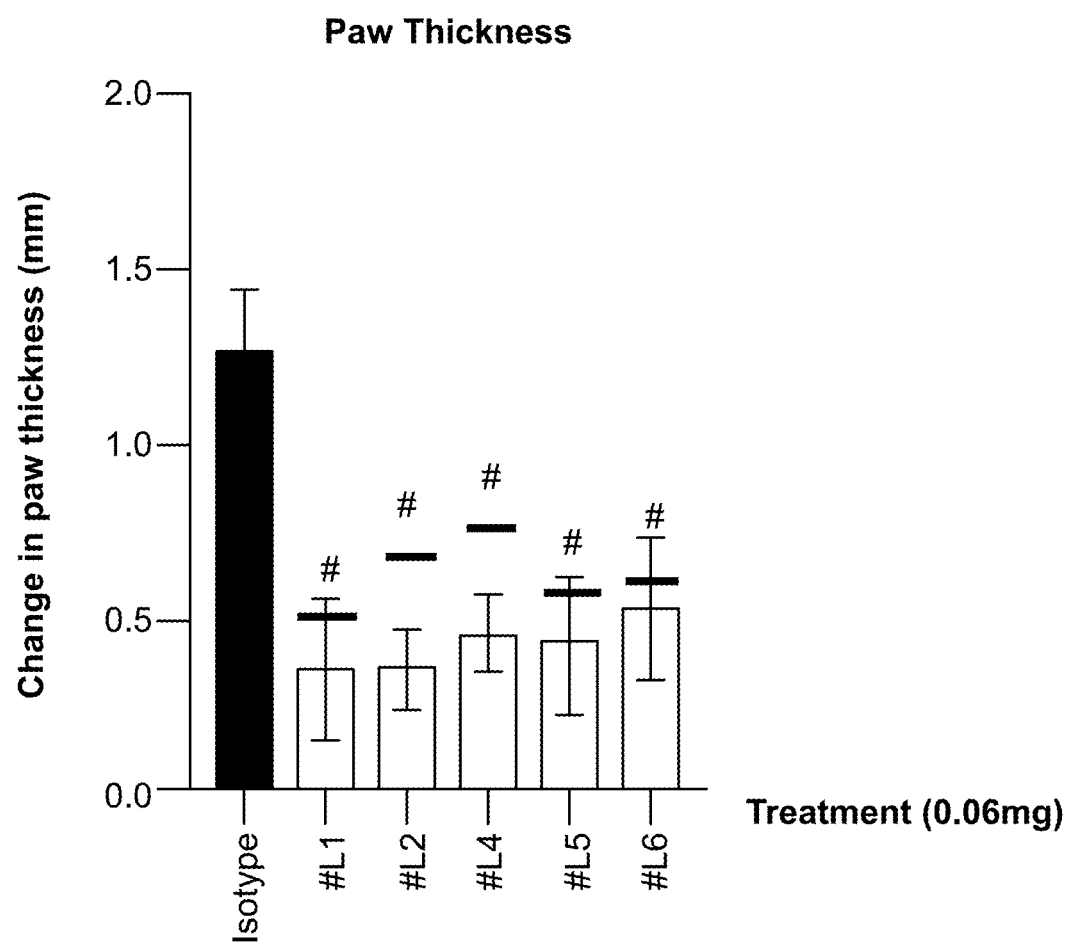

Delayed-Type Hypersensitivity (DTH) is a short-term model for the evaluation of compound effects on cellular immune response. This type of immune response involves mainly T cells rather than antibodies. hCD28/hOX40 double knock-in mice were immunized with methylated bovine serum albumin (mBSA) emulsified in complete Freund's adjuvant (CFA). Five days after immunization, mice were challenged in one hind foot pad with soluble mBSA. Paw thickness was measured just before challenge and 24 hours after the challenge to determine the amount of swelling. The bispecific antibodies were administered subcutaneously on Days 3 and 5 and showed a significant reduction in paw swelling compared to isotype control (FIG. 11A and FIG. 11B).

Figure 12A:
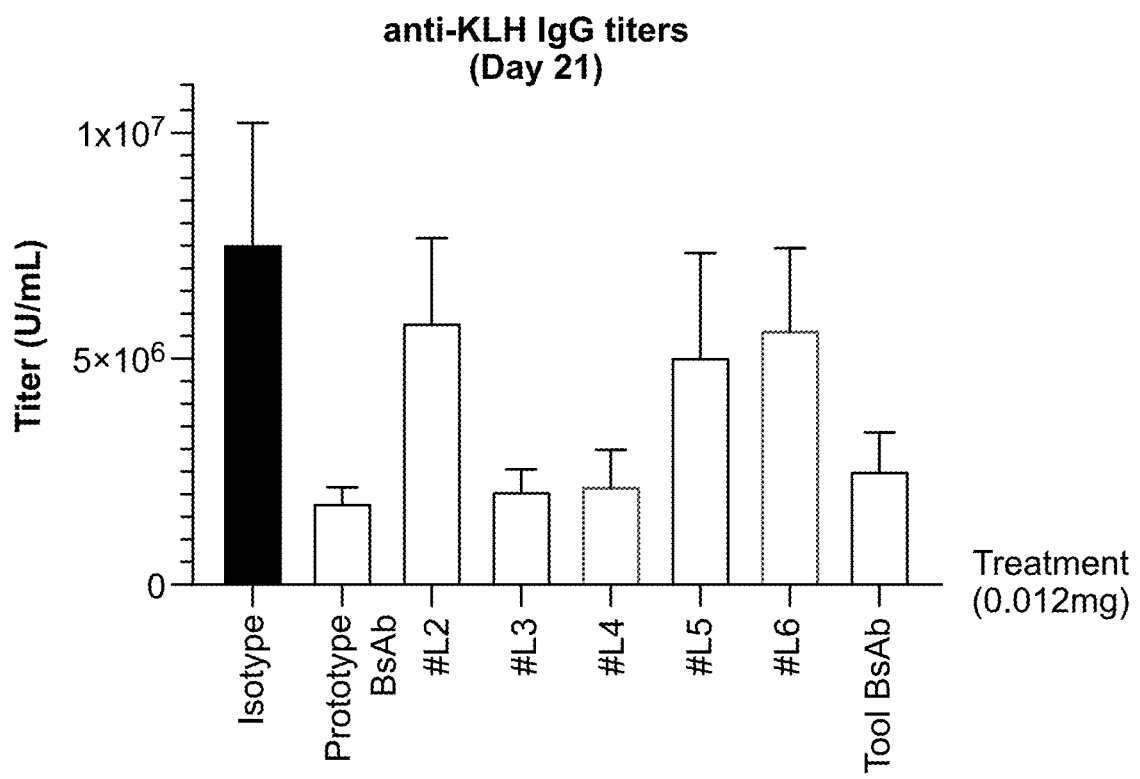
FIG. 12A and FIG. 12B depict the activity of the bispecific antibodies in two independent TDAR models.
Figure 12B:
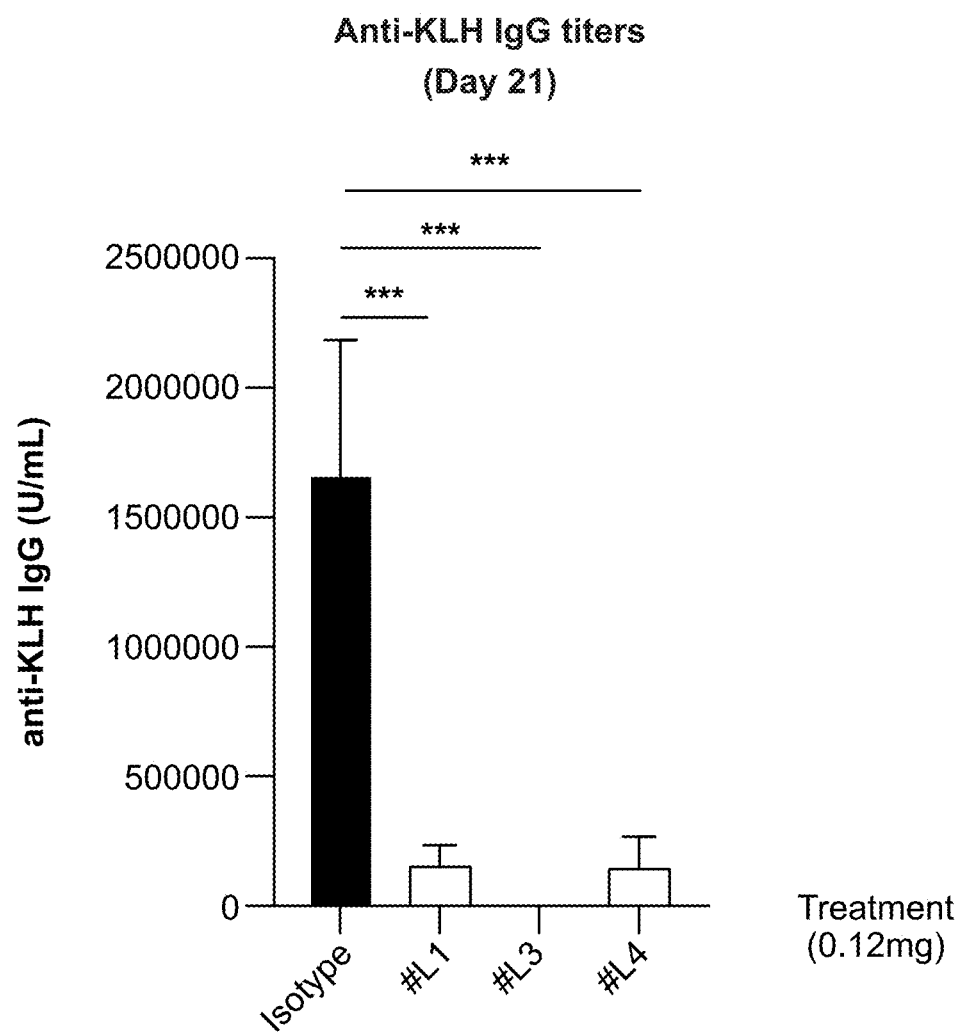
Figure 13A:
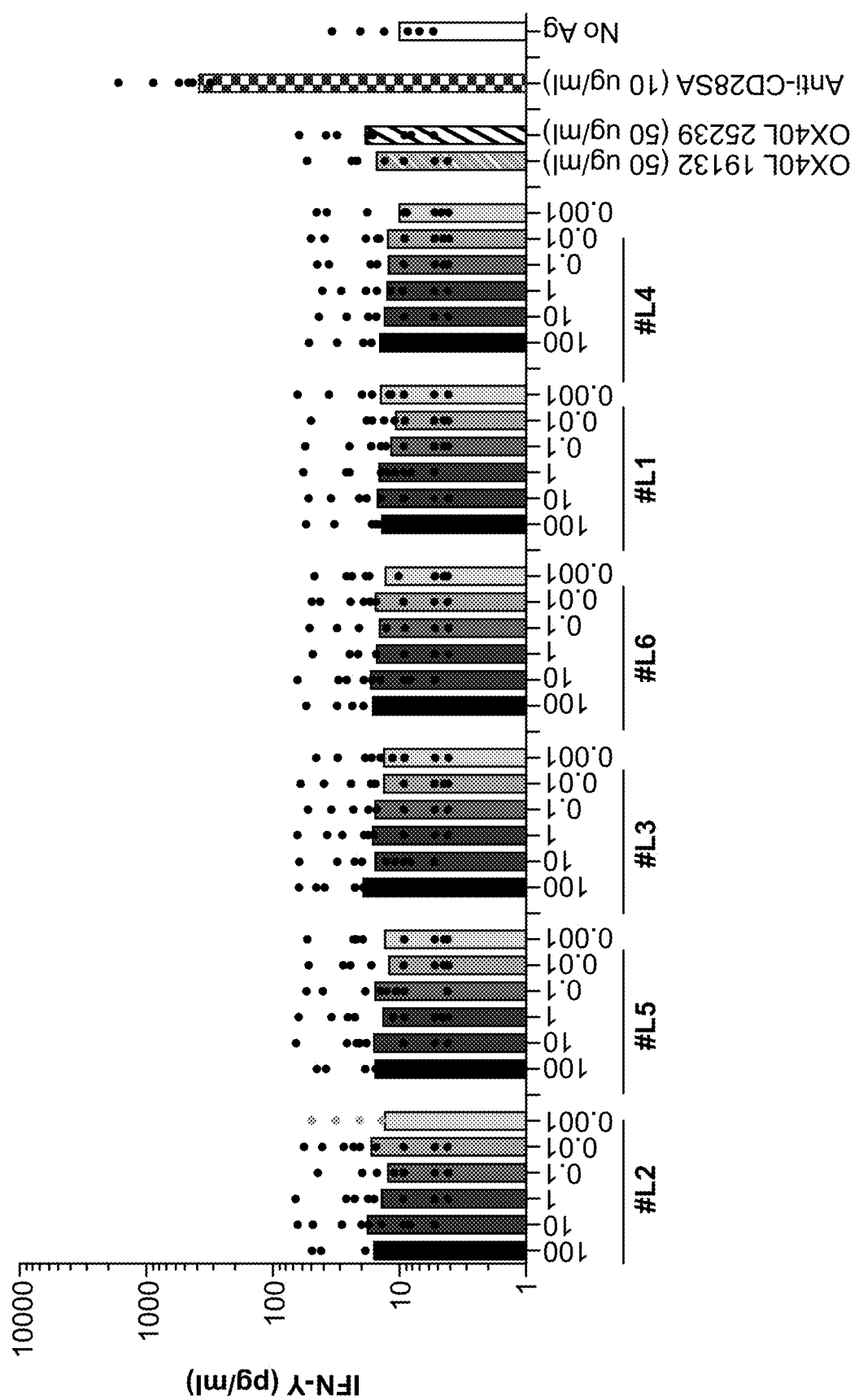
FIG. 13A (IFN-γ), FIG. 13B (IL-10), FIG. 13C (IL-2), FIG. 13D (IL-6), FIG. 13E (TNF-a), and FIG. 13F (IL-5) depict the lack of agonistic activity of the bispecific antibodies as measured in the MIMIC-based CRA assay.
Figure 13B:
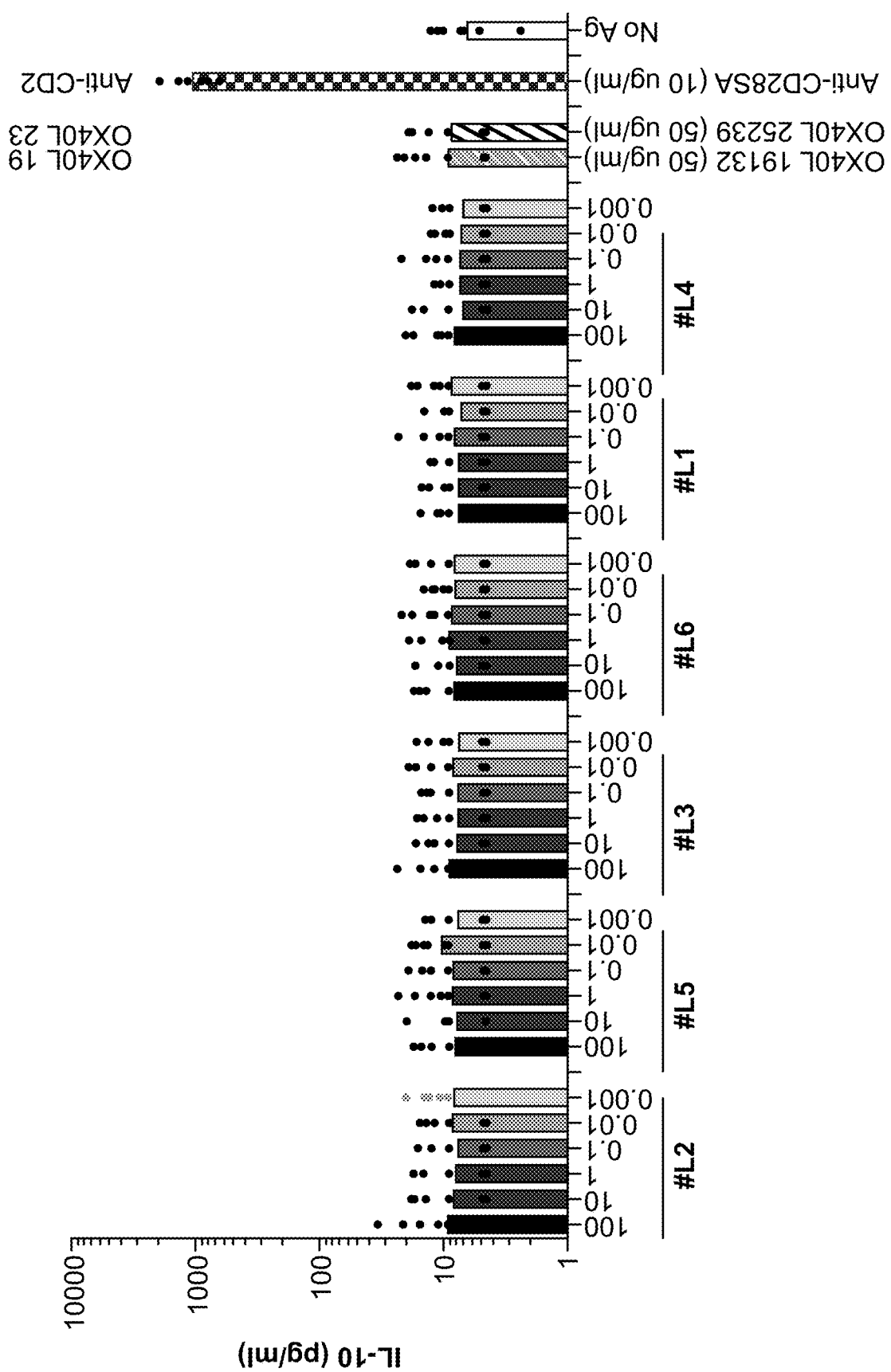
FIG. 13G (IFN-γ), FIG. 13H (IL-2), FIG. 13I (IL-4), and FIG. 13J (MIP1-b) depict the lack of agonistic activity of the bispecific antibodies as measured in an anti-CD3 pre-activated PBMC assay.
FIG. 13K (TNF-a), FIG. 13L (IL-2), FIG. 13M (IL-6), and FIG. 13N (IFN-γ) depict the lack of agonistic activity of the bispecific antibodies as measured in a high-density PBMC assay.
Figure 13C:
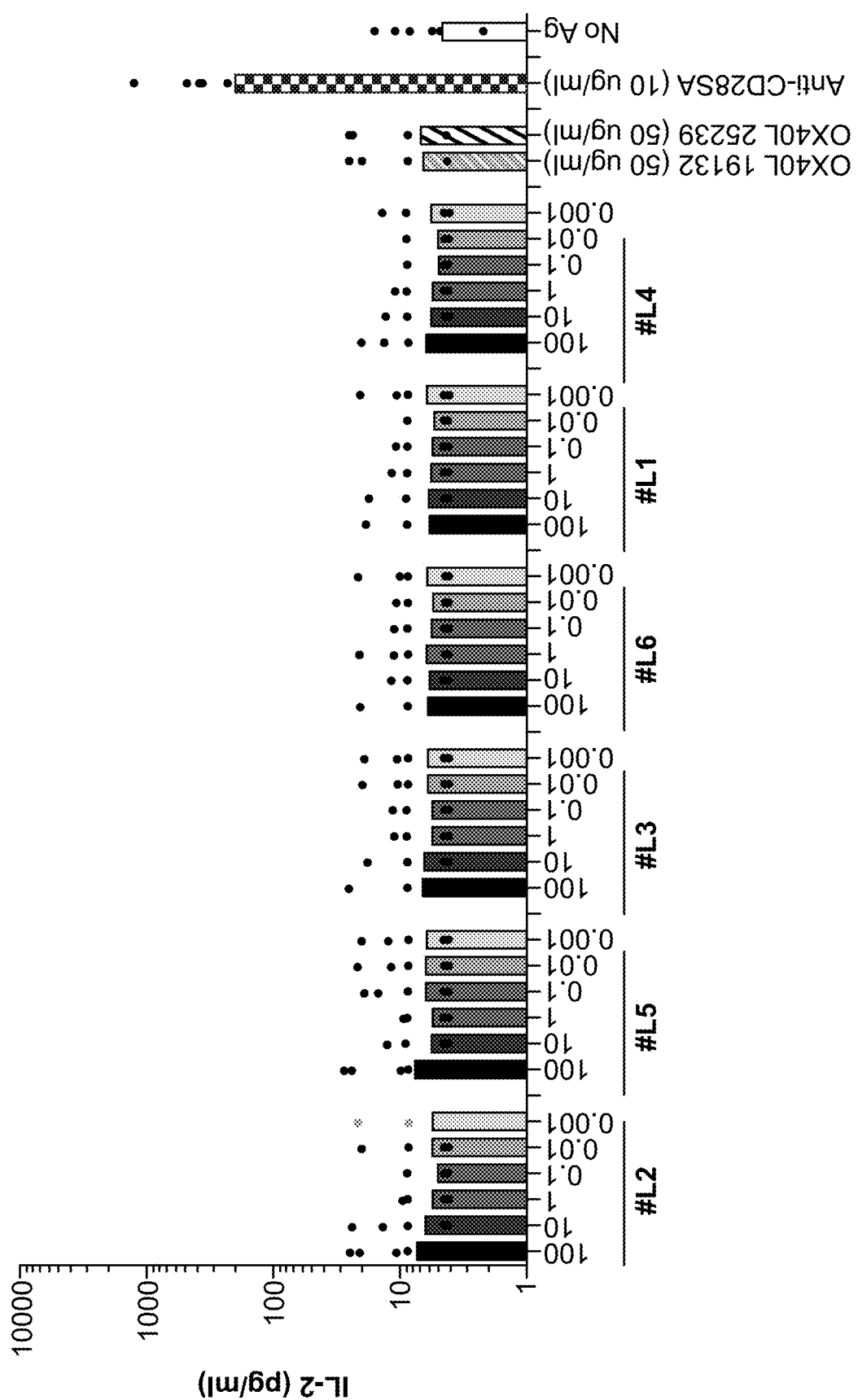
Figure 13D:
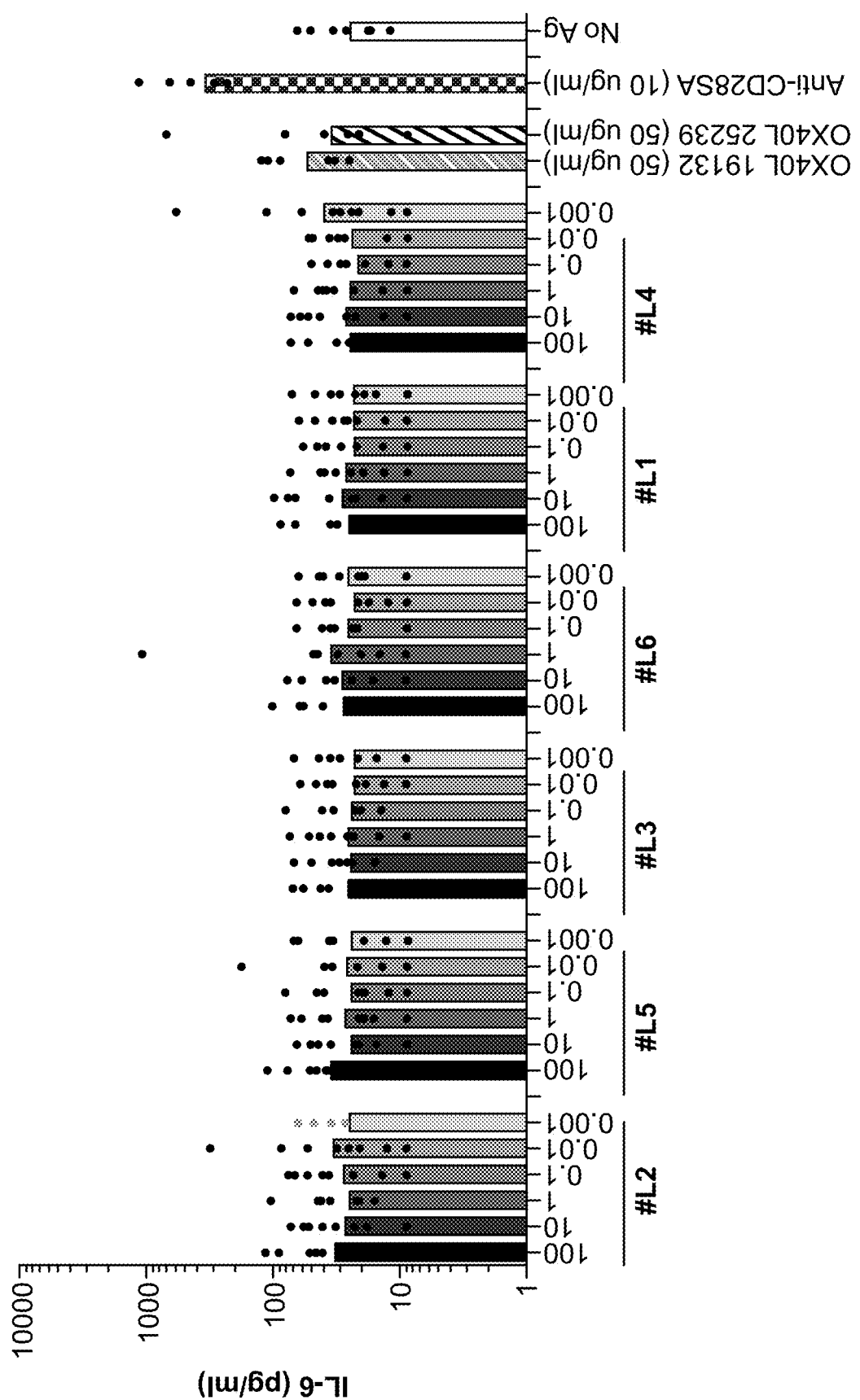
Figure 13E:
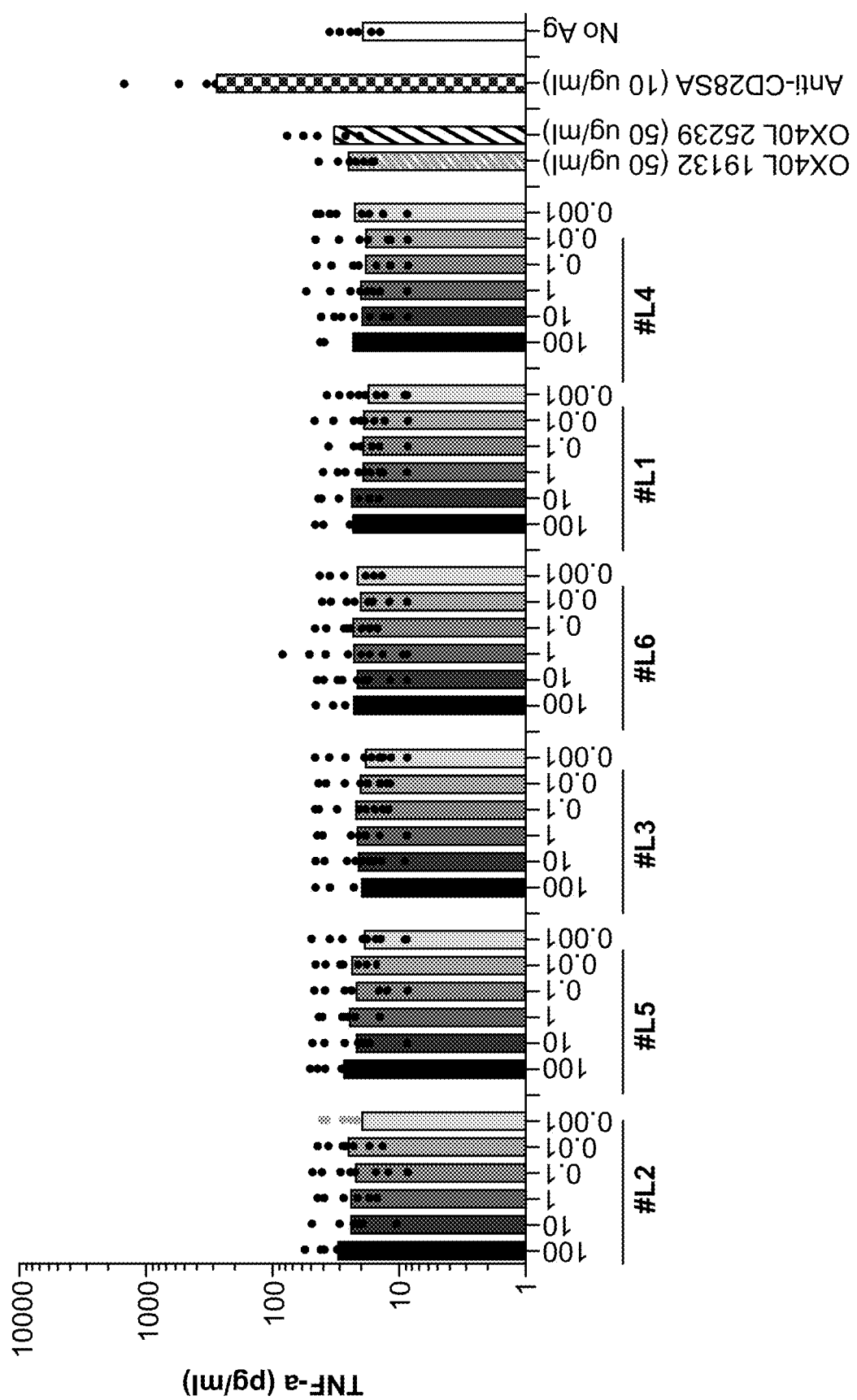
Figure 13F:
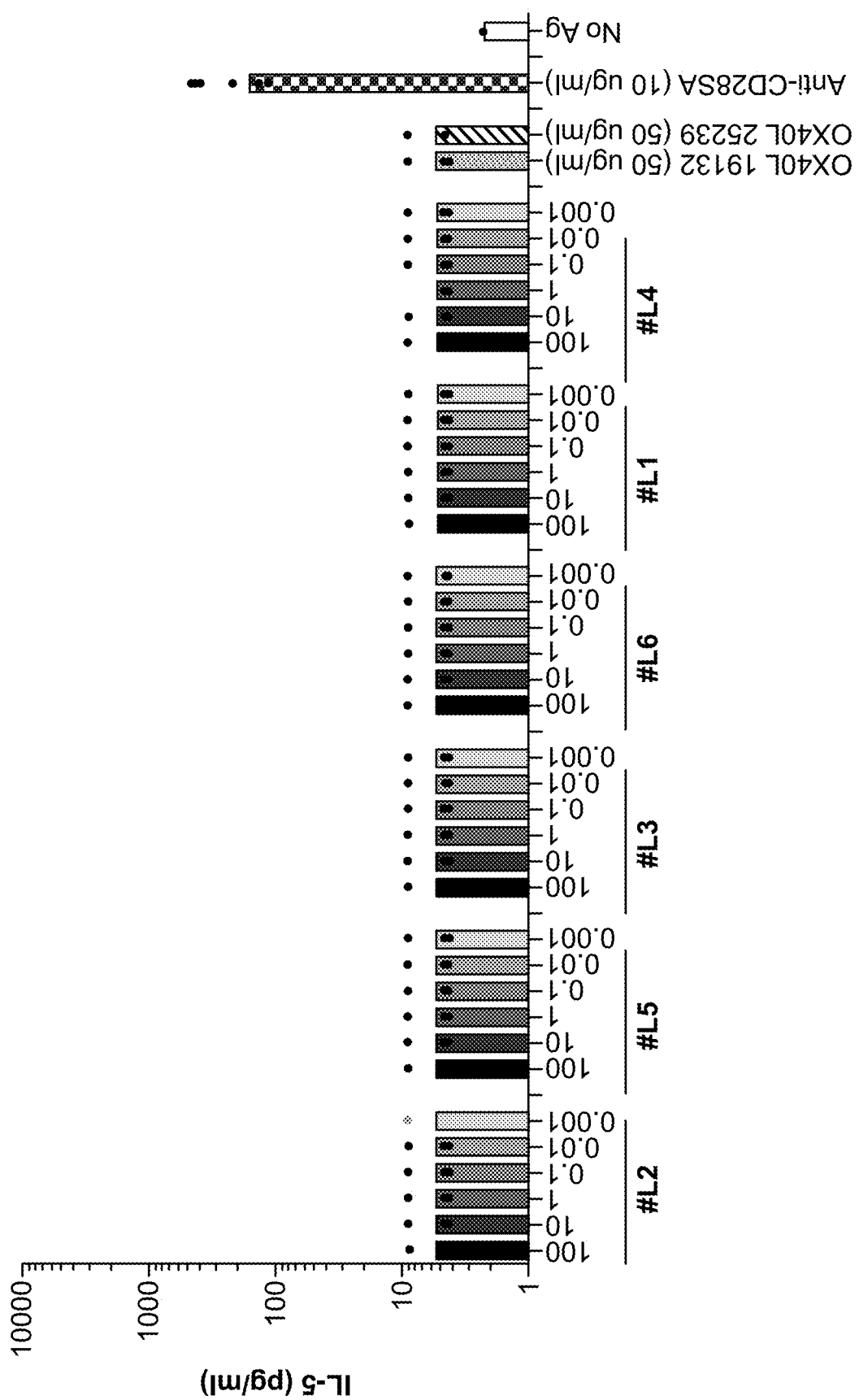
Figure 13G:
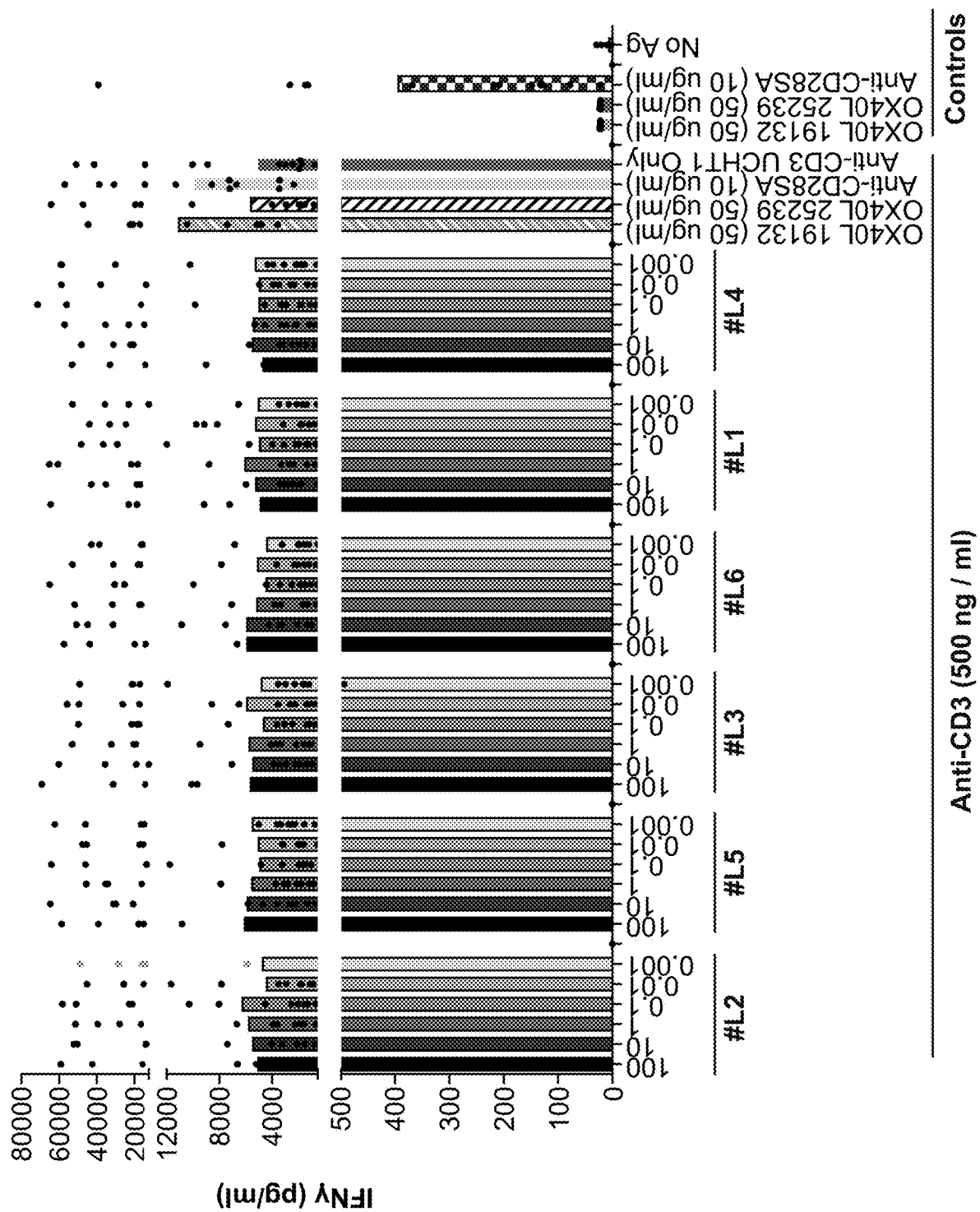
Figure 13H:
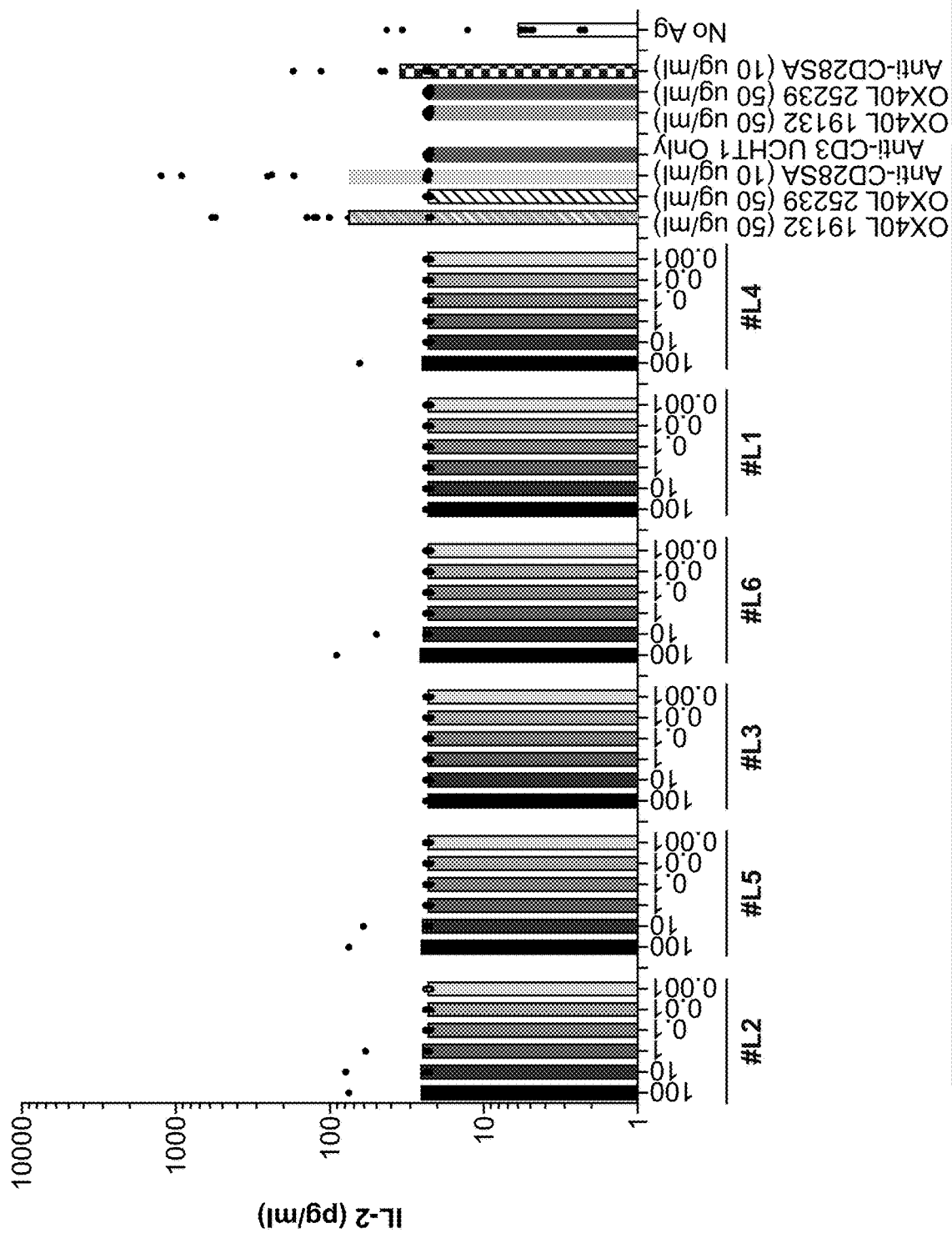
Figure 13I:
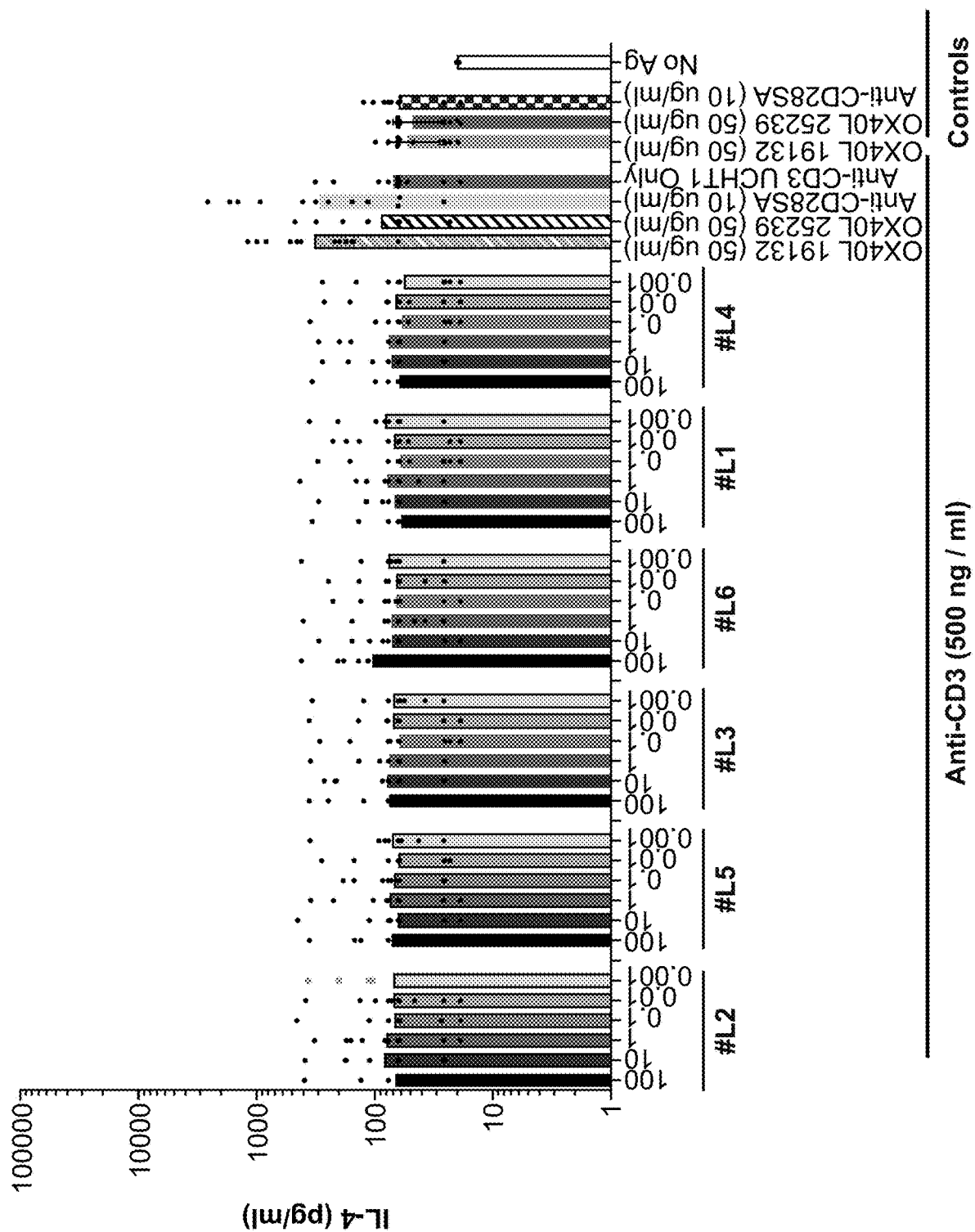
Figure 13J:
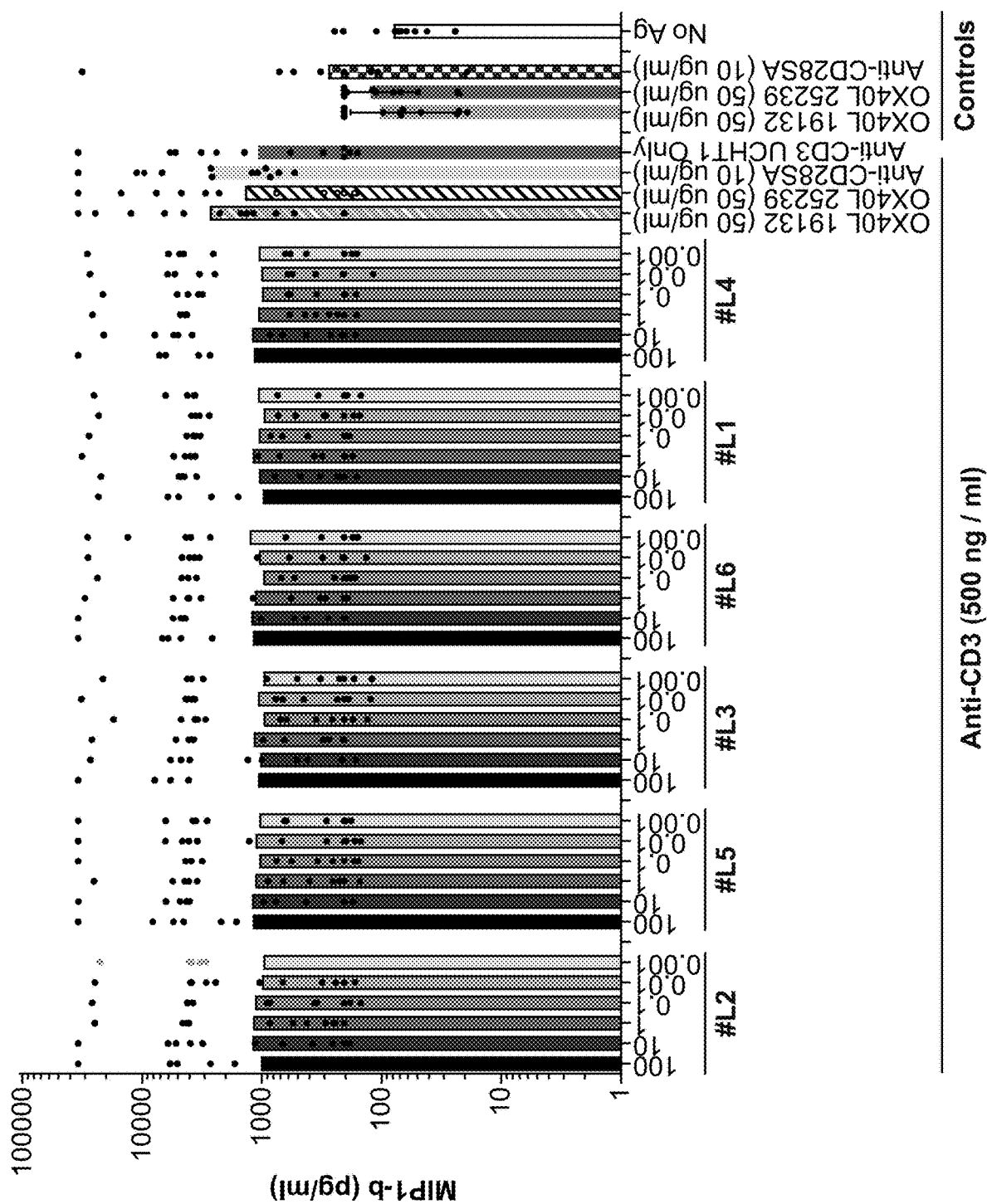
Figure 13K:
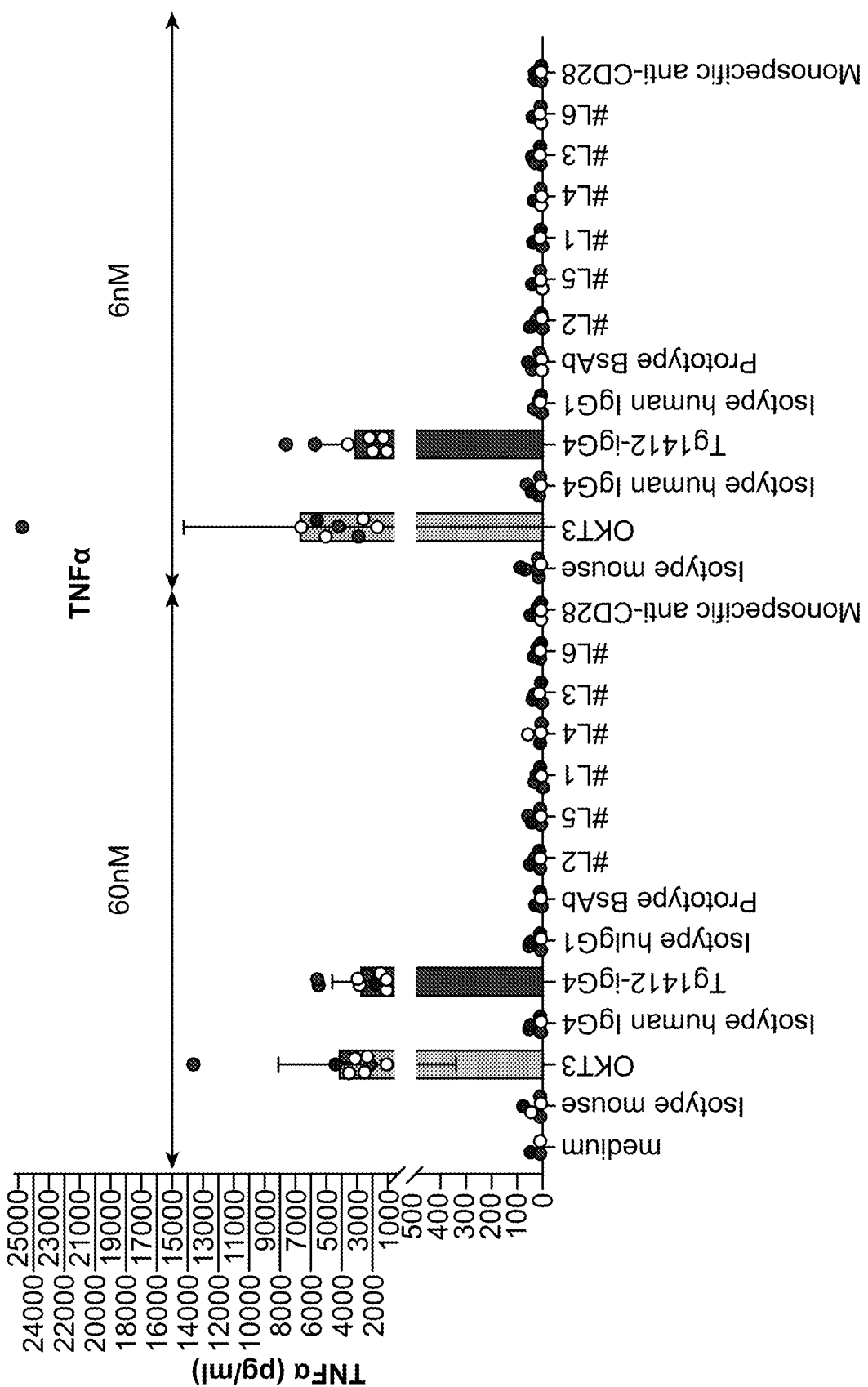
Figure 13L:
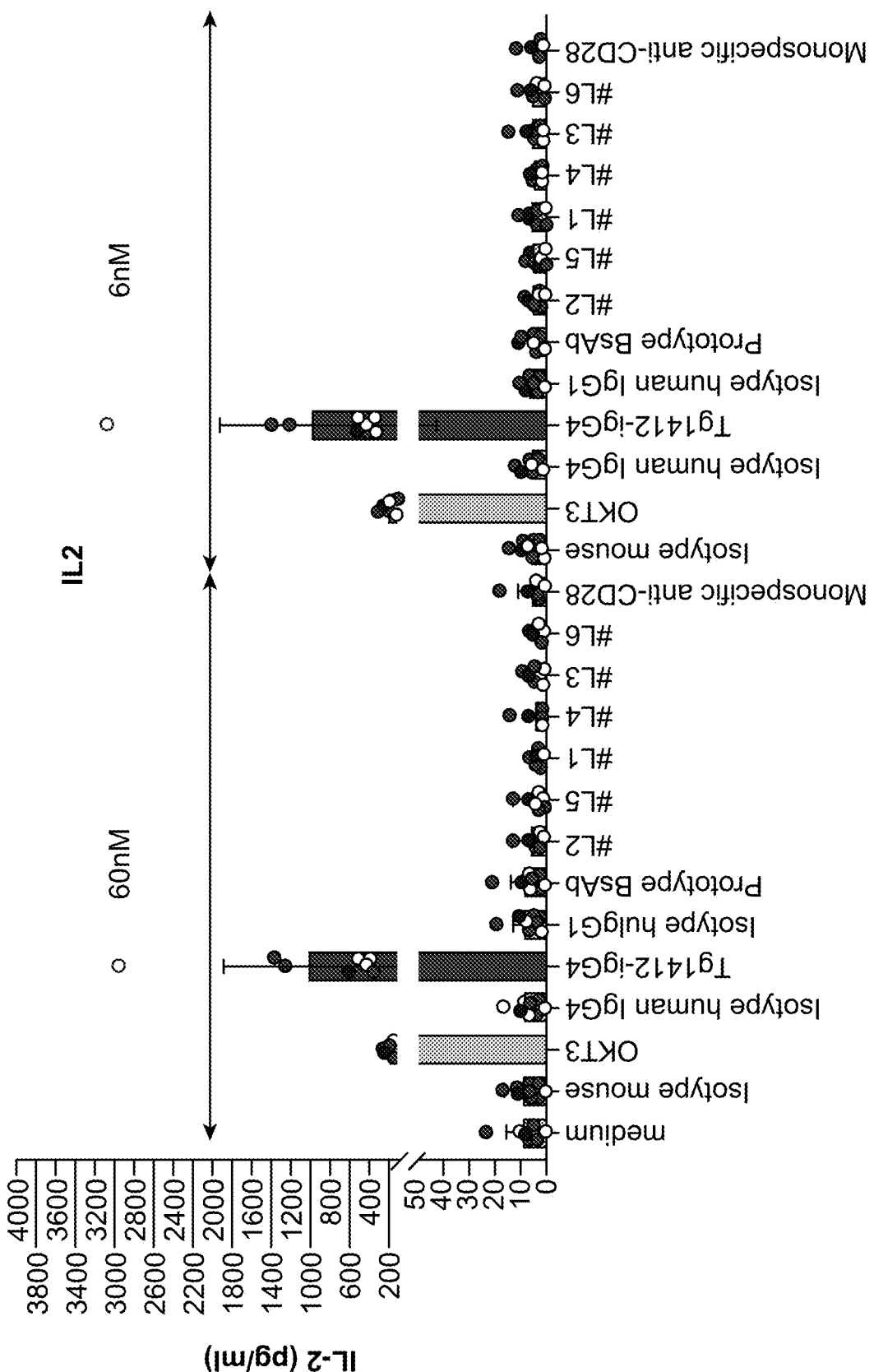
Figure 13M:
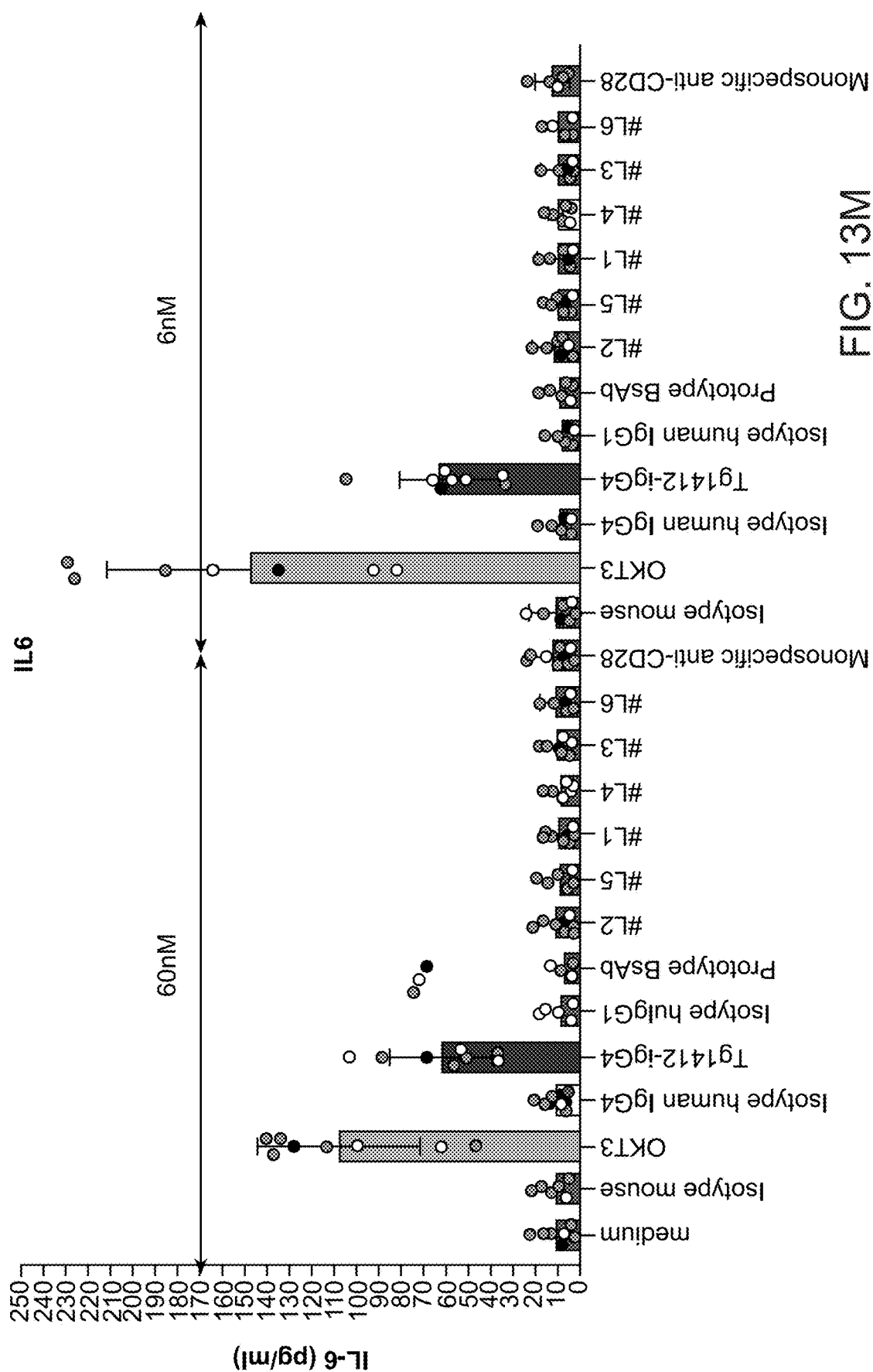
Figure 13N:
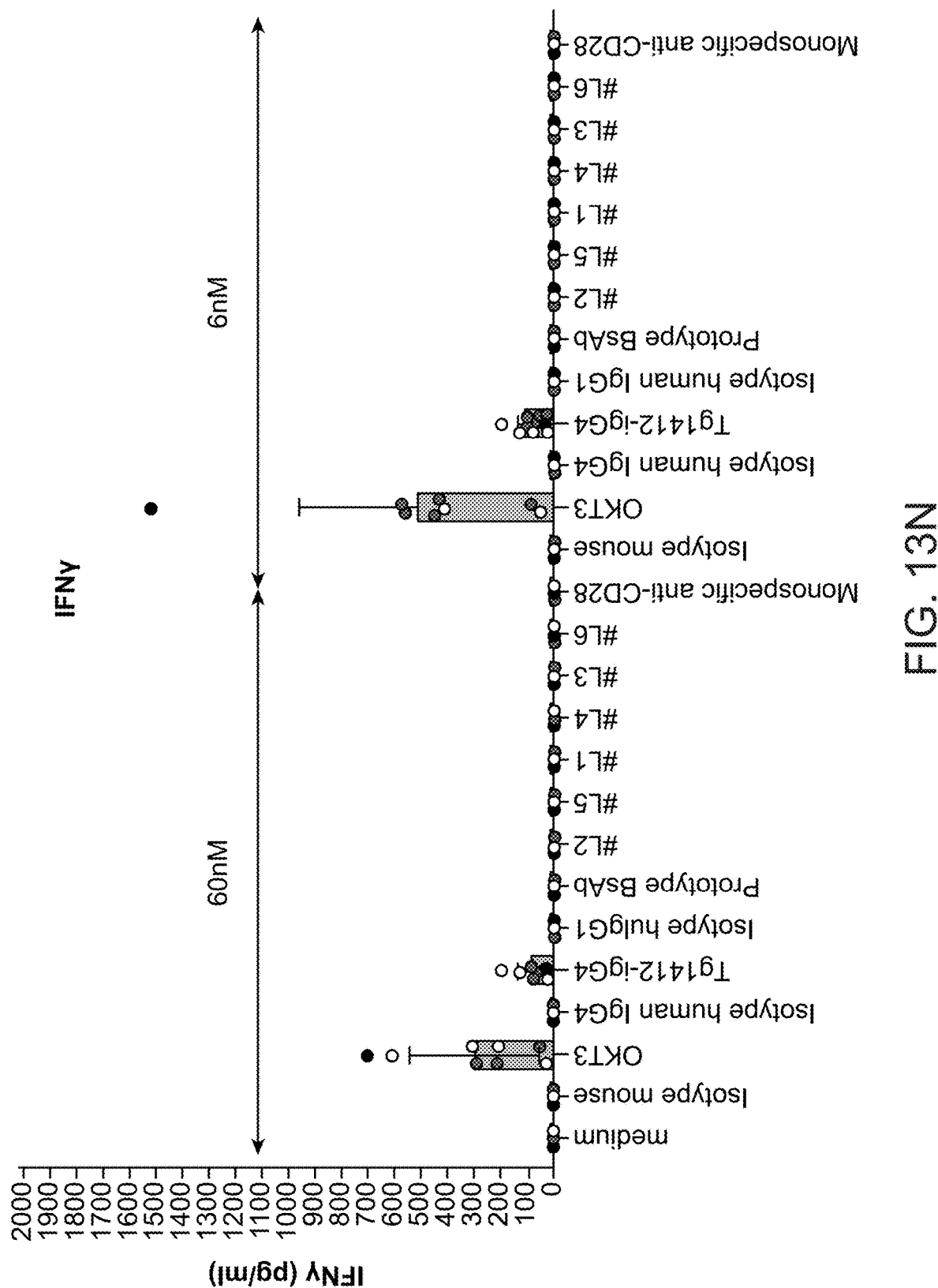

The T cell dependent antibody response (TDAR) was used to evaluate the effects of test compounds on antibody production. hCD28/hOX40 double knock-in mice were immunized with keyhole limpet hemocyanin (KLH). Fourteen days after initial immunization, mice were given a second immunization of KLH. Animals were dosed with bispecific antibodies or isotype control twice a week starting 5 days prior to initial immunization. 21 days after initial immunization, serum levels of anti-KLH IgG were measured as the primary endpoint. The bispecific antibody treated mice (e.g. L1, L3 or L4) showed significantly lower serum levels of anti-KLH IgG compared to isotype control (FIG. 12A and FIG. 12B).

GvHD was used as POM model. NSG mice were engrafted with fresh human PBMC. The bispecific antibodies were administrated IP. The bispecific prototype antibody showed in vivo activity in this model when tested at fixed concentration (0.012 mg). The effect was observed in survival, on total GVHD score, and a reduction of memory CD4+ T cell population was observed (FIG. 9A). This therapeutic effect of the bispecific was superior to the clinical benchmark Abatacept or to the anti-CD28 or anti-OX40 monotherapy, and to the combination of anti-CD28 and anti-OX40 treatments used at equimolar concentrations (FIG. 9B).

Other GvHD studies were conducted to test the protective effect of the bispecific antibody L4 when given i.p therapeutically 2×/week, at a dose of 0.12 mg and during 1 or 2 weeks only. The data from these dose duration studies (FIG. 9C to FIG. 9H) shows that treatment with L4 for either one or two weeks was sufficient to reduce GvHD progression for each of the measured endpoints and results in a more effective protection from GvHD disease than Abatacept or a bispecific clinical benchmark molecule targeting two co-stimulatory receptors.

Example 6. PK Characterization of the Bispecific Antibodies

The pharmacokinetic profile of the bispecific antibodies was characterized in hFcRn Tg32 mice. The bispecific antibodies showed slow clearance (CL) and long half life ($T_{1/2}$)—in range of expected PK parameters for a mAb/Fc asset in hFcRn Tg32 mice (FIG. 10, Table 6).

TABLE 6 hFcRn Tg32 Mouse PK Results

| | OX40 arm | CD28 arm | CL (mL/h/kg) | $V_{ss}$ (mL/kg) | $T_{1/2}$ (h/d) | $AUC_{inf}$ (h*ug/mL) |
|---|---|---|---|---|---|---|
| #L2 | L2 & L5 OX40 arm | L1 & L3 & L2 CD28 arm | 0.376 | 134 | 262/11 | 13300 |
| #L5 | L2 & L5 OX40 arm | L4 & L6 & L5 CD28 arm | 0.363 | 127 | 270/11 | 14100 |
| #L1 | L1 & L4 OX40 arm | L1 & L3 & L2 CD28 arm | 0.286 | 128 | 334/14 | 17700 |
| #L4 | L1 & L4 OX40 arm | L4 & L6 & L5 CD28 arm | 0.171 | 111 | 455/19 | 29300 |
| #L3 | L3 & L6 OX40 arm | L1 & L3 & L2 CD28 arm | 0.224 | 124 | 409/17 | 22600 |
| #L6 | L3 & L6 OX40 arm | L4 & L6 & L5 CD28 arm | 0.482 | 167 | 270/11 | 10400 |

Example 7. A Randomized, Double-Blind, Placebo-Controlled Study of the Safety, Tolerability, Pharmacokinetics and Pharmacodynamics of Ascending Single and Multiple Doses of Antigen Binding Protein L4 in Healthy, Adult Participants A phase 1 clinical trial is planned to assess the safety, tolerability, pharmacokinetics (PK), and pharmacodynamics (PD) of ascending single and multiple doses of antigen binding protein L4 in female and male healthy participants 18 to 55 years of age.

Description of Intervention:
Formulation: Powder for solution for injection and infusion supplied in a single-use glass vial. Each vial contains 100 mg of antigen binding protein L4. A precoating solution supplied with antigen binding protein L4 is used to coat infusion bags in order to prevent adsorption of antigen binding protein L4 to the bag.
Routes of administration: Intravenous (IV) infusion or Subcutaneous (SC) injection.
Dose Regimen:
Part 1:
The single ascending dose (SAD) study will include up to 9 cohorts treated with ascending doses, each cohort with single dose, including 5 cohorts of IV infusion with an expected dose range of 0.3 to 30 mg IV infusion followed by up to 4 cohorts with an expected dose range of 75 to 500 mg or less SC injection.
Part 2:
The multiple ascending dose (MAD) study will include up to 4 cohorts treated with ascending SC doses with expected doses of up to 30, 60, or 120 mg. Dosing will be SC injection Q2W with a total of 3 doses. In the optional MAD cohort (MAD4), any dose lower or higher than in MAD1 through MAD3 may be selected as long as the resulting predicted exposure is lower than the highest exposure in SAD study.

SC administration for Cohort 6 and higher in part 1, and part 2, since it will be mode of administration in later clinical development. For the safety feature, Cohort 1-5 in part 1 is planned to be administrated by IV infusion. The infusion duration is planned for approximately 60 minutes, there will be an opportunity to stop infusion if acute AEs are observed.

The doses in SAD study and MAD study may be changed based on emerging safety data and PK (Pharmacokinetics), PD (Pharmacodynamics) and ADA (Anti-Drug Antibodies) results. The same group of participants will undertake only one part. A nurse will administer the dosage.
Control Treatment:
Placebo IV:
Formulation: isotonic saline solution.
Routes of administration: Intravenous (IV) injection.
Dose regimen: same frequency and same volume for the final formulation of the IMP as for antigen binding protein L4 in the corresponding cohort and same posture requirements.
Placebo SC:
Formulation: isotonic saline solution for injection supplied in a single-use glass vial. Each vial contains 8 mL placebo.
Routes of administration: Subcutaneous (SC) injection.
Dose regimen: same frequency and same volume for the final formulation of the IMP (investigational medicinal product) as for antigen binding protein L4 in the corresponding cohort and same posture requirements and options for injection location as for antigen binding protein L4.
Outcomes:
Primary Outcome:
Number of participants with adverse events (AEs)/treatment-emergent adverse events (TEAEs), including injection site reactions: by assessment of vital signs (heart rate, systolic and diastolic blood pressure [in a seated and standing position using an automated BP monitor], body temperature [using an ear thermometer], clinical laboratory evaluations (hematology, biochemistry, coagulation, urinalysis) assessed using blood samples, and 12-lead ECG.
Timepoint
Part 1 Cohort 1-2: Baseline up to end of study (Day 85):
Vital signs assessed at Baseline, D1 (pre-dose, 0.5, 1, 4, 8 hours post-dose), D2, D3, D4, D5, D6, D8, D15, D22, D29, D36, D43, D57, and D85.

Blood samples collected at Baseline, D2, D6, D8, D15, D22, D29, D36, D43, D57, and D85.

12-lead ECG performed at Baseline, D1 (0.5, 1, 4, 8 hours post-dose), D2, D3, D4, D5, D6, D8, D15, D22, D29, D36, D43, D57, and D85.

Part 1 Cohort 3-9:
  Vital signs assessed at Baseline, D-12, D1 (pre-dose, 0.5, 1, 4, 8 hours post-dose), D2, D3, D4, D5, D6, D8, D15, D22, D29, D36, D43, D57, and D85.
  Blood samples collected at Baseline, D2, D6, D8, D15, D22, D29, D36, D43, D57, and D85
  12-lead ECG performed at Baseline, D1 (0.5, 1, 4, 8 hours post-dose), D2, D3, D4, D5, D6, D8, D15, D22, D29, D36, D43, D57, and D85.

Part 2: Baseline up to end of study (Day 113)
  Vital signs assessed at Baseline, D1 (prior to first dose, 8 hours post-first dose), D2, D3, D4, D8, D9, D15 (prior to second dose, 8 hours post-second dose), and D16, D17, D18, D22, D23, D29 (prior to third dose, 8 hours post-second dose), D30, D31, D32, D36, D43, D50, D57, D71, D85, and D113.
  Blood samples collected at Baseline and D2, D3, D4, D8, D14, D16, D17, D18, D22, D28, D30, D31, D32, D36, D43, D50, D57, D71, D85, and D113.
  12-lead ECG performed at D1 (prior to first dose, 8 hours post-dose), D2, D3, D4, D8, D15 (prior to second dose, 8 hours post-dose), D18, D29 (prior to third dose, 8 hours post-dose), D30, D31, D32, D36, D43, D50, D57, D71, D85, and D113.

Secondary Outcome 1:
Part 1: Assessment of pharmacokinetic (PK) parameters using blood samples:
IV: Cmax, Tmax, AUClast, AUC, t1/2z, CL, Vss
SC: Cmax, tmax, AUClast, AUC, F, t1/2z, CL/F, Vz/F
Part 2: Assessment of pharmacokinetic (PK) parameters using blood samples:
  D1 (AUCtau, tmax, Cmax)
  D15 (Ctrough)
  D29 (Cmax, tmax, AUCtau, Ctrough, t1/2z)

Secondary Outcome 1 Timepoint
Part 1: Baseline up to end of study (Day 85)
Cohort 1 to 5 (IV dosing):
Blood samples collected at: Baseline, D1 (0.5, 1, 4, 8 hours post-dose), D2, D3, D4, D5, D6, D8, D15, D22, D29, D36, D43, and D85.
Cohort 6 to 9 (SC dosing):
Blood samples collected at: Baseline, D1 (8 hours post-dose), D2, D3, D4, D5, D6, D8, D15, D22, D29, D36, D43, and D85.
Part 2: Baseline up to end of study (Day 113)
Blood samples collected at: D1 (prior to first dose, 8 hours post-dose), D2, D3, D4, D8, D15 before second dose, D29 (prior to third dose, 8 hours post-dose) and D30, D31, D32, D36, D43, D50, D57, D71, D85, D112.

Secondary Outcome 2:
Anti-drug antibodies against antigen binding protein L4 using blood samples.
Secondary Outcome 2 Timepoint
Part 1: Baseline up to end of study (Day 85)
Blood samples collected at: D1, D15, D29, and D85.
Part 2: Baseline up to end of study (Day 113) Blood samples collected at: D1, D15 (prior to second dose), D29 (prior to third dose) and D113.

Secondary Outcome 3:
Circulating immunoglobulin G antibodies against KLH (Keyhole limpet hemocyanin) using blood samples.

Secondary Outcome 3 Timepoint
Part 1:
Blood samples collected at: D-12 pre-KLH administration, D-5, D1 pre-dose, D3 before KLH injection, D10, D17 (before KLH ID injection), D22, D29, and D36.
Part 2:
Blood samples collected at: D1 pre-dose, D8 (before KLH injection), D15 (prior to second dose), D22 (before KLH injection), D29 (prior to third dose), D36 (before KLH injection), D43, D50, and D57.

Secondary Outcome 4:
Skin erythema measured by photography.
Secondary Outcome 4 Timepoint
Cohort 3-9 in Part 1
Conducted at: D17 (before KLH ID injection), D18, and D19.
Part 2:
Conducted at: D36 (before KLH injection), D37, and D38.

Secondary Outcome 5:
Skin blood perfusion measured by laser speckle contrast imaging (LSCI).
Secondary Outcome 5 Timepoint
Cohort 3-9 in Part 1
Conducted at: D17 (before KLH ID injection), D18, and D19.
Part 2:
Conducted at: D36 (before KLH injection), D37, and D38.

Eligibility:
Key Inclusion Criteria:
  Participants who are overtly healthy as determined by medical evaluation including medical/surgical history, physical examination, laboratory tests, and cardiac monitoring. Body weight between 50.0 and 110.0 kg, inclusive, if male, and between 40.0 and 90.0 kg, inclusive, if female, BMI between 18.0 and 32.0 kg/m2, inclusive.
  A female participant not pregnant or breastfeeding, and one of the following conditions applies:
    Is a woman of non-child-bearing potential (WONCBP) or
    Is a woman of child-bearing potential (WOCBP) and agrees to use a contraceptive method that is highly effective.
    A WOCBP must have a negative highly sensitive pregnancy test ([urine or serum] as required by local regulation) within 36 hours before the first administration of study intervention.
  Male participants who agree to:
    refrain from donating sperm;
    be abstinent from heterosexual intercourse as their preferred and usual lifestyle (abstinent on a long term and persistent basis) and agree to remain abstinent;
  OR
    Must agree to use contraception/barrier.
Age
  18 to 55 years old.
Sex:
  Male and female
Key Exclusion Criteria:
  Participants are excluded from the study if any of the following criteria apply:
    Any history or presence of clinically relevant cardiovascular, pulmonary, gastrointestinal, hepatic, renal, metabolic, hematological, neurological, osteomuscular, articular, psychiatric, systemic, ocular, gynecologic (if female), immunological or infectious disease, or signs of acute illness.
    Presence or history of drug hypersensitivity, or allergic disease diagnosed and treated by a physician.

Anaphylaxis from any cause. Known hypersensitivity to any component of the IMP formulation. Previous exposure to KLH or hypersensitivity to shellfish. History of mild, controlled allergy may be included at Investigator's discretion.

Any immunization with a non-live vaccine, including against COVID-19, within 4 weeks of enrollment (SAD study Cohort 1 and 2, MAD study) or within 2 weeks of enrollment (SAD study Cohort 3 and higher).

Any immunization with a live vaccine within 3 months of enrollment.

Symptomatic herpes zoster within 3 months prior to Screening.

History of recurrent oral or genital herpes.

Evidence of active or latent TB as documented by medical history and examination, chest X-rays or a positive QuantiFERON-TB Gold Plus test.

History of invasive opportunistic infections such as histoplasmosis, listeriosis, coccidioidomycosis, candidiasis, *pneumocystis jirovecii*, aspergillosis, irrespective of resolution.

| Dosing Scheme: | | | |
|---|---|---|---|
| SAD | | | |
| Cohort | Dose (mg) | Route | |
| 1 | 0.3 | IV infusion | |
| 2 | 1 | IV infusion | |
| 3 | 3 | IV infusion | |
| 4 | 10 | IV infusion | |
| 5 | 30 | IV infusion | |
| 6 | 75 | SC injection | |
| 7 | 150 | SC injection | |
| 8 | 300 | SC injection | |
| 9 (optional) | 500 | SC injection | |
| MAD | | | |
| Cohort | Dose (mg) | Route | Regimen |
| 1 | 30 | SC injection | Q2W |
| 2 | 60 | SC injection | Q2W |
| 3 | 120 | SC injection | Q2W |
| 4 (optional) | 240 | SC injection | Q2W |

| SEQUENCE LISTING | |
|---|---|
| SEQ ID | SEQUENCE |
| L4 & L6 & L5 CD28 HCDR1 SEQ ID NO: 1 | GFTFSSYY |
| L4 & L6 & L5 CD28 HCDR2 SEQ ID NO: 2 | INTDGDFT |
| L4 & L6 & L5 CD28 HCDR3 SEQ ID NO: 3 | ARARGPYSRGSQGHDY |
| L4 & L1 OX40 HCDR1 SEQ ID NO: 4 | GFTFSSYA |
| L4 & L1 OX40 HCDR2 SEQ ID NO: 5 | ISSQGGST |
| L4 & L1 OX40 HCDR3 SEQ ID NO: 6 | ARGEAYWYRWAFDY |
| L4 & L1 OX40 LCDR1 SEQ ID NO: 7 | QSISSW |
| L4 & L1 OX40 LCDR2 SEQ ID NO: 8 | DAS |
| L4 & L1 OX40 LCDR3 SEQ ID NO: 9 | QQYSDYSYT |
| L4, L6 & L5 CD28 VHH SEQ ID NO: 10 | DVQLVESGGGVVQPGGSLRLSCAASGFTFSSYYMSWVRQAPGKGLE WVSTINTDGDFTSYADSVKGRFTISRDNAKNTLYLQMNSLRPEDTALY YCARARGPYSRGSQGHDYRGQGTLVTVSS |
| L4 & L1 OX40 VH SEQ ID NO: 11 | EVQLVESGGGLVQPGGSLRLSCAASGFTFSSYAMHWVRQAPGKGLE YVSAISSQGGSTYYANSVKGRFTISRDNSKNTLYLQMGSLRAEDTAVY YCARGEAYWYRWAFDYWGQGTLVTVSS |
| L4 & L1 OX40 VL SEQ ID NO: 12 | DIQMTQSPSTLSASVGDRVTITCRASQSISSWLAWYQQKPGKAPKLLI YDASSLESGVPSRFSGSGSGTEFTLTISSLQPDDFATYYCQQYSDYSY TFGQGTKVEIK |

| SEQ ID | SEQUENCE |
|---|---|
| L1 & L3 & L2 CD28 HCDR1 SEQ ID NO: 13 | GSFFSIDT |
| L1 & L3 & L2 CD28 HCDR2 SEQ ID NO: 14 | VTSGGLT |
| L1 & L3 & L2 CD28 HCDR3 SEQ ID NO: 15 | SARIRTSGGGGWSTY |
| L1 & L3 & L2 CD28 VHH SEQ ID NO: 16 | DVQLVESGGGVVQPGGSLRLSCAASGSFFSIDTMDWYRQAPGKQRE LVTGVTSGGLTNYADSVKGRFTISIDNAKNTVYLQMNSLRPEDTALYY CSARIRTSGGGGWSTYWGQGTLVTVSS |
| L6 & L3 OX40 HCDR1 SEQ ID NO: 17 | GYTFTSYG |
| L6 & L3 OX40 HCDR2 SEQ ID NO: 18 | ISAYTGNT |
| L6 & L3 OX40 HCDR3 SEQ ID NO: 19 | ARDGYPIDY |
| L6 & L3 OX40 LCDR1 SEQ ID NO: 20 | QSISSW |
| L6 & L3 OX40 LCDR2 SEQ ID NO: 21 | DAS |
| L6 & L3 OX40 LCDR3 SEQ ID NO: 22 | QQYTSYSDT |
| L6 & L3 OX40 VH SEQ ID NO: 23 | QVQLVQSGAEVKKPGASVKVSCKASGYTFTSYGISWVRQAPGQGLE WMGWISAYTGNTNYAQKLQGRVTMTTDTSTSTAYMELRSLRSDDTA VYYCARDGYPIDYWGQGTLVTVSS |
| L6 & L3 OX40 VL SEQ ID NO: 24 | DIQMTQSPSTLSASVGDRVTITCRASQSISSWLAWYQQKPGKAPKLLI YDASSLESGVPSRFSGSGSGTEFTLTISSLQPDDFATYYCQQYTSYSD TFGQGTKVEIK |
| L5 & L2 OX40 HCDR1 SEQ ID NO: 25 | GFTFSSYA |
| L5 & L2 OX40 HCDR2 SEQ ID NO: 26 | ISSQGGST |
| L5 & L2 OX40 HCDR3 SEQ ID NO: 27 | ARGGSGWYNSEFDY |
| L5 & L2 OX40 LCDR1 SEQ ID NO: 28 | QSISSW |
| L5 & L2 OX40 LCDR2 SEQ ID NO: 29 | DAS |
| L5 & L2 OX40 LCDR3 SEQ ID NO: 30 | QQYNDYSYT |
| L5 & L2 OX40 VH SEQ ID NO: 31 | EVQLVESGGGLVQPGGSLRLSCAASGFTFSSYAMHWVRQAPGKGLE YVSAISSQGGSTYYANSVKGRFTISRDNSKNTLYLQMGSLRAEDTAVY YCARGGSGWYNSEFDYWGQGTLVTVSS |

| SEQ ID | SEQUENCE |
| --- | --- |
| L5 & L2<br>OX40 VL<br>SEQ ID NO: 32 | DIQMTQSPSTLSASVGDRVTITCRASQSISSWLAWYQQKPGKAPKLLI<br>YDASSLESGVPSRFSGSGSGTEFTLTISSLQPDDFATYYCQQYNDYSY<br>TFGQGTKVEIK |
| L4 & L1<br>Polypeptide Chain<br>(I)<br>light chain<br>SEQ ID NO: 33 | DIQMTQSPSTLSASVGDRVTITCRASQSISSWLAWYQQKPGKAPKLLI<br>YDASSLESGVPSRFSGSGSGTEFTLTISSLQPDDFATYYCQQYSDYSY<br>TFGQGTKVEIKRTVAAPSVFIFPPSDEQLKSGTASVVCLLNNFYPREAK<br>VQWKVDNALQSGNSQESVTEQDSKDSTYSLSSTLTLSKADYEKHKVY<br>ACEVTHQGLSSPVTKSFNRGEC |
| L6 & L3<br>Polypeptide Chain<br>(I)<br>light chain<br>SEQ ID NO: 34 | DIQMTQSPSTLSASVGDRVTITCRASQSISSWLAWYQQKPGKAPKLLI<br>YDASSLESGVPSRFSGSGSGTEFTLTISSLQPDDFATYYCQQYTSYSD<br>TFGQGTKVEIKRTVAAPSVFIFPPSDEQLKSGTASVVCLLNNFYPREAK<br>VQWKVDNALQSGNSQESVTEQDSKDSTYSLSSTLTLSKADYEKHKVY<br>ACEVTHQGLSSPVTKSFNRGEC |
| L5 & L2<br>Polypeptide Chain<br>(I)<br>light chain<br>SEQ ID NO: 35 | DIQMTQSPSTLSASVGDRVTITCRASQSISSWLAWYQQKPGKAPKLLI<br>YDASSLESGVPSRFSGSGSGTEFTLTISSLQPDDFATYYCQQYNDYSY<br>TFGQGTKVEIKRTVAAPSVFIFPPSDEQLKSGTASVVCLLNNFYPREAK<br>VQWKVDNALQSGNSQESVTEQDSKDSTYSLSSTLTLSKADYEKHKVY<br>ACEVTHQGLSSPVTKSFNRGEC |
| L4<br>Polypeptide Chain<br>(II)<br>Heavy chain<br>SEQ ID NO: 36 | EVQLVESGGGLVQPGGSLRLSCAASGFTFSSYAMHWVRQAPGKGLE<br>YVSAISSQGGSTYYANSVKGRFTISRDNSKNTLYLQMGSLRAEDTAVY<br>YCARGEAYWYRWAFDYWGQGTLVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSN<br>KALPAPIEKTISKAKGQPREPQVYTLPPCRDELTKNQVSLWCLVKGFY<br>PSDIAVEWESNGQPENNYKTTPPVLDSDGSFFLYSKLTVDKSRWQQG<br>NVFSCSVMHEALHNHYTQKSLSLSPG |
| L1<br>Polypeptide Chain<br>(II)<br>Heavy chain<br>SEQ ID NO: 37 | EVQLVESGGGLVQPGGSLRLSCAASGFTFSSYAMHWVRQAPGKGLE<br>YVSAISSQGGSTYYANSVKGRFTISRDNSKNTLYLQMGSLRAEDTAVY<br>YCARGEAYWYRWAFDYWGQGTLVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPA<br>PEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSN<br>KALPAPIEKTISKAKGQPREPQVYTLPPCRDELTKNQVSLWCLVKGFY<br>PSDIAVEWESNGQPENNYKTTPPVLDSDGSFFLYSKLTVDKSRWQQG<br>NVFSCSVMHEALHNHYTQKSLSLSPG |
| L6<br>Polypeptide Chain<br>(II)<br>Heavy chain<br>SEQ ID NO: 38 | QVQLVQSGAEVKKPGASVKVSCKASGYTFTSYGISWVRQAPGQGLE<br>WMGWISAYTGNTNYAQKLQGRVTMTTDTSTSTAYMELRSLRSDDTA<br>VYYCARDGYPIDYWGQGTLVTVSSASTKGPSVFPLAPSSKSTSGGTA<br>ALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPEAA<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPCRDELTKNQVSLWCLVKGFYPSDIA<br>VEWESNGQPENNYKTTPPVLDSDGSFFLYSKLTVDKSRWQQGNVFS<br>CSVMHEALHNHYTQKSLSLSPG |
| L3<br>Polypeptide Chain<br>(II)<br>Heavy chain<br>SEQ ID NO: 39 | QVQLVQSGAEVKKPGASVKVSCKASGYTFTSYGISWVRQAPGQGLE<br>WMGWISAYTGNTNYAQKLQGRVTMTTDTSTSTAYMELRSLRSDDTA<br>VYYCARDGYPIDYWGQGTLVTVSSASTKGPSVFPLAPSSKSTSGGTA<br>ALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPEAA<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPCRDELTKNQVSLWCLVKGFYPSDIA<br>VEWESNGQPENNYKTTPPVLDSDGSFFLYSKLTVDKSRWQQGNVFS<br>CSVMHEALHNHYTQKSLSLSPG |

| SEQ ID | SEQUENCE |
|---|---|
| L5 & L2 Polypeptide Chain (II) Heavy chain SEQ ID NO: 40 | EVQLVESGGGLVQPGGSLRLSCAASGFTFSSYAMHWVRQAPGKGLE YVSAISSQGGSTYYANSVKGRFTISRDNSKNTLYLQMGSLRAEDTAVY YCARGGSGWYNSEFDYWGQGTLVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKVEPKSCDKTHTCPPCPA PEAAGGPSVFLFPPKPKDTLMISRTPEVTCVVVDVSHEDPEVKFNWYV DGVEVHNAKTKPREEQYNSTYRVVSVLTVLHQDWLNGKEYKCKVSN KALPAPIEKTISKAKGQPREPQVYTLPPCRDELTKNQVSLWCLVKGFY PSDIAVEWESNGQPENNYKTTPPVLDSDGSFFLYSKLTVDKSRWQQG NVFSCSVMHEALHNHYTQKSLSLSPG |
| L4, L6, & L5 Polypeptide Chain (III) Heavy chain SEQ ID NO: 41 | DVQLVESGGGVVQPGGSLRLSCAASGFTFSSYYMSWVRQAPGKGLE WVSTINTDGDFTSYADSVKGRFTISRDNAKNTLYLQMNSLRPEDTALY YCARARGPYSRGSQGHDYRGQGTLVTVSSGGGGSDKTHTCPPCPA PEAAGGPSVFLFPPKPKDTLMISRTPEVTCVVVDVSHEDPEVKFNWYV DGVEVHNAKTKPREEQYNSTYRVVSVLTVLHQDWLNGKEYKCKVSN KALPAPIEKTISKAKGQPREPQVCTLPPSRDELTKNQVSLSCAVKGFYP SDIAVEWESNGQPENNYKTTPPVLDSDGSFFLVSKLTVDKSRWQQGN VFSCSVMHEALHNRFTQKSLSLSPG |
| L1, L3, & L2 Polypeptide Chain (III) Heavy chain SEQ ID NO: 42 | DVQLVESGGGVVQPGGSLRLSCAASGSFFSIDTMDWYRQAPGKQRE LVTGVTSGGLTNYADSVKGRFTISIDNAKNTVYLQMNSLRPEDTALYY CSARIRTSGGGGWSTYWGQGTLVTVSSGGGGSDKTHTCPPCPAPEA AGGPSVFLFPPKPKDTLMISRTPEVTCVVVDVSHEDPEVKFNWYVDG VEVHNAKTKPREEQYNSTYRVVSVLTVLHQDWLNGKEYKCKVSNKAL PAPIEKTISKAKGQPREPQVCTLPPSRDELTKNQVSLSCAVKGFYPSDI AVEWESNGQPENNYKTTPPVLDSDGSFFLVSKLTVDKSRWQQGNVF SCSVMHEALHNRFTQKSLSLSPG |
| Bispecific CD28-OX40 Prototype: anti-OX40-huIgG1-LALA_knob_x_anti-CD28-VHH-huIgG1-LALA_hole-RF Polypeptide Chain (I) SEQ ID NO: 43 | QSVLTQPPSVSAAPGQKVTISCSGSSSNIGNNYVSWYQQLPGTAPKLL IYDNNKRPSGIPDRFSGSKSGTSATLGITGLQTGDEADYYCGTWDSSL TAYVFGGGTKLTVLGQPKAAPSVTLFPPSSEELQANKATLVCLISDFYP GAVTVAWKADSSPVKAGVETTTPSKQSNNKYAASSYLSLTPEQWKSH RSYSCQVTHEGSTVEKTVAPTECS |
| Bispecific CD28-OX40 Prototype: anti-OX40-huIgG1-LALA_knob_x_anti-CD28-VHH-huIgG1-LALA_hole-RF Polypeptide Chain (II) SEQ ID NO: 44 | EVQLVESGGVVVQPGGSLRLSCAASGFTFDDYTMHWVRQAPGKGLE WVSLISWDGGSTYYADSVKGRFTISRDNSKNSLYLQMNSLRTEDTAV YYCARDNLWGYLTYFDYWGQGTLVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKVEPKSCDKTHTCPPCPA PEAAGGPSVFLFPPKPKDTLMISRTPEVTCVVVDVSHEDPEVKFNWYV DGVEVHNAKTKPREEQYNSTYRVVSVLTVLHQDWLNGKEYKCKVSN KALPAPIEKTISKAKGQPREPQVYTLPPCRDELTKNQVSLWCLVKGFY PSDIAVEWESNGQPENNYKTTPPVLDSDGSFFLYSKLTVDKSRWQQG NVFSCSVMHEALHNHYTQKSLSLSPG |
| Bispecific CD28-OX40 Prototype: anti-OX40-huIgG1-LALA_knob_x_anti-CD28-VHH-huIgG1-LALA_hole-RF Polypeptide Chain (III) SEQ ID NO: 45 | QVQLQESGGGLVQPGGSLRLSCVASGSISSIDHVGWYRQAPGKERV MVAFINSGGRTTYPDAVKGRFTISRDGASNTVFLQMDGLKPDDTAVYY CNVLLRDRSGSGRTYWGQGTQVTVSSGGGGSDKTHTCPPCPAPEAA GGPSVFLFPPKPKDTLMISRTPEVTCVVVDVSHEDPEVKFNWYVDGV EVHNAKTKPREEQYNSTYRVVSVLTVLHQDWLNGKEYKCKVSNKALP APIEKTISKAKGQPREPQVCTLPPSRDELTKNQVSLSCAVKGFYPSDIA VEWESNGQPENNYKTTPPVLDSDGSFFLVSKLTVDKSRWQQGNVFS CSVMHEALHNRFTQKSLSLSPG |
| Human CD28 Amino acids 19-136 SEQ ID NO: 46 | NKILVKQSPMLVAYDNAVNLSCKYSYNLFSREFRASLHKGLDSAVEVC VVYGNYSQQLQVYSKTGFNCDGKLGNESVTFYLQNLYVNQTDIYFCKI EVMYPPPYLDNEKSNGTIIHVK |
| Human OX40 Amino acids 32-109 SEQ ID NO: 47 | VGDTYPSNDRCCHECRPGNGMVSRCSRSQNTVCRPCGPGFYNDVV SSKPCKPCTWCNLRSGSERKQLCTATQDTVCRC |

The invention claimed is:

1. A multispecific binding protein comprising:
(a) a first antigen binding domain (ABD) with binding specificity to CD28 comprising: an immunoglobulin single variable domain (ISVD) comprising an HCDR1 sequence comprising the amino acid sequence of GFTFSSYY (SEQ ID NO: 1), an HCDR2 sequence comprising the amino acid sequence of INTDGDFT (SEQ ID NO: 2), and an HCDR3 sequence comprising the amino acid sequence of ARARGPYSRGSQGHDY (SEQ ID NO: 3); and
(b) a second ABD with binding affinity to OX40 comprising:
(b1) an immunoglobulin heavy chain variable domain (VH) comprising an HCDR1 sequence comprising the amino acid sequence of GFTFSSYA (SEQ ID NO: 4), an HCDR2 sequence comprising the amino acid sequence of ISSQGGST (SEQ ID NO: 5), and an HCDR3 sequence comprising the amino acid sequence of ARGEAYWYRWAFDY (SEQID NO: 6); and
(b2) an immunoglobulin light chain variable domain (VL) comprising an LCDR1 sequence comprising the amino acid sequence QSISSW (SEQ ID NO: 7), an LCDR2 sequence comprising the amino acid sequence of DAS, and an LCDR3 sequence comprising the amino acid sequence of QQYSDYSYT (SEQ ID NO: 9).

2. The multispecific binding protein of claim 1, wherein: the ISVD comprises an amino acid sequence that is at least about 80% identical to the amino acid sequence of SEQ ID NO: 10 and comprises amino acid Y33, W47, T50, N52, D56, F57, T58, S59, K65, P102, Y103, S104, and R105 relative to SEQ ID NO: 10; and/or the VH comprises an amino acid sequence that is at least about 80% identical to the amino acid sequence of SEQ ID NO: 11 and comprises amino acids H35, S52, Q54, G56, S57, T58, Y59, Y102, Y104, R105, and W106 relative to SEQ ID NO: 11, and the VL comprises an amino acid sequence that is at least about 80% identical to the amino acid sequence of SEQ ID NO: 12 and comprises amino acids W32, D50, and S92 relative to SEQ ID NO: 12.

3. The multispecific binding protein of claim 1, wherein: the ISVD comprises the amino acid sequence of SEQ ID NO: 10; and the VH comprises the amino acid sequence of SEQ ID NO: 11 and the VL comprises the amino acid sequence of SEQ ID NO: 12.

4. The multispecific binding protein of claim 1, wherein the binding protein comprises: (i) a first polypeptide chain comprising the amino acid sequence of SEQ ID NO: 33; (ii) a second polypeptide chain comprising the amino acid sequence of SEQ ID NO: 36; and (iii) a third polypeptide chain comprising the amino acid sequence of SEQ ID NO: 41.

5. The multispecific binding protein of claim 1, wherein the ISVD is a VHH, a humanized VHH or a camelized VH, or an antigen binding fragment thereof.

6. The multispecific binding protein of claim 1, further comprising an immunoglobulin Fc domain or variant thereof, wherein the Fc domain or variant thereof comprises a first Fc heavy chain and a second Fc heavy chain.

7. The multispecific binding protein of claim 6, wherein the first ABD is linked to the first Fc heavy chain and the second ABD is linked to the second Fc heavy chain.

8. The multispecific binding protein of claim 6, wherein the first ABD is linked to the N-terminus of the second ABD VH.

9. The multispecific binding protein of claim 6, wherein the first ABD is linked to the C-terminus of the second Fc heavy chain and the second ABD is linked to the N-terminus of the second Fc heavy chain.

10. The multispecific binding protein of claim 6, wherein the VH is linked to a CH1 domain and the VL is linked to a constant light (CL) domain and the first ABD is linked to the C-terminus of the CL domain.

11. The multispecific binding protein of claim 6, wherein the first Fc heavy chain comprises a Y349C substitution and the second Fc heavy chain comprises a S354C substitution, according to EU numbering.

12. The multispecific binding protein of claim 6, wherein the first Fc heavy chain comprises a Y349C, T366S, L368A, or Y407V substitutions and the second Fc heavy chain comprises a T366W substitution, according to EU numbering.

13. The multispecific binding protein of claim 6, wherein at least one Fc heavy chain comprises H435R and Y436F substitutions, according to EU numbering.

14. The multispecific binding protein of claim 6, at least one Fc heavy chain comprises L234A and L235A substitutions, according to EU numbering.

15. A pharmaceutical composition comprising the binding protein of claim 1 and a pharmaceutically acceptable carrier.

16. An isolated nucleic acid molecule encoding the binding protein of claim 1.

17. A binding protein comprising an immunoglobulin single variable domain (ISVD) with binding specificity to CD28, comprising:
an HCDR1 sequence comprising the amino acid sequence of GFTFSSYY (SEQ ID NO: 1),
an HCDR2 sequence comprising the amino acid sequence of INTDGDFT (SEQ ID NO: 2), and
an HCDR3 sequence comprising the amino acid sequence of ARARGPYSRGSQGHDY (SEQ ID NO: 3).

18. The binding protein of claim 1, wherein
the ISVD comprises an amino acid sequence that is at least about 80% identical to the amino acid sequence of SEQ ID NO: 10 and comprises amino acid Y33, W47, T50, N52, D56, F57, T58, S59, K65, P102, Y103, S104, and R105 relative to SEQ ID NO: 10.

19. The binding protein of claim 17, wherein the ISVD comprises an amino acid sequence of SEQ ID NO: 10.

20. A pharmaceutical composition comprising the binding protein of claim 17 and a pharmaceutically acceptable carrier.

21. An isolated nucleic acid molecule encoding the binding protein of claim 17.

22. A binding protein with binding specificity to OX40 comprising an immunoglobulin heavy chain variable domain (VH) and an immunoglobulin light chain variable domain (VL), wherein the binding protein comprises: an HCDR1 sequence comprising the amino acid sequence of GFTFSSYA (SEQ ID NO: 4), an HCDR2 sequence comprising the amino acid sequence of ISSQGGST (SEQ ID NO: 5), and an HCDR3 sequence comprising the amino acid sequence of ARGEAYWYRWAFDY (SEQID NO: 6); and an LCDR1 sequence comprising the amino acid sequence QSISSW (SEQ ID NO: 7), an LCDR2 sequence comprising the amino acid sequence of DAS, and an LCDR3 sequence comprising the amino acid sequence of QQYSDYSYT (SEQ ID NO: 9).

23. The binding protein of claim 22, wherein
the VH comprises an amino acid sequence that is at least about 80% identical to the amino acid sequence of SEQ ID NO: 11 and comprises amino acids H35, S52, Q54, G56, S57, T58, Y59, Y102, Y104, R105, and W106 relative to SEQ ID NO: 11, and the VL comprises an amino acid sequence that is at least about 80% identical to the amino acid sequence of SEQ ID NO: 12 and comprises amino acids W32, D50, and S92 relative to SEQ ID NO: 12.

24. The binding protein of claim 22, wherein the VH comprises the amino acid sequence of SEQ ID NO: 11 and the VL comprises the amino acid sequence of SEQ ID NO: 12.

25. A pharmaceutical composition comprising the binding protein of claim 22 and a pharmaceutically acceptable carrier.

26. An isolated nucleic acid molecule encoding the binding protein of claim 22.

* * * * *

SEQUENCE LISTING

```
Sequence total quantity: 104
SEQ ID NO: 1                moltype = AA  length = 8
FEATURE                     Location/Qualifiers
source                      1..8
                            mol_type = protein
                            organism = synthetic construct
SEQUENCE: 1
GFTFSSYY                                                                  8

SEQ ID NO: 2                moltype = AA  length = 8
FEATURE                     Location/Qualifiers
source                      1..8
                            mol_type = protein
                            organism = synthetic construct
SEQUENCE: 2
INTDGDFT                                                                  8

SEQ ID NO: 3                moltype = AA  length = 16
FEATURE                     Location/Qualifiers
source                      1..16
                            mol_type = protein
                            organism = synthetic construct
SEQUENCE: 3
ARARGPYSRG SQGHDY                                                        16

SEQ ID NO: 4                moltype = AA  length = 8
FEATURE                     Location/Qualifiers
source                      1..8
                            mol_type = protein
                            organism = synthetic construct
SEQUENCE: 4
GFTFSSYA                                                                  8

SEQ ID NO: 5                moltype = AA  length = 8
FEATURE                     Location/Qualifiers
source                      1..8
                            mol_type = protein
                            organism = synthetic construct
SEQUENCE: 5
ISSQGGST                                                                  8

SEQ ID NO: 6                moltype = AA  length = 14
FEATURE                     Location/Qualifiers
source                      1..14
                            mol_type = protein
                            organism = synthetic construct
SEQUENCE: 6
ARGEAYWYRW AFDY                                                          14

SEQ ID NO: 7                moltype = AA  length = 6
FEATURE                     Location/Qualifiers
source                      1..6
                            mol_type = protein
                            organism = synthetic construct
SEQUENCE: 7
QSISSW                                                                    6

SEQ ID NO: 8                moltype =     length =
SEQUENCE: 8
000

SEQ ID NO: 9                moltype = AA  length = 9
FEATURE                     Location/Qualifiers
source                      1..9
                            mol_type = protein
                            organism = synthetic construct
SEQUENCE: 9
QQYSDYSYT                                                                 9

SEQ ID NO: 10               moltype = AA  length = 123
FEATURE                     Location/Qualifiers
source                      1..123
                            mol_type = protein
                            organism = synthetic construct
SEQUENCE: 10
DVQLVESGGG VVQPGGSLRL SCAASGFTFS SYYMSWVRQA PGKGLEWVST INTDGDFTSY         60
ADSVKGRFTI SRDNAKNTLY LQMNSLRPED TALYYCARAR GPYSRGSQGH DYRGQGTLVT        120
VSS                                                                     123
```

```
SEQ ID NO: 11            moltype = AA   length = 121
FEATURE                  Location/Qualifiers
source                   1..121
                         mol_type = protein
                         organism = synthetic construct
SEQUENCE: 11
EVQLVESGGG LVQPGGSLRL SCAASGFTFS SYAMHWVRQA PGKGLEYVSA ISSQGGSTYY    60
ANSVKGRFTI SRDNSKNTLY LQMGSLRAED TAVYYCARGE AYWYRWAFDY WGQGTLVTVS   120
S                                                                   121

SEQ ID NO: 12            moltype = AA   length = 107
FEATURE                  Location/Qualifiers
source                   1..107
                         mol_type = protein
                         organism = synthetic construct
SEQUENCE: 12
DIQMTQSPST LSASVGDRVT ITCRASQSIS SWLAWYQQKP GKAPKLLIYD ASSLESGVPS    60
RFSGSGSGTE FTLTISSLQP DDFATYYCQQ YSDYSYTFGQ GTKVEIK                 107

SEQ ID NO: 13            moltype = AA   length = 8
FEATURE                  Location/Qualifiers
source                   1..8
                         mol_type = protein
                         organism = synthetic construct
SEQUENCE: 13
GSFFSIDT                                                              8

SEQ ID NO: 14            moltype = AA   length = 7
FEATURE                  Location/Qualifiers
source                   1..7
                         mol_type = protein
                         organism = synthetic construct
SEQUENCE: 14
VTSGGLT                                                               7

SEQ ID NO: 15            moltype = AA   length = 15
FEATURE                  Location/Qualifiers
source                   1..15
                         mol_type = protein
                         organism = synthetic construct
SEQUENCE: 15
SARIRTSGGG GWSTY                                                     15

SEQ ID NO: 16            moltype = AA   length = 121
FEATURE                  Location/Qualifiers
source                   1..121
                         mol_type = protein
                         organism = unidentified
SEQUENCE: 16
DVQLVESGGG VVQPGGSLRL SCAASGSFFS IDTMDWYRQA PGKQRELVTG VTSGGLTNYA    60
DSVKGRFTIS IDNAKNTVYL QMNSLRPEDT ALYYCSARIR TSGGGGWSTY WGQGTLVTVS   120
S                                                                   121

SEQ ID NO: 17            moltype = AA   length = 8
FEATURE                  Location/Qualifiers
source                   1..8
                         mol_type = protein
                         organism = synthetic construct
SEQUENCE: 17
GYTFTSYG                                                              8

SEQ ID NO: 18            moltype = AA   length = 8
FEATURE                  Location/Qualifiers
source                   1..8
                         mol_type = protein
                         organism = synthetic construct
SEQUENCE: 18
ISAYTGNT                                                              8

SEQ ID NO: 19            moltype = AA   length = 9
FEATURE                  Location/Qualifiers
source                   1..9
                         mol_type = protein
                         organism = synthetic construct
SEQUENCE: 19
ARDGYPIDY                                                             9

SEQ ID NO: 20            moltype = AA   length = 6
```

```
FEATURE              Location/Qualifiers
source               1..6
                     mol_type = protein
                     organism = synthetic construct
SEQUENCE: 20
QSISSW                                                                    6

SEQ ID NO: 21        moltype =    length =
SEQUENCE: 21
000

SEQ ID NO: 22        moltype = AA   length = 9
FEATURE              Location/Qualifiers
source               1..9
                     mol_type = protein
                     organism = synthetic construct
SEQUENCE: 22
QQYTSYSDT                                                                 9

SEQ ID NO: 23        moltype = AA   length = 116
FEATURE              Location/Qualifiers
source               1..116
                     mol_type = protein
                     organism = synthetic construct
SEQUENCE: 23
QVQLVQSGAE VKKPGASVKV SCKASGYTFT SYGISWVRQA PGQGLEWMGW ISAYTGNTNY          60
AQKLQGRVTM TTDTSTSTAY MELRSLRSDD TAVYYCARDG YPIDYWGQGT LVTVSS             116

SEQ ID NO: 24        moltype = AA   length = 107
FEATURE              Location/Qualifiers
source               1..107
                     mol_type = protein
                     organism = synthetic construct
SEQUENCE: 24
DIQMTQSPST LSASVGDRVT ITCRASQSIS SWLAWYQQKP GKAPKLLIYD ASSLESGVPS          60
RFSGSGSGTE FTLTISSLQP DDFATYYCQQ YTSYSDTFGQ GTKVEIK                       107

SEQ ID NO: 25        moltype = AA   length = 8
FEATURE              Location/Qualifiers
source               1..8
                     mol_type = protein
                     organism = synthetic construct
SEQUENCE: 25
GFTFSSYA                                                                  8

SEQ ID NO: 26        moltype = AA   length = 8
FEATURE              Location/Qualifiers
source               1..8
                     mol_type = protein
                     organism = synthetic construct
SEQUENCE: 26
ISSQGGST                                                                  8

SEQ ID NO: 27        moltype = AA   length = 14
FEATURE              Location/Qualifiers
source               1..14
                     mol_type = protein
                     organism = synthetic construct
SEQUENCE: 27
ARGGSGWYNS EFDY                                                           14

SEQ ID NO: 28        moltype = AA   length = 6
FEATURE              Location/Qualifiers
source               1..6
                     mol_type = protein
                     organism = synthetic construct
SEQUENCE: 28
QSISSW                                                                    6

SEQ ID NO: 29        moltype =    length =
SEQUENCE: 29
000

SEQ ID NO: 30        moltype = AA   length = 9
FEATURE              Location/Qualifiers
source               1..9
                     mol_type = protein
                     organism = synthetic construct
SEQUENCE: 30
```

```
QQYNDYSYT                                                                      9

SEQ ID NO: 31           moltype = AA  length = 121
FEATURE                 Location/Qualifiers
source                  1..121
                        mol_type = protein
                        organism = synthetic construct
SEQUENCE: 31
EVQLVESGGG LVQPGGSLRL SCAASGFTFS SYAMHWVRQA PGKGLEYVSA ISSQGGSTYY    60
ANSVKGRFTI SRDNSKNTLY LQMGSLRAED TAVYYCARGG SGWYNSEFDY WGQGTLVTVS   120
S                                                                   121

SEQ ID NO: 32           moltype = AA  length = 107
FEATURE                 Location/Qualifiers
source                  1..107
                        mol_type = protein
                        organism = synthetic construct
SEQUENCE: 32
DIQMTQSPST LSASVGDRVT ITCRASQSIS SWLAWYQQKP GKAPKLLIYD ASSLESGVPS    60
RFSGSGSGTE FTLTISSLQP DDFATYYCQQ YNDYSYTFGQ GTKVEIK                 107

SEQ ID NO: 33           moltype = AA  length = 214
FEATURE                 Location/Qualifiers
source                  1..214
                        mol_type = protein
                        organism = synthetic construct
SEQUENCE: 33
DIQMTQSPST LSASVGDRVT ITCRASQSIS SWLAWYQQKP GKAPKLLIYD ASSLESGVPS    60
RFSGSGSGTE FTLTISSLQP DDFATYYCQQ YSDYSYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 34           moltype = AA  length = 214
FEATURE                 Location/Qualifiers
source                  1..214
                        mol_type = protein
                        organism = synthetic construct
SEQUENCE: 34
DIQMTQSPST LSASVGDRVT ITCRASQSIS SWLAWYQQKP GKAPKLLIYD ASSLESGVPS    60
RFSGSGSGTE FTLTISSLQP DDFATYYCQQ YTSYSDTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 35           moltype = AA  length = 214
FEATURE                 Location/Qualifiers
source                  1..214
                        mol_type = protein
                        organism = synthetic construct
SEQUENCE: 35
DIQMTQSPST LSASVGDRVT ITCRASQSIS SWLAWYQQKP GKAPKLLIYD ASSLESGVPS    60
RFSGSGSGTE FTLTISSLQP DDFATYYCQQ YNDYSYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 36           moltype = AA  length = 450
FEATURE                 Location/Qualifiers
source                  1..450
                        mol_type = protein
                        organism = synthetic construct
SEQUENCE: 36
EVQLVESGGG LVQPGGSLRL SCAASGFTFS SYAMHWVRQA PGKGLEYVSA ISSQGGSTYY    60
ANSVKGRFTI SRDNSKNTLY LQMGSLRAED TAVYYCARGE AYWYRWAFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPCRD   360
ELTKNQVSLW CLVKGFYPSD IAVEWESNGQ PENNYKTTPP VLDSDGSFFL YSKLTVDKSR   420
WQQGNVFSCS VMHEALHNHY TQKSLSLSPG                                    450

SEQ ID NO: 37           moltype = AA  length = 450
FEATURE                 Location/Qualifiers
source                  1..450
                        mol_type = protein
                        organism = synthetic construct
SEQUENCE: 37
EVQLVESGGG LVQPGGSLRL SCAASGFTFS SYAMHWVRQA PGKGLEYVSA ISSQGGSTYY    60
ANSVKGRFTI SRDNSKNTLY LQMGSLRAED TAVYYCARGE AYWYRWAFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
```

```
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPCRD    360
ELTKNQVSLW CLVKGFYPSD IAVEWESNGQ PENNYKTTPP VLDSDGSFFL YSKLTVDKSR    420
WQQGNVFSCS VMHEALHNHY TQKSLSLSPG                                    450

SEQ ID NO: 38           moltype = AA   length = 445
FEATURE                 Location/Qualifiers
source                  1..445
                        mol_type = protein
                        organism = synthetic construct
SEQUENCE: 38
QVQLVQSGAE VKKPGASVKV SCKASGYTFT SYGISWVRQA PGQGLEWMGW ISAYTGNTNY    60
AQKLQGRVTM TTDTSTSTAY MELRSLRSDD TAVYYCARDG YPIDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPCRDELTKN    360
QVSLWCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 39           moltype = AA   length = 445
FEATURE                 Location/Qualifiers
source                  1..445
                        mol_type = protein
                        organism = synthetic construct
SEQUENCE: 39
QVQLVQSGAE VKKPGASVKV SCKASGYTFT SYGISWVRQA PGQGLEWMGW ISAYTGNTNY    60
AQKLQGRVTM TTDTSTSTAY MELRSLRSDD TAVYYCARDG YPIDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPCRDELTKN    360
QVSLWCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 40           moltype = AA   length = 450
FEATURE                 Location/Qualifiers
source                  1..450
                        mol_type = protein
                        organism = synthetic construct
SEQUENCE: 40
EVQLVESGGG LVQPGGSLRL SCAASGFTFS SYAMHWVRQA PGKGLEYVSA ISSQGGSTYY    60
ANSVKGRFTI SRDNSKNTLY LQMGSLRAED TAVYYCARGG SGWYNSEFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPCRD    360
ELTKNQVSLW CLVKGFYPSD IAVEWESNGQ PENNYKTTPP VLDSDGSFFL YSKLTVDKSR    420
WQQGNVFSCS VMHEALHNHY TQKSLSLSPG                                    450

SEQ ID NO: 41           moltype = AA   length = 354
FEATURE                 Location/Qualifiers
source                  1..354
                        mol_type = protein
                        organism = synthetic construct
SEQUENCE: 41
DVQLVESGGG VVQPGGSLRL SCAASGFTFS SYYMSWVRQA PGKGLEWVST INTDGDFTSY    60
ADSVKGRFTI SRDNAKNTLY LQMNSLRPED TALYYCARAR GPYSRGSQGH DYRGQGTLVT    120
VSSSGGGSDK THTCPPCPAP EAAGGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKALPAPI    240
EKTISKAKGQ PREPQVCTLP PSRDELTKNQ VSLSCAVKGF YPSDIAVEWE SNGQPENNYK    300
TTPPVLDSDG SFFLVSKLTV DKSRWQQGNV FSCSVMHEAL HNRFTQKSLS LSPG          354

SEQ ID NO: 42           moltype = AA   length = 352
FEATURE                 Location/Qualifiers
source                  1..352
                        mol_type = protein
                        organism = synthetic construct
SEQUENCE: 42
DVQLVESGGG VVQPGGSLRL SCAASGSFFS IDTMDWYRQA PGKQRELVTG VTSGGLTNYA    60
DSVKGRFTIS IDNAKNTVYL QMNSLRPEDT ALYYCSARIR TSGGGWSTY WGQGTLVTVS    120
SGGGGSDKTH TCPPCPAPEA AGGPSVFLFP PKPKDTLMIS RTPEVTCVVV DVSHEDPEVK    180
FNWYVDGVEV HNAKTKPREE QYNSTYRVVS VLTVLHQDWL NGKEYKCKVS NKALPAPIEK    240
TISKAKGQPR EPQVCTLPPS RDELTKNQVS LSCAVKGFYP SDIAVEWESN GQPENNYKTT    300
PPVLDSDGSF FLVSKLTVDK SRWQQGNVFS CSVMHEALHN RFTQKSLSLS PG            352

SEQ ID NO: 43           moltype = AA   length = 216
FEATURE                 Location/Qualifiers
source                  1..216
```

```
                          mol_type = protein
                          organism = synthetic construct
SEQUENCE: 43
QSVLTQPPSV  SAAPGQKVTI  SCSGSSSNIG  NNYVSWYQQL  PGTAPKLLIY  DNNKRPSGIP   60
DRFSGSKSGT  SATLGITGLQ  TGDEADYYCG  TWDSSLTAYV  FGGGTKLTVL  GQPKAAPSVT  120
LFPPSSEELQ  ANKATLVCLI  SDFYPGAVTV  AWKADSSPVK  AGVETTTPSK  QSNNKYAASS  180
YLSLTPEQWK  SHRSYSCQVT  HEGSTVEKTV  APTECS                              216

SEQ ID NO: 44             moltype = AA  length = 450
FEATURE                   Location/Qualifiers
source                    1..450
                          mol_type = protein
                          organism = synthetic construct
SEQUENCE: 44
EVQLVESGGV  VVQPGGSLRL  SCAASGFTFD  DYTMHWVRQA  PGKGLEWVSL  ISWDGGSTYY   60
ADSVKGRFTI  SRDNSKNSLY  LQMNSLRTED  TAVYYCARDN  LWGYLTYFDY  WGQGTLVTVS  120
SASTKGPSVF  PLAPSSKSTS  GGTAALGCLV  KDYFPEPVTV  SWNSGALTSG  VHTFPAVLQS  180
SGLYSLSSVV  TVPSSSLGTQ  TYICNVNHKP  SNTKVDKKVE  PKSCDKTHTC  PPCPAPEAAG  240
GPSVFLFPPK  PKDTLMISRT  PEVTCVVVDV  SHEDPEVKFN  WYVDGVEVHN  AKTKPREEQY  300
NSTYRVVSVL  TVLHQDWLNG  KEYKCKVSNK  ALPAPIEKTI  SKAKGQPREP  QVYTLPPCRD  360
ELTKNQVSLW  CLVKGFYPSD  IAVEWESNGQ  PENNYKTTPP  VLDSDGSFFL  YSKLTVDKSR  420
WQQGNVFSCS  VMHEALHNHY  TQKSLSLSPG                                      450

SEQ ID NO: 45             moltype = AA  length = 351
FEATURE                   Location/Qualifiers
source                    1..351
                          mol_type = protein
                          organism = synthetic construct
SEQUENCE: 45
QVQLQESGGG  LVQPGGSLRL  SCVASGSISS  IDHVGWYRQA  PGKERVMVAF  INSGGRTTYP   60
DAVKGRFTIS  RDGASNTVFL  QMDGLKPDDT  AVYYCNVLLR  DRSGSGRTYW  GQGTQVTVSS  120
GGGGSDKTHT  CPPCPAPEAA  GGPSVFLFPP  KPKDTLMISR  TPEVTCVVVD  VSHEDPEVKF  180
NWYVDGVEVH  NAKTKPREEQ  YNSTYRVVSV  LTVLHQDWLN  GKEYKCKVSN  KALPAPIEKT  240
ISKAKGQPRE  PQVCTLPPSR  DELTKNQVSL  SCAVKGFYPS  DIAVEWESNG  QPENNYKTTP  300
PVLDSDGSFF  LVSKLTVDKS  RWQQGNVFSC  SVMHEALHNR  FTQKSLSLSP  G           351

SEQ ID NO: 46             moltype = AA  length = 118
FEATURE                   Location/Qualifiers
source                    1..118
                          mol_type = protein
                          organism = synthetic construct
SEQUENCE: 46
NKILVKQSPM  LVAYDNAVNL  SCKYSYNLFS  REFRASLHKG  LDSAVEVCVV  YGNYSQQLQV   60
YSKTGFNCDG  KLGNESVTFY  LQNLYVNQTD  IYFCKIEVMY  PPPYLDNEKS  NGTIIHVK    118

SEQ ID NO: 47             moltype = AA  length = 78
FEATURE                   Location/Qualifiers
source                    1..78
                          mol_type = protein
                          organism = synthetic construct
SEQUENCE: 47
VGDTYPSNDR  CCHECRPGNG  MVSRCSRSQN  TVCRPCGPGF  YNDVVSSKPC  KPCTWCNLRS   60
GSERKQLCTA  TQDTVCRC                                                    78

SEQ ID NO: 48             moltype = AA  length = 4
FEATURE                   Location/Qualifiers
source                    1..4
                          mol_type = protein
                          organism = synthetic construct
SEQUENCE: 48
KERE                                                                      4

SEQ ID NO: 49             moltype = AA  length = 4
FEATURE                   Location/Qualifiers
source                    1..4
                          mol_type = protein
                          organism = synthetic construct
SEQUENCE: 49
KQRE                                                                      4

SEQ ID NO: 50             moltype = AA  length = 4
FEATURE                   Location/Qualifiers
source                    1..4
                          mol_type = protein
                          organism = synthetic construct
SEQUENCE: 50
GLEW                                                                      4

SEQ ID NO: 51             moltype = AA  length = 5
```

-continued

```
FEATURE                 Location/Qualifiers
source                  1..5
                        mol_type = protein
                        organism = synthetic construct
SEQUENCE: 51
KEREL                                                                   5

SEQ ID NO: 52           moltype = AA  length = 5
FEATURE                 Location/Qualifiers
source                  1..5
                        mol_type = protein
                        organism = synthetic construct
SEQUENCE: 52
KEREF                                                                   5

SEQ ID NO: 53           moltype = AA  length = 5
FEATURE                 Location/Qualifiers
source                  1..5
                        mol_type = protein
                        organism = synthetic construct
SEQUENCE: 53
KQREL                                                                   5

SEQ ID NO: 54           moltype = AA  length = 5
FEATURE                 Location/Qualifiers
source                  1..5
                        mol_type = protein
                        organism = synthetic construct
SEQUENCE: 54
KQREF                                                                   5

SEQ ID NO: 55           moltype = AA  length = 5
FEATURE                 Location/Qualifiers
source                  1..5
                        mol_type = protein
                        organism = synthetic construct
SEQUENCE: 55
KEREG                                                                   5

SEQ ID NO: 56           moltype = AA  length = 5
FEATURE                 Location/Qualifiers
source                  1..5
                        mol_type = protein
                        organism = synthetic construct
SEQUENCE: 56
KQREW                                                                   5

SEQ ID NO: 57           moltype = AA  length = 5
FEATURE                 Location/Qualifiers
source                  1..5
                        mol_type = protein
                        organism = synthetic construct
SEQUENCE: 57
KQREG                                                                   5

SEQ ID NO: 58           moltype = AA  length = 4
FEATURE                 Location/Qualifiers
source                  1..4
                        mol_type = protein
                        organism = synthetic construct
SEQUENCE: 58
TERE                                                                    4

SEQ ID NO: 59           moltype = AA  length = 5
FEATURE                 Location/Qualifiers
source                  1..5
                        mol_type = protein
                        organism = synthetic construct
SEQUENCE: 59
TEREL                                                                   5

SEQ ID NO: 60           moltype = AA  length = 4
FEATURE                 Location/Qualifiers
source                  1..4
                        mol_type = protein
                        organism = synthetic construct
SEQUENCE: 60
TQRE                                                                    4
```

```
SEQ ID NO: 61          moltype = AA   length = 5
FEATURE                Location/Qualifiers
source                 1..5
                       mol_type = protein
                       organism = synthetic construct
SEQUENCE: 61
TQREL                                                                    5

SEQ ID NO: 62          moltype = AA   length = 4
FEATURE                Location/Qualifiers
source                 1..4
                       mol_type = protein
                       organism = synthetic construct
SEQUENCE: 62
KECE                                                                     4

SEQ ID NO: 63          moltype = AA   length = 5
FEATURE                Location/Qualifiers
source                 1..5
                       mol_type = protein
                       organism = synthetic construct
SEQUENCE: 63
KECEL                                                                    5

SEQ ID NO: 64          moltype = AA   length = 5
FEATURE                Location/Qualifiers
source                 1..5
                       mol_type = protein
                       organism = synthetic construct
SEQUENCE: 64
KECER                                                                    5

SEQ ID NO: 65          moltype = AA   length = 4
FEATURE                Location/Qualifiers
source                 1..4
                       mol_type = protein
                       organism = synthetic construct
SEQUENCE: 65
KQCE                                                                     4

SEQ ID NO: 66          moltype = AA   length = 5
FEATURE                Location/Qualifiers
source                 1..5
                       mol_type = protein
                       organism = synthetic construct
SEQUENCE: 66
KQCEL                                                                    5

SEQ ID NO: 67          moltype = AA   length = 4
FEATURE                Location/Qualifiers
source                 1..4
                       mol_type = protein
                       organism = synthetic construct
SEQUENCE: 67
RERE                                                                     4

SEQ ID NO: 68          moltype = AA   length = 5
FEATURE                Location/Qualifiers
source                 1..5
                       mol_type = protein
                       organism = synthetic construct
SEQUENCE: 68
REREG                                                                    5

SEQ ID NO: 69          moltype = AA   length = 4
FEATURE                Location/Qualifiers
source                 1..4
                       mol_type = protein
                       organism = synthetic construct
SEQUENCE: 69
RQRE                                                                     4

SEQ ID NO: 70          moltype = AA   length = 5
FEATURE                Location/Qualifiers
source                 1..5
                       mol_type = protein
                       organism = synthetic construct
SEQUENCE: 70
RQREL                                                                    5
```

```
SEQ ID NO: 71           moltype = AA  length = 5
FEATURE                 Location/Qualifiers
source                  1..5
                        mol_type = protein
                        organism = synthetic construct
SEQUENCE: 71
RQREF                                                                    5

SEQ ID NO: 72           moltype = AA  length = 5
FEATURE                 Location/Qualifiers
source                  1..5
                        mol_type = protein
                        organism = synthetic construct
SEQUENCE: 72
RQREW                                                                    5

SEQ ID NO: 73           moltype = AA  length = 4
FEATURE                 Location/Qualifiers
source                  1..4
                        mol_type = protein
                        organism = synthetic construct
SEQUENCE: 73
QERE                                                                     4

SEQ ID NO: 74           moltype = AA  length = 5
FEATURE                 Location/Qualifiers
source                  1..5
                        mol_type = protein
                        organism = synthetic construct
SEQUENCE: 74
QEREG                                                                    5

SEQ ID NO: 75           moltype = AA  length = 4
FEATURE                 Location/Qualifiers
source                  1..4
                        mol_type = protein
                        organism = synthetic construct
SEQUENCE: 75
QQRE                                                                     4

SEQ ID NO: 76           moltype = AA  length = 5
FEATURE                 Location/Qualifiers
source                  1..5
                        mol_type = protein
                        organism = synthetic construct
SEQUENCE: 76
QQREW                                                                    5

SEQ ID NO: 77           moltype = AA  length = 5
FEATURE                 Location/Qualifiers
source                  1..5
                        mol_type = protein
                        organism = synthetic construct
SEQUENCE: 77
QQREL                                                                    5

SEQ ID NO: 78           moltype = AA  length = 5
FEATURE                 Location/Qualifiers
source                  1..5
                        mol_type = protein
                        organism = synthetic construct
SEQUENCE: 78
QQREF                                                                    5

SEQ ID NO: 79           moltype = AA  length = 4
FEATURE                 Location/Qualifiers
source                  1..4
                        mol_type = protein
                        organism = synthetic construct
SEQUENCE: 79
KGRE                                                                     4

SEQ ID NO: 80           moltype = AA  length = 5
FEATURE                 Location/Qualifiers
source                  1..5
                        mol_type = protein
                        organism = synthetic construct
SEQUENCE: 80
```

KGREG                                                                          5

SEQ ID NO: 81           moltype = AA  length = 4
FEATURE                 Location/Qualifiers
source                  1..4
                        mol_type = protein
                        organism = synthetic construct
SEQUENCE: 81
KDRE                                                                           4

SEQ ID NO: 82           moltype = AA  length = 5
FEATURE                 Location/Qualifiers
source                  1..5
                        mol_type = protein
                        organism = synthetic construct
SEQUENCE: 82
KDREV                                                                          5

SEQ ID NO: 83           moltype = AA  length = 5
FEATURE                 Location/Qualifiers
source                  1..5
                        mol_type = protein
                        organism = synthetic construct
SEQUENCE: 83
DECKL                                                                          5

SEQ ID NO: 84           moltype = AA  length = 5
FEATURE                 Location/Qualifiers
source                  1..5
                        mol_type = protein
                        organism = synthetic construct
SEQUENCE: 84
NVCEL                                                                          5

SEQ ID NO: 85           moltype = AA  length = 4
FEATURE                 Location/Qualifiers
source                  1..4
                        mol_type = protein
                        organism = synthetic construct
SEQUENCE: 85
GVEW                                                                           4

SEQ ID NO: 86           moltype = AA  length = 4
FEATURE                 Location/Qualifiers
source                  1..4
                        mol_type = protein
                        organism = synthetic construct
SEQUENCE: 86
EPEW                                                                           4

SEQ ID NO: 87           moltype = AA  length = 4
FEATURE                 Location/Qualifiers
source                  1..4
                        mol_type = protein
                        organism = synthetic construct
SEQUENCE: 87
GLER                                                                           4

SEQ ID NO: 88           moltype = AA  length = 4
FEATURE                 Location/Qualifiers
source                  1..4
                        mol_type = protein
                        organism = synthetic construct
SEQUENCE: 88
DQEW                                                                           4

SEQ ID NO: 89           moltype = AA  length = 4
FEATURE                 Location/Qualifiers
source                  1..4
                        mol_type = protein
                        organism = synthetic construct
SEQUENCE: 89
DLEW                                                                           4

SEQ ID NO: 90           moltype = AA  length = 4
FEATURE                 Location/Qualifiers
source                  1..4
                        mol_type = protein
                        organism = synthetic construct

```
SEQUENCE: 90
GIEW                                                                            4

SEQ ID NO: 91           moltype = AA  length = 4
FEATURE                 Location/Qualifiers
source                  1..4
                        mol_type = protein
                        organism = synthetic construct
SEQUENCE: 91
ELEW                                                                            4

SEQ ID NO: 92           moltype = AA  length = 4
FEATURE                 Location/Qualifiers
source                  1..4
                        mol_type = protein
                        organism = synthetic construct
SEQUENCE: 92
GPEW                                                                            4

SEQ ID NO: 93           moltype = AA  length = 4
FEATURE                 Location/Qualifiers
source                  1..4
                        mol_type = protein
                        organism = synthetic construct
SEQUENCE: 93
EWLP                                                                            4

SEQ ID NO: 94           moltype = AA  length = 4
FEATURE                 Location/Qualifiers
source                  1..4
                        mol_type = protein
                        organism = synthetic construct
SEQUENCE: 94
GPER                                                                            4

SEQ ID NO: 95           moltype = AA  length = 4
FEATURE                 Location/Qualifiers
source                  1..4
                        mol_type = protein
                        organism = synthetic construct
SEQUENCE: 95
GLER                                                                            4

SEQ ID NO: 96           moltype = AA  length = 4
FEATURE                 Location/Qualifiers
source                  1..4
                        mol_type = protein
                        organism = synthetic construct
SEQUENCE: 96
ELEW                                                                            4

SEQ ID NO: 97           moltype = AA  length = 8
FEATURE                 Location/Qualifiers
source                  1..8
                        mol_type = protein
                        organism = synthetic construct
SEQUENCE: 97
GFTFDDYT                                                                        8

SEQ ID NO: 98           moltype = AA  length = 8
FEATURE                 Location/Qualifiers
source                  1..8
                        mol_type = protein
                        organism = synthetic construct
SEQUENCE: 98
ISWDGGST                                                                        8

SEQ ID NO: 99           moltype = AA  length = 14
FEATURE                 Location/Qualifiers
source                  1..14
                        mol_type = protein
                        organism = synthetic construct
SEQUENCE: 99
ARDNLWGYLT YFDY                                                                14

SEQ ID NO: 100          moltype = AA  length = 8
FEATURE                 Location/Qualifiers
source                  1..8
                        mol_type = protein
```

```
                        organism = synthetic construct
SEQUENCE: 100
SSNIGNNY                                                               8

SEQ ID NO: 101          moltype =    length =
SEQUENCE: 101
000

SEQ ID NO: 102          moltype = AA   length = 11
FEATURE                 Location/Qualifiers
source                  1..11
                        mol_type = protein
                        organism = synthetic construct
SEQUENCE: 102
GTWDSSLTAY V                                                           11

SEQ ID NO: 103          moltype = AA   length = 121
FEATURE                 Location/Qualifiers
source                  1..121
                        mol_type = protein
                        organism = synthetic construct
SEQUENCE: 103
EVQLVESGGV VVQPGGSLRL SCAASGFTFD DYTMHWVRQA PGKGLEWVSL ISWDGGSTYY       60
ADSVKGRFTI SRDNSKNSLY LQMNSLRTED TAVYYCARDN LWGYLTYFDY WGQGTLVTVS      120
S                                                                     121

SEQ ID NO: 104          moltype = AA   length = 110
FEATURE                 Location/Qualifiers
source                  1..110
                        mol_type = protein
                        organism = synthetic construct
SEQUENCE: 104
QSVLTQPPSV SAAPGQKVTI SCSGSSSNIG NNYVSWYQQL PGTAPKLLIY DNNKRPSGIP       60
DRFSGSKSGT SATLGITGLQ TGDEADYYCG TWDSSLTAYV FGGGTKLTVL                 110
```